United States Patent [19]
Breslin et al.

[11] Patent Number: 5,585,359
[45] Date of Patent: Dec. 17, 1996

[54] INHIBITORS OF FARNESYL-PROTEIN TRANSFERASE

[75] Inventors: Michael J. Breslin, Drexel Hill; S. J. deSolms, Norristown; Samuel L. Graham, Schwenksville; John H. Hutchinson, Philadelphia; Gerald E. Stokker, Gwynedd Valley, all of Pa.

[73] Assignee: Merck & Co., Inc., Rahway, N.J.

[21] Appl. No.: 315,171

[22] Filed: Sep. 29, 1994

[51] Int. Cl.$^6$ .............................. C07K 5/00; C07K 7/00; C07K 17/00; A61K 38/00
[52] U.S. Cl. .......................... 514/19; 514/18; 530/330; 530/331; 560/13; 560/16; 558/302; 562/426
[58] Field of Search ..................... 514/18, 19; 530/330, 530/331; 560/13, 16; 558/302; 562/426

[56] References Cited

U.S. PATENT DOCUMENTS

| | | |
|---|---|---|
| 5,043,268 | 8/1991 | Stock . |
| 5,141,851 | 8/1992 | Brown et al. . |
| 5,238,922 | 8/1993 | Graham et al. ............... 514/18 |
| 5,326,773 | 7/1994 | de Solms et al. . |
| 5,340,828 | 8/1994 | Graham et al. . |
| 5,352,705 | 10/1994 | Deana et al. . |

FOREIGN PATENT DOCUMENTS

| | | |
|---|---|---|
| 0456180A1 | 11/1991 | European Pat. Off. . |
| 0618221A2 | 10/1994 | European Pat. Off. . |
| WO91/16340 | 10/1991 | WIPO . |

OTHER PUBLICATIONS

Gibbs, J. B., et al. "Selective Inhibition of Farnesyl–Protein Transferase Blocks Ras Processing in Vivo", The Journal of Biological Chemistry, vol. 268, No. 11, pp. 7617–7620 (1993).

Goldstein, J. L. et al., "Nonfarnesylated Tetrapeptide Inhibitors of Protein Farnesyltransferase", The Journal of Biological Chemistry, vol. 266, No. 24 pp. 15575–15578 (1991).

James, G. L. et al., "Benzodiazepine Peptidomimetic BZA–5B Interrupts the MAP Kinase Activation Pathway in H–Ras–transformed Rat–1 Cells, but Not in Untransformed Cells", The Journal of Biological Chemistry, vol. 369, No. 44, pp. 27705–27714 (1994).

James, G. L. et al., "Benzodiazepine Peptidomimetics: Potent Inhibitors of Ras Farnesylation in Animal Cells", Science, vol. 260, pp. 1937–1942 (1993).

Kohl, N. E. et al., "Selective Inhibition of ras–Dependent Transformation by a Farnesyltransferase Inhibitor", Science, vol. 260, pp. 1934–1937 (1993).

Kohl, N. E. et al., "Protein farnesyltransferase inhibitors block the growth of ras–dependent tumors in nude mice", Proc. Natl. Acad. Sci. USA, Med. Sciences, vol. 91, pp. 9141–9145 (1994).

Pompliano, D. L., "Steady–State Kinetic Mechanism of Ras Farnesyl:Protein Transferase", Biochemistry, vol. 31, pp. 3800–3807 (1992).

Lorenzino, L. S. et al., "A peptidomimetic Inhibitor of Farnesyl:Protein Transferase Blocks the Anchorage–dependent and –independent Growth of Human Tumor Cell Lines," Cancer Research, 55, pp. 5302–5309 (1995).

Document Number 07/968,022, Inventor Merck et al , Filing Date Oct. 29, 1992.

Document Number 08/143,943, Inventor Merck et al , Filing Date Oct. 27, 1993.

Primary Examiner—Toni R. Scheiner
Assistant Examiner—Sheila J. Huff
Attorney, Agent, or Firm—David A. Muthard; Mark R. Daniel

[57] ABSTRACT

The present invention comprises analogs of the CAAX motif of the protein Ras that is modified by farnesylation in vivo. These CAAX analogs inhibit the farnesylation of Ras. Furthermore, these CAAX analogues differ from those previously described as inhibitors of Ras farnesyl transferase in that they do not have a thiol moiety. The lack of the thiol offers unique advantages in terms of improved pharmacokinetic behavior in animals, prevention of thiol-dependent chemical reactions, such as rapid autoxidation and disulfide formation with endogenous thiols, and reduced systemic toxicity. Further contained in this invention are chemotherapeutic compositions containing these farnesyl transferase inhibitors and methods for their production.

27 Claims, No Drawings

INHIBITORS OF FARNESYL-PROTEIN TRANSFERASE

BACKGROUND OF THE INVENTION

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., *Microbiol. Rev.* 53:171–286 (1989). Forms of Ras in cancer cells have mutations that distinguish the protein from Ras in normal cells.

At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Aaa is an aliphatic amino acid, the Xaa is any amino acid) (Willumsen et al., *Nature* 310:583–586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., *Cell* 57:1167 (1989); Casey et al., *Proc. Natl. Acad. Sci. USA* 86:8323 (1989)). In addition, Ha-Ras and N-Ras are palmitoylated via formation of a thioester on a Cys residue near a C-terminal Cys farnesyl acceptor (Gutierrez et al., *EMBO J.*8:1093–1098 (1989); Hancock et al., *Cell* 57:1167–1177 (1989)). Ki-Ras lacks the palmirate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg et al., *J. Biol. Chem.* 263:18236 (1988); Farnsworth et al., *J. Biol. Chem.* 264:20422 (1989)).

Inhibition of Ras farnesylation in vivo has been demonstrated with lovastatin (Merck & Co., Rahway, NJ) and compactin (Hancock et al., ibid; Casey et al., ibid; Schafer et al., *Science* 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss et at., *Cell*, 62:81–88 (1990); Schaber et al., *J. Biol. Chem.*, 265:14701–14704 (1990); Schafer et al., *Science*, 249:1133–1139 (1990); Manne et at., *Proc. Natl. Acad. Sci USA*, 87:754–7545 (1990)).

Inhibition of farnesyl-protein transferase and, thereby, of farnesylation of the Ras protein, blocks the ability of Ras to transform normal cells to cancer cells. The compounds of the invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no Cys-Aaa$^1$-Aaa$^2$-Xaa box membrane domain present) and activated (impaired GTPase activity, staying bound to GTP) form of Ras acts as a dominant negative Ras inhibitor of membrane-bound Ras function (Gibbs et at., *Proc. Natl. Acad. Sci. USA* 86:6630–6634(1989)). Cytosollocalized forms of Ras with normal GTPase activity do not act as inhibitors. Gibbs et al., ibid, showed this effect in Xenopus oocytes and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compound dose. Reduction of farnesyl-protein transferase enzyme activity by adjusting the compound dose would be useful for avoiding possible undesirable side effects resulting from interference with other metabolic processes which utilize the enzyme.

These compounds and their analogs are inhibitors of farnesyl-protein transferase. Farnesyl-protein transferase utilizes farnesyl pyrophosphate to covalently modify the Cys thiol group of the Ras CAAX box with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Previously, it has been demonstrated that tetrapeptides containing cysteine as an amino terminal residue with the CAAX sequence inhibit Ras farnesylation (Schaber et al., ibid; Reiss et. al., ibid; Reiss et al., *PNAS*, 88:732–736 (1991)). Such inhibitors may inhibit while serving as alternate substrates for the Ras farnesyl-transferase enzyme, or may be purely competitive inhibitors (U.S. Pat. No. 5,141,851, University of Texas).

It has also been demonstrated that certain inhibitors of farnesyl-protein transferase selectively block the processing of Ras oncoprotein intracellularly (N. E. Kohl et at., *Science*, 260:1934–1937 (1993) and G. L. James et at., *Science*, 260:1937–1942 (1993).

Recently, it has been shown that an inhibitor of farnesyl-protein transferase blocks the growth of ras-dependent tumors in nude mice (N. E. Kohlet al., *Proc. Natl. Acad. Sci U.S.A.*, 91:9141–9145 (1994).

Inhibitors of Ras farnesyl-protein transferase (FPTase) have been described in two general classes. The first are analogs of farnesyl diphosphate (FPP), while the second class of inhibitors is related to the protein substrate for the enzyme, Ras. Almost all of the peptide derived inhibitors that have been described are cysteine containing molecules that are related to the CAAX motif that is the signal for protein prenylation. The exception to this generalization is a class of natural products known as the pepticinnamins (Omura, et al., *J. Antibiotics* 46:222 (1993). In general, deletion of the thiol from a CAAX derivative dramatically reduces the inhibitory potency of these compounds. However, the thiol group potentially places limitations on the therapeutic application of FPTase inhibitors with respect to pharmacokinetics, pharmacodynamics and toxicity. Therefore, a functional replacement for the thiol is desirable. With the exception of the pepticinnamins, non-thiol FPTase inhibitors that are competitive with the Ras substrate have not been described and are the subject of this invention.

It is, therefore, an object of this invention to develop tetrapeptide-based compounds which do not have a thiol moiety, and which will inhibit farnesyl transferase and the post-translational functionalization of the oncogene Ras protein. It is a further object of this invention to develop chemotherapeutic compositions containing the compounds of this invention and methods for producing the compounds of this invention.

SUMMARY OF THE INVENTION

The present invention comprises analogs of the CAAX motif of the protein Ras that is modified by farnesylation in vivo. These CAAX analogs inhibit the farnesylation of Ras. Furthermore, these CAAX analogues differ from those previously described as inhibitors of Ras farnesyl transferase in that they do not have a thiol moiety. The lack of the thiol offers unique advantages in terms of improved pharmacokinetic behavior in animals, prevention of thiol-dependent chemical reactions, such as rapid autoxidation and disulfide formation with endogenous thiols, and reduced systemic toxicity. Further contained in this invention are chemotherapeutic compositions containing these farnesyl transferase inhibitors and methods for their production.

The compounds of this invention are illustrated by the formulae:

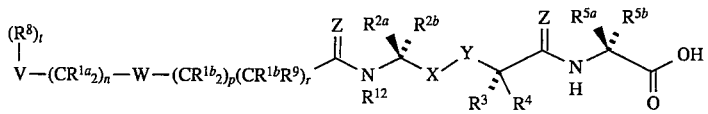

I

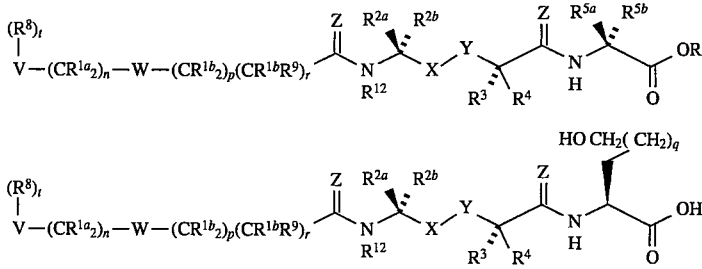

II

III and

IV

DETAILED DESCRIPTION OF THE INVENTION

The compounds of this invention inhibit the farnesylation of Ras. In a first embodiment of this invention, the Ras farnesyl transferase inhibitors are illustrated by the formula I:

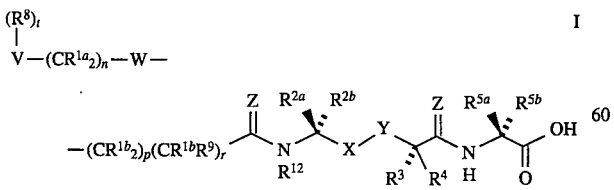

I wherein:

$R^{1a}$ is selected from:
a) hydrogen,
b) aryl, heterocyclic, cycloalkyl, alkenyl, alkynyl, $(R^{10})_2N\text{—}C(NR^{10})\text{—}$, $R^{10}C(O)\text{—}$, or $R^{10}OC(O)\text{—}$, and
c) $C_1\text{–}C_6$ alkyl unsubstituted or substituted by aryl, heterocyclic, cycloalkyl, alkenyl, alkynyl, $R^{10}O\text{—}$, $R^{11}S(O)_m\text{—}$, $R^{10}C(O)NR^{10}\text{—}$, CN, $(R^{10})_2N\text{—}C(NR^{10})\text{—}$, $R^{10}C(O)\text{—}$, $R^{10}OC(O)\text{—}$, $N_3$, $\text{—}N(R^{10})_2$, or $R^{11}OC(O)NR^{10}\text{—}$;

$R^{1b}$ is independently selected from:
a) hydrogen,
b) unsubstituted or substituted aryl, cycloalkyl, alkenyl, alkynyl, $(R^{10})_2N\text{—}C(NR^{10})\text{—}$, $R^{10}C(O)\text{—}$, or $R^{10}OC(O)\text{—}$, and
c) $C_1\text{–}C6$ alkyl unsubstituted or substituted by unsubstituted or substituted aryl, cycloalkyl, alkenyl, alkynyl, $R^{10}O\text{—}$, $R^{11}S(O)_m\text{—}$, $R^{10}C(O)NR^{10}\text{—}$, CN, $(R^{10})_2N\text{—}C(NR^{10})\text{—}$, $R^{10}C(O)\text{—}$, $R^{10}OC(O)\text{—}$, $N_3$, $\text{—}N(R^{10})_2$, or $R^{11}OC(O)NR^{10}\text{—}$;

provided that $R^{1b}$ is not $R^{10}C(O)NR^{10}\text{—}$ when $R^{1a}$ is alkenyl, V is hydrogen and X-Y is $\text{—}C(O)NR^{7a}\text{—}$;

$R^{2a}$ and $R^{2b}$ are independently selected from:
a) a side chain of a naturally occurring amino acid,
b) an oxidized form of a side chain of a naturally occurring amino acid which is:
i) methionine sulfoxide, or
ii) methionine sulfone,
c) substituted or unsubstituted $C_1\text{–}C_{20}$ alkyl, $C_2\text{–}C_{20}$ alkenyl, $C_3\text{–}C_{10}$ cycloalkyl, aryl or heterocyclic group,
wherein the substituent is selected from F, Cl, Br, $NO_2$, $R^{10}O\text{—}$, $R^{11}S(O)_m\text{—}$, $R^{10}C(O)NR^{10}\text{—}$, CN, $(R^{10})_2N\text{—}C(NR^{10})\text{—}$, $R^{10}C(O)\text{—}$, $R^{10}OC(O)\text{—}$, $N_3$, $\text{—}N(R^{10})_2$, $R^{11}OC(O)NR^{10}\text{—}$ and $C_1\text{–}C_{20}$ alkyl, and
d) $C_1\text{–}C_6$ alkyl substituted with an unsubstituted or substituted group selected from aryl, heterocycle and $C_3\text{–}C_{10}$ cycloalkyl; or $R^{2a}$ and $R^{2b}$ are combined to form $\text{—}(CH_2)_s\text{—}$;

$R^3$ and $R^4$ are independently selected from:
a) a side chain of a naturally occurring amino acid, b) an oxidized form of a side chain of a naturally occurring amino acid which is:
  i) methionine sulfoxide, or
  ii) methionine sulfone,
c) substituted or unsubstituted $C_1$–$C_{20}$ alkyl, $C_2$–$C_{20}$ alkenyl, $C_3$–$C_{10}$ cycloalkyl, aryl or heterocyclic group,
  wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl $R^3$ and $R^4$ are combined to form —$(CH_2)_s$—;

$R^{5a}$ and $R^{5b}$ independently selected from:
a) a side chain of a naturally occurring amino acid,
b) an oxidized form of a side chain of a naturally occurring amino acid which is:
  i) methionine sulfoxide, or
  ii) methionine sulfone,
c) substituted or unsubstituted $C_1$–$C_{20}$ alkyl, $C_2$–$C_{20}$ alkenyl, $C_3$–$C_{10}$ cycloalkyl, aryl or heterocyclic group,
  wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl; or $R^{5a}$ and $R^{5b}$ are combined to form —$(CH_2)_s$— wherein one of the carbon atoms is optionally replaced by a moiety selected from: $O, S(O)_m$, —NC(O)—, and —$N(COR^{10})$—;

X-Y is

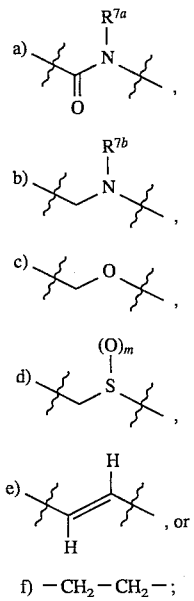

$R^{7a}$ is selected from
a) hydrogen,
b) unsubstituted or substituted aryl,
c) unsubstituted or substituted heterocyclic,
d) unsubstituted or substituted cycloalkyl, and
e) $C_1$–$C_6$ alkyl substituted with hydrogen or an unsubstituted or substituted group selected from aryl, heterocyclic and cycloalkyl;

$R^{7b}$ is selected from
a) hydrogen,
b) unsubstituted or substituted aryl,
c) unsubstituted or substituted heterocyclic,
d) unsubstituted or substituted cycloalkyl,
e) $C_1$–$C_6$ alkyl substituted with hydrogen or an unsubstituted or substituted group selected from aryl, heterocyclic and cycloalkyl,
f) a carbonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl, and
g) a sulfonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl;

$R^8$ is independently selected from:
a) hydrogen,
b) aryl, heterocyclic, cycloalkyl, alkenyl, alkynyl, perfluoroalkyl, F, Cl, Br, $R^{10}O$—, $R^{11}S(O)_m$—, $R^{10}C(O)NR^{10}$—, CN, $NO_2$, $R^{10}_2N$—$C(NR^{10})$—, $R^{10}C(O)$—, $R^{10}OC(O)$—, $N_3$, —$N(R^{10})_2$, or $R^{11}OC(O)NR^{10}$—, and
c) $C_1$–$C_6$ alkyl unsubstituted or substituted by aryl, heterocyclic, cycloalkyl, alkenyl, alkynyl, perfluoroalkyl, F, Cl, Br, $R^{10}O$—, $R^{11}S(O)_m$, $R^{10}C(O)NH$—, CN, $H_2N$—$C(NH)$—, $R^{10}C(O)$—, $R^{10}OC(O)$—, $N_3$, —$N(R^{10})_2$, or $R^{11}OC(O)NH$—;

$R^9$ is selected from:
hydrogen, $C_1$–$C_6$ alkyl, $R^{10}O$—, $R^{11}S(O)_m$—, $R^{10}C(O)NR^{10}$—, CN, $NO_2$, $N_3$, —$N(R^{10})_2$, and $R^{11}OC(O)NR^{10}$—;
provided that $R^9$ is not $R^{10}C(O)NR^{10}$— when $R^{1a}$ is alkenyl, V is hydrogen and X-Y is —$C(O)NR^{7a}$—;

$R^{10}$ is independently selected from hydrogen, $C_1$–$C_6$ alkyl, benzyl and aryl;

$R^{11}$ is independently selected from $C_1$–$C_6$ alkyl and aryl;

$R^{12}$ is hydrogen or $C_1$–$C_6$ alkyl;

V is selected from:
a) aryl;
b) heterocycle; or
c) hydrogen;

W is
—$S(O)_m$—, —O—, —NHC(O)—, —C(O)NH—, —$NHSO_2$—, —$SO_2NH$—, —$N(R^{7a})$— or —$N[C(O)R^{7a}]$—;

Z is independently $H_2$ or O m is 0, 1 or 2;

n is 0, 1, 2, 3 or 4, provided that n≠0 when V is hydrogen and W is —$S(O)_m$;

p is 0, 1, 2, 3 or 4, provided that p≠0 when $R^9$ is not hydrogen or $C_1$–$C_6$ lower alkyl;

r is 0 or 1;

s is 4 or 5; and t is 0, 1 or 2, provided that t=0 when V is hydrogen;

or the pharmaceutically acceptable salts thereof.

In a second embodiment of this invention the prodrugs of compounds of formula I are illustrated by the formula II:

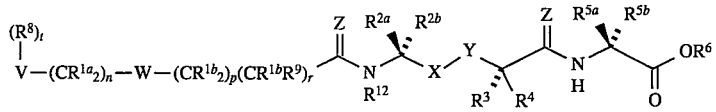

wherein:

$R^{1a}$ is selected from:
  a) hydrogen,
  b) aryl, heterocyclic, cycloalkyl, alkenyl, alkynyl, $(R^{10})_2N$—$C(NR^{10})$—, $R^{10}C(O)$—, or $R^{10}OC(O)$—, and
  c) $C_1$–$C_6$ alkyl unsubstituted or substituted by aryl, heterocyclic, cycloalkyl, alkenyl, alkynyl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;

$R^{1b}$ is independently selected from:
  a) hydrogen,
  b) unsubstituted or substituted aryl, cycloalkyl, alkenyl, alkynyl, $(R^{10})_2N$—$C(NR^{10})$—, $R^{10}C(O)$—, or $R^{10}OC(O)$—, and
  c) $C_1$–$C_6$ alkyl unsubstituted or substituted by unsubstituted or substituted aryl, cycloalkyl, alkenyl, alkynyl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;

provided that $R^{1b}$ is not $R^{10}C(O)NR^{10}$— when $R^{1a}$ is alkenyl, V is hydrogen and X-Y is —$C(O)NR^{7a}$—;

$R^{2a}$ and $R^{2b}$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1$–$C_{20}$ alkyl, $C_2$–$C_{20}$ alkenyl, $C_3$–$C_{10}$ cycloalkyl, aryl or heterocyclic group,
    wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
  d) $C_1$–$C_6$ alkyl substituted with an unsubstituted or substituted group selected from aryl, heterocycle and $C_3$–$C_{10}$ cycloalkyl; or $R^{2a}$ and $R^{2b}$ are combined to form —$(CH_2)_s$—;

$R^3$ and $R^4$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1$–$C_{20}$ alkyl, $C_2$–$C_{20}$ alkenyl, $C_3$–$C_{10}$ cycloalkyl, aryl or heterocyclic group,
    wherein the substituent is selected from F, Cl, Br, $N(R^{10})_2$, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
  d) $C_1$–$C_6$ alkyl substituted with an unsubstituted or substituted group selected from aryl, heterocycle and $C_3$–$C_{10}$ cycloalkyl; or $R^3$ and $R^4$ are combined to form —$(CH_2)_s$—;

$R^{5a}$ and $R^{5b}$ independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1$–$C_{20}$ alkyl, $C_2$–$C_{20}$ alkenyl, $C_3$–$C_{10}$ cycloalkyl, aryl or heterocyclic group,
    wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$—, and $C_1$–$C_{20}$ alkyl, and
  d) $C_1$–$C_6$ alkyl substituted with an unsubstituted or substituted group selected from aryl, heterocycle and $C_3$–$C_{10}$ cycloalkyl; or $R^{5a}$ and $R^{5b}$ are combined to form —$(CH_2)_s$— wherein one of the carbon atoms is optionally replaced by a moiety selected from: $O, S(O)_m$, —$NC(O)$—, and —$N(COR^{10})$—;

$R^6$ is
  a) substituted or unsubstituted $C_1$–$C_8$ alkyl, wherein the substituent on the alkyl is selected from:
    1) aryl,
    2) heterocycle,
    3) —$N(R^{11})_2$,
    4) —$OR^{10}$, or
  b)

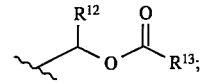

X-Y is a) 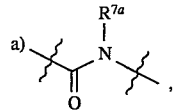

b) 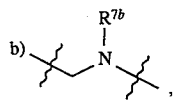

c) 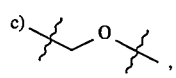

d) 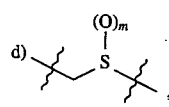

e) 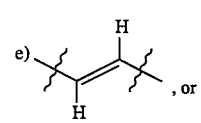, or f) —$CH_2$—$CH_2$—;

$R^{7a}$ is selected from
  a) hydrogen,
  b) unsubstituted or substituted aryl, c) unsubstituted or substituted heterocyclic,
d) unsubstituted or substituted cycloalkyl, and
e) $C_1$–$C_6$ alkyl substituted with hydrogen or an unsubstituted or substituted group selected from aryl, heterocyclic and cycloalkyl;

$R^{7b}$ is selected from
a) hydrogen,
b) unsubstituted or substituted aryl,
c) unsubstituted or substituted heterocyclic,
d) unsubstituted or substituted cycloalkyl,

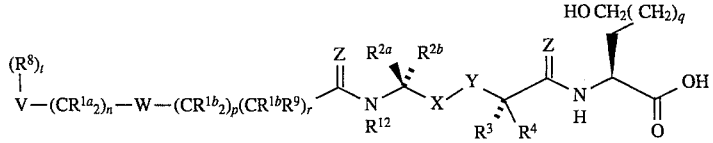

e) $C_1$–$C_6$ alkyl substituted with hydrogen or an unsubstituted or substituted group selected from aryl, heterocyclic and cycloalkyl,
f) a carbonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl, and
g) a sulfonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl;

$R^8$ is independently selected from:
a) hydrogen,
b) aryl, heterocyclic, cycloalkyl, alkenyl, alkynyl, perfluoroalkyl, F, Cl, Br, $R^{10}O$—, $R^{11}S(O)_m$—, $R^{10}C(O)NR^{10}$—, CN, $NO_2$, $R^{10}{}_2N$—$C(NR^{10})$—, $R^{10}C(O)$—, $R^{10}OC(O)$—, $N_3$, —$N(R^{10})_2$, or $R^{11}OC(O)NR^{10}$—, and
c) $C_1$–$C_6$ alkyl unsubstituted or substituted by aryl, heterocyclic, cycloalkyl, alkenyl, alkynyl, perfluoroalkyl, F, Cl, Br, $R^{10}O$—, $R^{11}S(O)_m$—, $R^{10}C(O)NH$—, CN, $H_2N$—$C(NH)$—, $R^{10}C(O)$—, $R^{10}OC(O)$—, $N_3$, —$N(R^{10})_2$, or $R^{11}OC(O)NH$—;

$R^9$ is selected from:
hydrogen, $C_1$–$C_6$ alkyl, $R^{10}O$—, $R^{11}S(O)_m$—, $R^{10}C(O)NR^{10}$—, CN, $NO_2$, $N_3$, —$N(R^{10})_2$, and $R^{11}OC(O)NR^{10}$—;
provided that $R^9$ is not $R^{10}C(O)NR^{10}$— when $R^{1a}$ is alkenyl, V is hydrogen and X-Y is —$C(O)NR^{7a}$—;

$R^{10}$ is independently selected from hydrogen, $C_1$–$C_6$ alkyl, benzyl and aryl;

$R^{11}$ is independently selected from $C_1$–$C_6$ alkyl and aryl;

$R^{12}$ is independently selected from hydrogen and $C_1$–$C_6$ alkyl; $R^{13}$ is $C_1$–$C_6$ alkyl;

V is selected from:
a) aryl;
b) heterocycle; or
c) hydrogen;

W is
—$S(O)_m$—, —O—, —NHC(O)—, —C(O)NH—, —$NHSO_2$—, —$SO_2NH$—, —$N(R^{7a})$— or —$N[C(O)R^{7a}]$—;

Z is independently $H_2$ or O
m is 0, 1 or 2;

n is 0, 1, 2, 3 or 4, provided that n≠0 when V is hydrogen and W is —$S(O)_m$—;

p is 0, 1, 2, 3 or 4, provided that p≠0 when $R^9$ is not hydrogen or $C_1$–$C_6$ lower alkyl;

r is 0 or 1;

s is 4 or 5;and t is 0, 1 or 2, provided that t=0 when V is hydrogen;

or the pharmaceutically acceptable salts thereof.

In a third embodiment of this invention, the inhibitors of farnesyl transferase are illustrated by the formula III:

wherein:
$R^{1a}$ is selected from:
a) hydrogen,
b) aryl, heterocyclic, cycloalkyl, alkenyl, alkynyl, $(R^{10})_2N$—$C(NR^{10})$—, $R^{10}C(O)$—, or $R^{10}OC(O)$—, and
c) $C_1$–$C_6$ alkyl unsubstituted or substituted by aryl, heterocyclic, cycloalkyl, alkenyl, alkynyl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;

$R^{1b}$ is independently selected from:
a) hydrogen,
b) unsubstituted or substituted aryl, cycloalkyl, alkenyl, alkynyl, $(R^{10})_2N$—$C(NR^{10})$—, $R^{10}C(O)$—, or $R^{10}OC(O)$—, and
c) $C_1$–$C_6$ alkyl unsubstituted or substituted by unsubstituted or substituted aryl, cycloalkyl, alkenyl, alkynyl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;
provided that $R^{1b}$ is not $R^{10}C(O)NR^{10}$— when $R^{1a}$ is alkenyl, V is hydrogen and X-Y is —$C(O)NR^{7a}$—;

$R^{2a}$ and $R^{2b}$ are independently selected from:
a) a side chain of a naturally occurring amino acid,
b) an oxidized form of a side chain of a naturally occurring amino acid which is:
   i) methionine sulfoxide, or
   ii) methionine sulfone,
c) substituted or unsubstituted $C_1$–$C_{20}$ alkyl, $C_2$–$C_{20}$ alkenyl, $C_3$–$C_{10}$ cycloalkyl, aryl or heterocyclic group,
   wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl; or $R^{2a}$ and $R^{2b}$ are combined to form —$(CH_2)_s$—;

$R^3$ and $R^4$ are independently selected from:
a) a side chain of a naturally occurring amino acid,
b) an oxidized form of a side chain of a naturally occurring amino acid which is:
   i) methionine sulfoxide, or
   ii) methionine sulfone, c) substituted or unsubstituted $C_1$–$C_{20}$ alkyl, $C_2$–$C_{20}$ alkenyl, $C_3$–$C_{10}$ cycloalkyl, aryl or heterocyclic group,
wherein the substituent is selected from F, Cl, Br, $NO_2$, $R^{10}O$—, $R^{11}S(O)_m$—, $R^{10}C(O)^{NR10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and d) $C_1$–$C_6$ alkyl substituted with an unsubstituted or substituted group selected from aryl, heterocycle and $C_3$–$C_{10}$ cycloalkyl; or $R^3$ and $R^4$ are combined to form —$(CH_2)_s$—;

X-Y is

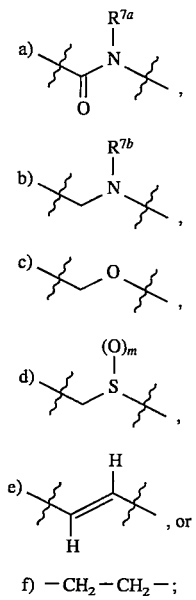

f) —$CH_2$—$CH_2$—;

$R^{7a}$ is selected from
a) hydrogen,
b) unsubstituted or substituted aryl,
c) unsubstituted or substituted heterocyclic,
d) unsubstituted or substituted cycloalkyl, and
e) $C_1$–$C_6$ alkyl substituted with hydrogen or an unsubstituted or substituted group selected from aryl, heterocyclic and cycloalkyl;

$R^{7b}$ is selected from
a) hydrogen,
b) unsubstituted or substituted aryl,
c) unsubstituted or substituted heterocyclic,
d) unsubstituted or substituted cycloalkyl,
e) $C_1$–$C_6$ alkyl substituted with hydrogen or an unsubstituted or substituted group selected from aryl, heterocyclic and cycloalkyl, f) a carbonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl, and g) a sulfonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl;

$R^8$ is independently selected from:
a) hydrogen,
b) aryl, heterocyclic, cycloalkyl, alkenyl, alkynyl, perfluoroalkyl, F, Cl, Br, $R^{10}O$—, $R^{11}S(O)_m$—, $R^{10}C(O)NR^{10}$—, CN, $NO_2$, $R^{10}{}_2N$—$C(NR^{10})$—, $R^{10}C(O)$—, $R^{10}OC(O)$—, $N_3$, —$N(R^{10})_2$, or $R^{11}C(O)NR^{10}$—, and
c) $C_1$–$C_6$ alkyl unsubstituted or substituted by aryl, heterocyclic, cycloalkyl, alkenyl, alkynyl, perfluoroalkyl, F, Cl, Br, $R^{10}O$—, $R^{11}S(O)_m$—, $R^{10}C(O)NH$—, CN, $H_2N$—$C(NH)$—, $R^{10}C(O)$—, $R^{10}OC(O)$—, $N_3$, —$N(R^{10})_2$, or $R^{11}OC(O)NH$—;

$R^9$ is selected from:
hydrogen, $C_1$–$C_6$ alkyl, $R^{10}O$—, $R^{11}S(O)_m$—, $R^{10}C(O)NR^{10}$—, CN, $NO_2$, $N_3$, —$N(R^{10})_2$, and $R^{11}OC(O)NR^{10}$—;

provided that $R^9$ is not $R^{10}C(O)NR^{10}$— when $R^{1a}$ is alkenyl, V is hydrogen and X-Y is —$C(O)NR^{7a}$—;

$R^{10}$ is independently selected from hydrogen, $C_1$–$C_6$ alkyl, benzyl and aryl;

$R^{11}$ is independently selected from $C_1$–$C_6$ alkyl and aryl;

$R^{12}$ is hydrogen or $C_1$–$C_6$ alkyl;

V is selected from:
a) aryl;
b) heterocycle; or
c) hydrogen;

W is
—$S(O)_m$—, —O—, —NHC(O)—, —C(O)NH—, —$NHSO_2$—, —$SO_2NH$—, —$N(R^{7a})$— or —$N[C(O)R^{7a}]$—;

Z is independently $H_2$ or O;

m is 0, 1 or 2;

n is 0, 1, 2, 3 or 4, provided that n≠0 when V is hydrogen and W is —$S(O)_m$—;

p is 0, 1, 2, 3 or 4, provided that p≠0 when $R^9$ is not hydrogen or $C_1$–$C_6$ lower alkyl;

q is 0, 1 or 2;

r is 0 or 1;

s is 4 or 5; and t is 0, 1 or 2, provided that t=0 when V is hydrogen;

or the pharmaceutically acceptable salts thereof.

In a fourth embodiment of this invention the prodrugs of compounds of formula III are illustrated by the formula IV:

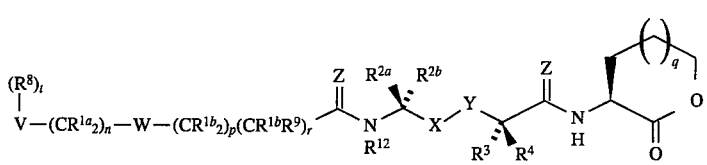

wherein:

$R^{1a}$ is selected from:
a) hydrogen,
b) aryl, heterocyclic, cycloalkyl, alkenyl, alkynyl, $(R^{10})_2N$—$C(NR^{10})$—, $R^{10}C(O)$—, or $R^{10}OC(O)$—, and c) $C_1$–$C_6$ alkyl unsubstituted or substituted by aryl, heterocyclic, cycloalkyl, alkenyl, alkynyl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}C(O)NR^{10}$—;

$R^{1b}$ is independently selected from:
a) hydrogen,
b) unsubstituted or substituted aryl, cycloalkyl, alkenyl, alkynyl, $(R^{10})_2N$—$C(NR^{10})$—, $R^{10}C(O)$—, or $R^{10}OC(O)$—, and
c) $C_1$–$C_6$ alkyl unsubstituted or substituted by unsubstituted or substituted aryl, cycloalkyl, alkenyl, alkynyl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;

provided that $R^{1b}$ is not $R^{10}C(O)NR^{10}$— when $R^{1a}$ is alkenyl, V is hydrogen and X-Y is —$C(O)NR^{7a}$—;

$R^{2a}$ and $R^{2b}$ are independently selected from:
a) a side chain of a naturally occurring amino acid,
b) an oxidized form of a side chain of a naturally occurring amino acid which is:
  i) methionine sulfoxide, or
  ii) methionine sulfone,
c) substituted or unsubstituted $C_1$–$C_{20}$ alkyl, $C_2$–$C_{20}$ alkenyl, $C_3$–$C_{10}$ cycloalkyl, aryl or heterocyclic group,
  wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl; or $R^{2a}$ and $R^{2b}$ are combined to form —$(CH_2)_s$—;

$R^3$ and $R^4$ are independently selected from:
a) a side chain of a naturally occurring amino acid,
b) an oxidized form of a side chain of a naturally occurring amino acid which is:
  i) methionine sulfoxide, or
  ii) methionine sulfone,
c) substituted or unsubstituted $C_1$–$C_{20}$ alkyl, $C_2$–$C_{20}$ alkenyl, $C_3$–$C_{10}$ cycloalkyl, aryl or heterocyclic group,
  wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl; or $R^3$ and $R^4$ are combined to form —$(CH_2)_s$—;

X-Y is a) 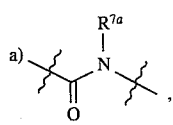

b) 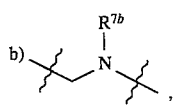

c) 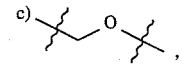

d) 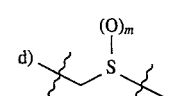

e) 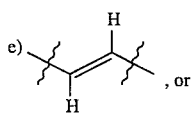, or f) 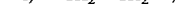;

$R^{7a}$ is selected from
a) hydrogen,
b) unsubstituted or substituted aryl,
c) unsubstituted or substituted heterocyclic,
d) unsubstituted or substituted cycloalkyl, and
e) $C_1$–$C_6$ alkyl substituted with hydrogen or an unsubstituted or substituted group selected from aryl, heterocyclic and cycloalkyl;

$R^{7b}$ is selected from
a) hydrogen,
b) unsubstituted or substituted aryl,
c) unsubstituted or substituted heterocyclic,
d) unsubstituted or substituted cycloalkyl,
e) $C_1$–$C_6$ alkyl substituted with hydrogen or an unsubstituted or substituted group selected from aryl, heterocyclic and cycloalkyl,
f) a carbonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl, and
g) a sulfonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl;

$R^8$ is independently selected from:
a) hydrogen,
b) aryl, heterocyclic, cycloalkyl, alkenyl, alkynyl, perfluoroalkyl, F, Cl, Br, $R^{10}O$—, $R^{11}S(O)_m$—, $R^{10}C(O)NR^{10}$—, CN, $NO_2$, $R^{10}{}_2N$—$C(NR^{10})$—, $R^{10}C(O)$—, $R^{10}OC(O)$—, $N_3$, —$N(R^{10})_2$, or $R^{11}OC(O)NR^{10}$—, and
c) $C_1$–$C_6$ alkyl unsubstituted or substituted by aryl, heterocyclic, cycloalkyl, alkenyl, alkynyl, perfluoroalkyl, F, Cl, Br, $R^{10}O$—, $R^{11}S(O)_m$—, $R^{10}C(O)NH$—, CN, $H_2N$—$C(NH)$—, $R^{10}C(O)$—, $R^{10}OC(O)$—, $N_3$, —$N(R^{10})_2$, or $R^{11}OC(O)NH$—;

$R^9$ is selected from:
hydrogen, $C_1$–$C_6$ alkyl, $R^{10}O$—, $R^{11}S(O)_m$—, $R^{10}C(O)NR^{10}$—, CN, $NO_2$, $N_3$, —$N(R^{10})_2$, and $R^{11}OC(O)NR^{10}$—;

provided that $R^9$ is not $R^{10}C(O)NR^{10}$— when $R^{1a}$ is alkenyl, V is hydrogen and X-Y is —$C(O)NR^{7a}$—;

$R^{10}$ is independently selected from hydrogen, $C_1$–$C_6$ alkyl, benzyl and aryl;

$R^{11}$ is independently selected from $C_1$–$C_6$ alkyl and aryl;

$R^{12}$ is hydrogen or $C_1$–$C_6$ alkyl;

V is selected from:
a) aryl;
b) heterocycle; or c) hydrogen;
W is
—S(O)$_m$—, —O—, —NHC(O)—, —C(O)NH—, —NHSO$_2$—, —SO$_2$NH—, —N(R$^{7a}$)— or —N[C(O)R$^{7a}$]—;
Z is independently H$_2$ or O
n is 0, 1 or 2;
n is 0, 1, 2, 3 or 4, provided that n≠0 when V is hydrogen and W is —S(O)$_m$—;
p is 0, 1, 2, 3 or 4, provided that p≠0 when R$^9$ is not hydrogen or C$_1$–C$_6$ lower alkyl;
q is 0, 1 or 2;
r is 0 or 1;
s is 4 or 5; and
t is 0, 1 or 2, provided that t=0 when V is hydrogen;
or the pharmaceutically acceptable salts thereof.

In a more preferred embodiment of the invention, the Ras farnesyl transferase inhibitors are illustrated by the formula I:

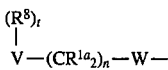

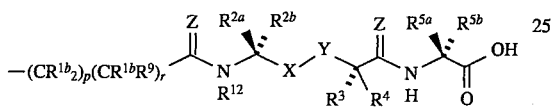    I wherein:
R$^{1a}$ is selected from:
 a) hydrogen, and
 b) C$_1$–C$_6$ alkyl;
R$^{1b}$ is independently selected from:
 a) hydrogen,
 b) unsubstituted or substituted aryl or cycloalkyl, and
 c) C$_1$–C$_6$ alkyl unsubstituted or substituted by unsubstituted or substituted aryl, cycloalkyl, alkenyl, R$^{10}$O— or —N(R$^{10}$)$_2$;
R$^{2a}$ is selected from:
 a) a side chain of a naturally occurring amino acid, wherein the amino acid is selected from alanine, leucine, isoleucine and valine;
 b) substituted or unsubstituted C$_1$–C$_{10}$ alkyl, C$_2$–C$_{10}$ alkenyl, C$_3$–C$_{10}$ cycloalkyl, aryl or heterocyclic group,
  wherein the substituent is selected from F, Cl, Br, NO$_2$, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, R$^{11}$OC(O)NR$^{10}$— and C$_1$–C$_{20}$ alkyl, and
 c) C$_1$–C$_6$ alkyl substituted with an unsubstituted or substituted group selected from aryl, heterocycle and C$_3$–C$_{10}$ cycloalkyl; and
R$^{2b}$ is selected from hydrogen and C$_1$–C$_6$ alkyl; or
 R$^{2a}$ and R$^{2b}$ are combined to form —CH$_2$)$_s$—;
R$^3$ and R$^4$ are independently selected from:
 a) a side chain of a naturally occurring amino acid,
 b) an oxidized form of a side chain of a naturally occurring amino acid which is:
  i) methionine sulfoxide, or
  ii) methionine sulfone,
 c) substituted or unsubstituted C$_1$–C$_{10}$ alkyl, C$_2$–C$_{10}$ alkenyl, C$_3$–C$_{10}$ cycloalkyl, aryl or heterocycle group, wherein the substituent is selected from F, Cl, Br, NO$_2$, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, R$^{11}$C(O)NR$^{10}$— and C$_1$–C$_{20}$ alkyl, and
 d) C$_1$–C$_6$ alkyl substituted with an unsubstituted or substituted group selected from aryl, heterocycle and C$_3$–C$_{10}$ cycloalkyl;
R$^{5a}$ is selected from:
 a) a side chain of a naturally occurring amino acid, wherein the amino acid is selected from methionine and glutamine,
 b) an oxidized form of a side chain of a naturally occurring amino acid which is:
  i) methionine sulfoxide, or
  ii) methionine sulfone,
 c) substituted or unsubstituted C$_1$–C$_{10}$ alkyl, C$_2$–C$_{10}$ alkenyl, C$_3$–C$_{10}$ cycloalkyl, aryl or heterocyclic group,
  wherein the substituent is selected from F, Cl, Br, NO$_2$, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, R$^{11}$OC(O)NR$^{10}$— and C$_1$–C$_{20}$ alkyl, and
 d) C$_1$–C$_6$ alkyl substituted with an unsubstituted or substituted group selected from aryl, heterocycle and C$_3$–C$_{10}$ cycloalkyl;
R$^{5b}$ is selected from:
 a) hydrogen, and
 b) C$_1$–C$_3$ alkyl; or
X-Y is

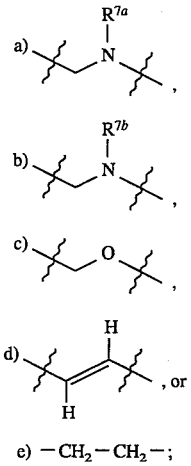

e) —CH$_2$—CH$_2$—;

R$^{7a}$ is selected from
 a) hydrogen,
 b) unsubstituted or substituted aryl,
 c) unsubstituted or substituted heterocyclic,
 d) unsubstituted or substituted cycloalkyl, and
 e) C$_1$–C$_6$ alkyl substituted with hydrogen or an unsubstituted or substituted group selected from aryl, heterocyclic and cycloalkyl;
  wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;
R$^{7b}$ is selected from
 a) hydrogen,
 b) unsubstituted or substituted aryl,
 c) unsubstituted or substituted heterocyclic,
 d) unsubstituted or substituted cycloalkyl,
 e) C$_1$–C$_6$ alkyl substituted with hydrogen or an unsubstituted or substituted group selected from aryl, heterocyclic and cycloalkyl, f) a carbonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl, and g) a sulfonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl;

wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is independently selected from:
  a) hydrogen,
  b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and
  c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^9$ is selected from:
  hydrogen, $C_1$–$C_6$ lower alkyl, $R^{10}$—, and —$N(R^{10})_2$;

$R^{10}$ is independently selected from hydrogen, $C_1$–$C_6$ alkyl, benzyl and aryl;

$R^{11}$ is independently selected from $C_1$–$C_6$ alkyl and aryl;

$R^{12}$ is hydrogen or $C_1$–$C_6$ alkyl;

V is selected from:
  a) aryl;
  b) heterocycle selected from pyrrolidinyl, imidazolyl, pyridinyl, thiazolyl, pyridonyl, 2-oxopiperidinyl, indolyl, quinolinyl, isoquinolinyl, and thienyl; and
  c) hydrogen;

W is
  —$S(O)_m$—, —O—, —NHC(O)—, —C(O)NH—, —$NHSO_2$—, —$SO_2NH$—, —$N(R^{7a})$— or —$N[C(O)R^{7a}]$—;

Z is independently $H_2$ or O;

m is 0, 1 or 2;

n is 0, 1, 2, 3 or 4, provided that n≠0 when V is hydrogen and W is —$S(O)_m$—;

p is 0, 1, 2, 3 or 4, provided that p≠0 when $R^9$ is not hydrogen or $C_1$–$C_6$ lower alkyl;

r is 0 or 1;

s is 4 or 5; and t is 0 or 1, provided that t=0 when V is hydrogen;

or the pharmaceutically acceptable salts thereof.

In a second more preferred embodiment of the invention, the prodrugs of the Ras farnesyl transferase inhibitors of the formula I are illustrated by the formula II:

$(R^8)_t$
$V—(CR^{1a}_2)_n—W—(CR^{1b}_2)_p(CR^{1b}R^9)_r—\overset{Z}{\underset{}{C}}—\underset{R^{12}}{\overset{R^{2a}\ R^{2b}}{N}}—X—Y—\underset{R^3\ R^4}{C}—\overset{Z}{\underset{}{C}}—\underset{H}{\overset{R^{5a}\ R^{5b}}{N}}—\underset{O}{\overset{}{C}}—OR^6$   II wherein:

$R^{1a}$ is selected from:
  a) hydrogen, and
  b) $C_1$–$C_6$ alkyl;

$R^{1b}$ is independently selected from:
  a) hydrogen,
  b) unsubstituted or substituted aryl or cycloalkyl, and
  c) $C_1$–$C_6$ alkyl unsubstituted or substituted by unsubstituted or substituted aryl, cycloalkyl, alkenyl, $R^{10}O$— or —$N(R^{10})_2$;

$R^{2a}$ is selected from:
  a) a side chain of a naturally occurring amino acid, wherein the amino acid is selected from alanine, leucine, isoleucine and valine;
  b) substituted or unsubstituted $C_1$–$C_{10}$ alkyl, $C_2$–$C_{10}$ alkenyl, $C_3$–$C_{10}$ cycloalkyl, aryl or heterocyclic group,
    wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
  c) $C_1$–$C_6$ alkyl substituted with an unsubstituted or substituted group selected from aryl, heterocycle and $C_3$–$C_{10}$ cycloalkyl; and $R^{2b}$ is selected from hydrogen and $C_1$–$C_6$ alkyl; or
$R^{2a}$ and $R^{2b}$ are combined to form —$(CH_2)_s$—;

$R^3$ and $R^4$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1$–$C_{10}$ alkyl, $C_2$–$C_{10}$ alkenyl, $C_3$–$C_{10}$ cycloalkyl, aryl or heterocycle group,
    wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
  d) $C_1$–$C_6$ alkyl substituted with an unsubstituted or substituted group selected from aryl, heterocycle and $C_3$–$C_{10}$ cycloalkyl;

$R^{5a}$ is selected from:
  a) a side chain of a naturally occurring amino acid, wherein the amino acid is selected from methionine and glutamine,
  b) an oxidized form of a side chain of a naturally occurring amino acid which is:
    i) methionine sulfoxide, or
    ii) methionine sulfone,
  c) substituted or unsubstituted $C_1$–$C_{10}$ alkyl, $C_2$–$C_{10}$ alkenyl, $C_3$–$C_{10}$ cycloalkyl, aryl or heterocyclic group,
    wherein the substituent is selected from F, Cl, Br, $NO_2$, $R^{10}O$—, $R^{11\ S(O)}_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
  d) $C_1$–$C_6$ alkyl substituted with an unsubstituted or substituted group selected from aryl, heterocycle and $C_3$–$C_{10}$ cycloalkyl;

$R^{5b}$ is selected from:
a) hydrogen, and
b) $C_1$-$C_3$ alkyl; or $R^6$ is
a) substituted of unsubstituted $C_1$-$C_8$ alkyl, wherein the substituent on the alkyl is selected from:
1) aryl,
2) heterocycle,
3) —N($R^{11}$)$_2$,
4) —OR$^{10}$, or
b)

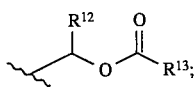

X-Y is a) 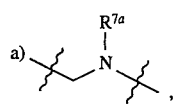

b) 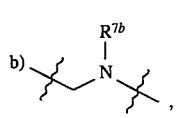

c) 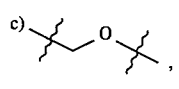

d) 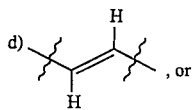, or e) —CH$_2$—CH$_2$—; 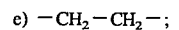

$R^7$ is selected from
a) hydrogen,
b) unsubstituted or substituted aryl,
c) unsubstituted or substituted heterocyclic,
d) unsubstituted or substituted cycloalkyl, and
e) $C_1$-$C_6$ alkyl substituted with hydrogen or an unsubstituted or substituted group selected from aryl, heterocyclic and cycloalkyl;
wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
a) hydrogen,
b) unsubstituted or substituted aryl,
c) unsubstituted or substituted heterocyclic,
d) unsubstituted or substituted cycloalkyl,
e) $C_1$-$C_6$ alkyl substituted with hydrogen or an unsubstituted or substituted group selected from aryl, heterocyclic and cycloalkyl,
f) a carbonyl group which is bonded to an unsubstituted or substituted group selected from aryl, heterocyclic, cycloalkyl and $C_1$-$C_6$ alkyl substituted with hydrogen or an unsubstituted or substituted group selected from aryl, heterocyclic and cycloalkyl, and
g) a sulfonyl group which is bonded to an unsubstituted or substituted group selected from aryl, heterocyclic, cycloalkyl and $C_1$-$C_6$ alkyl substituted with hydrogen or an unsubstituted or substituted group selected from aryl, heterocyclic and cycloalkyl;
wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is independently selected from:
a) hydrogen,
b) $C_1$-$C_6$ alkyl, $C_2$-$C_6$ alkenyl, $C_2$-$C_6$ alkynyl, $C_1$-$C_6$ perfluoroalkyl, F, Cl, $R^{10}$O—, $R^{10}$C(O)NR$^{10}$—, CN, NO$_2$, ($R^{10}$)$_2$N—C(NR$^{10}$)—, $R^{10}$C(O)—, $R^{10}$OC(O)—, —N($R^{10}$)$_2$, or $R^{11}$OC(O)NR$^{10}$—, and
c) $C_1$-$C_6$ alkyl substituted by $C_1$-$C_6$ pefluoroalkyl, $R^{10}$O—, $R^{10}$C(O)NR$^{10}$—, ($R^{10}$)$_2$N—C(NR$^{10}$)—, $R^{10}$C(O)—, $R^{10}$OC(O)—, —N($R^{10}$)$_2$, or $R^{11}$OC(O)NR$^{10}$—;

$R^9$ is selected from:
hydrogen, $C_1$-$C_6$ lower alkyl, $R^{10}$O—, and —N($R^{10}$)$_2$;

$R^{10}$ is independently selected from hydrogen, $C_1$-$C_6$ alkyl, benzyl and aryl;

$R^{11}$ is independently selected from $C_1$-$C_6$ alkyl and aryl;

$R^{12}$ is independently selected from hydrogen and $C_1$-$C_6$ alkyl;

$R^{13}$ is $C_1$-$C_6$ alkyl;

V is selected from:
a) aryl;
b) heterocycle selected from pyrrolidinyl, imidazolyl, pyridinyl, thiazolyl, pyridonyl, 2-oxopiperidinyl, indolyl, quinolinyl, isoquinolinyl, and thienyl; and
c) hydrogen;

W is
—S(O)$_m$—, —O—, —NHC(O)—, —C(O)NH—, —NHSO$_2$—, —SO$_2$NH—, —N($R^{7a}$)— or —N[C(O)R$^{7a}$]—;

Z is independently H$_2$ or O m is 0, 1 or 2;

n is 0, 1, 2, 3 or 4, provided that n≠0 when V is hydrogen and W is —S(O)$_m$—;

p is 0, 1, 2, 3 or 4, provided that p≠0 when $R^9$ is not hydrogen or $C_1$-$C_6$ lower alkyl;

r is 0 or 1;

s is 4 or 5; and t is 0 or 1, provided that t=0 when V is hydrogen;

or the pharmaceutically acceptable salts thereof.

In a third more preferred embodiment of the invention, the Ras farnesyl transferase inhibitors are illustrated by the formula III:

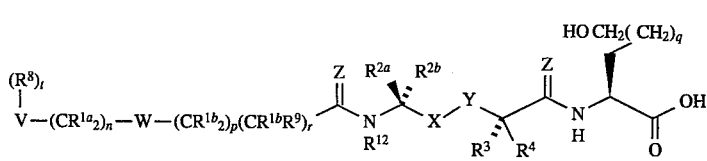

wherein:
$R^{1a}$ is selected from:
a) hydrogen, and
b) $C_1$-$C_6$ alkyl;

$R^{1b}$ are independently selected from:
 a) hydrogen,
 b) unsubstituted or substituted aryl or cycloalkyl, and
 c) $C_1$–$C_6$ alkyl unsubstituted or substituted by unsubstituted or substituted aryl, cycloalkyl, alkenyl, $R^{10}O$— or —$N(R^{10})_2$;

$R^2$ is selected from:
 a) a side chain of a naturally occurring amino acid, wherein the amino acid is selected from alanine, leucine, isoleucine and valine;
 b) substituted or unsubstituted $C_1$–$C_{10}$ alkyl, $C_2$–$C_{10}$ alkenyl, $C_3$–$C_{10}$ cycloalkyl, aryl or heterocyclic group, wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
 c) $C_1$–$C_6$ alkyl substituted with an unsubstituted or substituted group selected from aryl, heterocycle and $C_3$–$C_{10}$ cycloalkyl; and $R^{2b}$ is selected from hydrogen and $C_1$–$C_6$ alkyl; or
$R^{2a}$ and $R^{2b}$ are combined to form —$(CH_2)_s$—;

$R^3$ and $R^4$ are independently selected from:
 a) a side chain of a naturally occurring amino acid,
 b) an oxidized form of a side chain of a naturally occurring amino acid which is:
  i) methionine sulfoxide, or
  ii) methionine sulfone,
 c) substituted or unsubstituted $C_1$–$C_{10}$ alkyl, $C_2$–$C_{10}$ alkenyl, $C_3$–$C_{10}$ cycloalkyl, aryl or heterocycle group,
  wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
 d) $C_1$–$C_6$ alkyl substituted with an unsubstituted or substituted group selected from aryl, heterocycle and $C_3$–$C_{10}$ cycloalkyl:

X-Y is

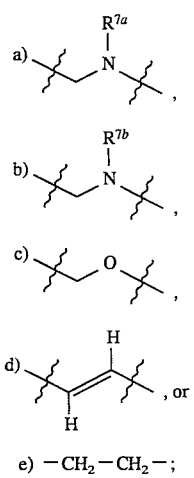

e) —$CH_2$—$CH_2$—;

$R^{7a}$ is selected from
 a) hydrogen,
 b) unsubstituted or substituted aryl,
 c) unsubstituted or substituted heterocyclic,
 d) unsubstituted or substituted cycloalkyl, and
 e) $C_1$–$C_6$ alkyl substituted with hydrogen or an unsubstituted or substituted group selected from aryl, heterocyclic and cycloalkyl;
  wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
 a) hydrogen,
 b) unsubstituted or substituted aryl,
 c) unsubstituted or substituted heterocyclic,
 d) unsubstituted or substituted cycloalkyl,
 e) $C_1$–$C_6$ alkyl substituted with hydrogen or an unsubstituted or substituted group selected from aryl, heterocyclic and cycloalkyl,
 f) a carbonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl, and
 g) a sulfonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl;
  wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is independently selected from:
 a) hydrogen,
 b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}C(O)NR^{10}$—, and
 c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^9$ is selected from:
 hydrogen, $C_1$–$C_6$ lower alkyl, $R^{10}O$—, and —$N(R^{10})_2$;

$R^{10}$ is independently selected from hydrogen, $C_1$–$C_6$ alkyl, benzyl and aryl;

$R^{11}$ is independently selected from $C_1$–$C_6$ alkyl and aryl;

$R^{12}$ is hydrogen or $C_1$–$C_6$ alkyl;

V is selected from:
 a) aryl;
 b) heterocycle selected from pyrrolidinyl, imidazolyl, pyridinyl, thiazolyl, pyridonyl, 2-oxopiperidinyl, indolyl, quinolinyl, isoquinolinyl, and thienyl; and
 c) hydrogen;

W is
 —$S(O)_m$—, —O—, —NHC(O)—, —C(O)NH—, —$NHSO_2$—, —$SO_2NH$—, —$N(R^{7a})$— or —$N[C(O)R^{7a}]$—;

Z is independently $H_2$ or O;

m is 0, 1 or 2;

n is 0, 1, 2, 3 or 4, provided that n≠0 when V is hydrogen and W is —$S(O)_m$—;

p is 0, 1, 2, 3 or 4, provided that p≠0 when $R^9$ is not hydrogen or $C_1$–$C_6$ lower alkyl;

q is 0, 1 or 2;

r is 0 or 1;

s is 4 or 5; and t is 0 or 1, provided that t=0 when V is hydrogen;

or the pharmaceutically acceptable salts thereof.

In a fourth more preferred embodiment of the invention, the prodrugs of the Ras farnesyl transferase inhibitors of the formula III are illustrated by the formula IV:

$$(R^8)_t\text{—}V\text{—}(CR^{1a}_2)_n\text{—}W\text{—}(CR^{1b}_2)_p(CR^{1b}R^9)_r\text{—}\underset{R^{12}}{\overset{Z}{C}}\text{—}N\text{—}\underset{R^{2a}}{\overset{R^{2b}}{C}}\text{—}X\text{—}Y\text{—}\underset{R^3}{\overset{R^4}{C}}\text{—}\overset{Z}{C}\text{—}NH\text{—}CH(CH_2)_q\text{—}C(O)O\quad \text{IV}$$

wherein:

$R^{1a}$ is selected from:
 a) hydrogen, and
 b) $C_1$–$C_6$ alkyl;

$R^{1b}$ are independently selected from:
 a) hydrogen,
 b) unsubstituted or substituted aryl or cycloalkyl, and
 c) $C_1$–$C_6$ alkyl unsubstituted or substituted by unsubstituted or substituted aryl, cycloalkyl, alkenyl, $R^{10}O$—, or —$N(R^{10})_2$;

$R^{2a}$ is selected from:
 a) a side chain of a naturally occurring amino acid, wherein the amino acid is selected from alanine, leucine, isoleucine and valine;
 b) substituted or unsubstituted $C_1$–$C_{10}$ alkyl, $C_2$–$C_{10}$ alkenyl, $C_3$–$C_{10}$ cycloalkyl, aryl or heterocyclic group,
  wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
 c) $C_1$–$C_6$ alkyl substituted with an unsubstituted or substituted group selected from aryl, heterocycle and $C_3$–$C_{10}$ cycloalkyl; and $R^{2b}$ is selected from hydrogen and $C_1$–$C_6$ alkyl; or $R^{2a}$ and $R^{2b}$ are combined to form —$(CH_2)_s$—;

$R^3$ and $R^4$ are independently selected from:
 a) a side chain of a naturally occurring amino acid,
 b) an oxidized form of a side chain of a naturally occurring amino acid which is:
  i) methionine sulfoxide, or
  ii) methionine sulfone,
 c) substituted or unsubstituted $C_1$–$C_{10}$ alkyl, $C_2$–$C_{10}$ alkenyl, $C_3$–$C_{10}$ cycloalkyl, aryl or heterocycle group,
  wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
 d) $C_1$–$C_6$ alkyl substituted with an unsubstituted or substituted group selected from aryl, heterocycle and $C_3$–$C_{10}$ cycloalkyl;

X-Y is a) $\overset{R^{7a}}{\underset{|}{N}}$ (methylene-N-methylene), b) $\overset{R^{7b}}{\underset{|}{N}}$ , c) methylene-O-methylene, d) methylene-CH=CH-methylene (with H's shown), or e) —$CH_2$—$CH_2$—;

$R^{7a}$ is selected from
 a) hydrogen,
 b) unsubstituted or substituted aryl,
 c) unsubstituted or substituted heterocyclic,
 d) unsubstituted or substituted cycloalkyl, and
 e) $C_1$–$C_6$ alkyl substituted with hydrogen or an unsubstituted or substituted group selected from aryl, heterocyclic and cycloalkyl;
  wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
 a) hydrogen,
 b) unsubstituted or substituted aryl,
 c) unsubstituted or substituted heterocyclic,
 d) unsubstituted or substituted cycloalkyl,
 e) $C_1$–$C_6$ alkyl substituted with hydrogen or an unsubstituted or substituted group selected from aryl, heterocyclic and cycloalkyl,
 f) a carbonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl, and
 g) a sulfonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl;
  wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is independently selected from:
 a) hydrogen,
 b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$; or $R^{11}C(O)NR^{10}$—, and
 c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^9$ is selected from: hydrogen, $C_1$–$C_6$ lower alkyl, $R^{10}O$—, and —$N(R^{10})_2$;

$R^{10}$ is independently selected from hydrogen, $C_1$–$C_6$ alkyl, benzyl and aryl;

$R^{11}$ is independently selected from $C_1$–$C_6$ alkyl and aryl;

$R^{12}$ is hydrogen or $C_1$–$C_6$ alkyl;

V is selected from:
 a) aryl;
 b) heterocycle selected from pyrrolidinyl, imidazolyl, pyridinyl, thiazolyl, pyridonyl, 2-oxopiperidinyl, indolyl, quinolinyl, isoquinolinyl, and thienyl; and
 c) hydrogen;

W is
—S(O)$_m$—, —O—, —NHC(O)—, —C(O)NH—, —NHSO$_2$—, —SO$_2$NH—, —N($R^{7a}$)— or —N[C(O)$R^{7a}$]—;

Z is independently $H_2$ or O;

m is 0, 1 or 2;

n is 0, 1, 2, 3 or 4, provided that n≠0 when V is hydrogen and W is —S(O)$_m$—;

p is 0, 1, 2, 3 or 4, provided that p≠0 when $R^9$ is not hydrogen or $C_1$–$C_6$ lower alkyl;

q is 0, 1 or 2;

r is 0 or 1;

s is 4 or 5; and t is 0 or 1, provided that t=0 when V is hydrogen;

or the pharmaceutically acceptable salts thereof.

The preferred compounds of this invention are as follows:

N-{2(S)-[(4-Nitrobenzylthio)acetamido]-3(S)-methylpentyl}-N-(1-naphthylmethyl)-glycyl-methionine methyl ester N-{2(S)-[(4-Nitrobenzylthio)acetamido]-3(S)-methylpentyl}-N-(1-naphthylmethyl)-glycyl-methionine N {2(S)-[(Benzylthio)acetamido]-3(S)-methylpentyl}-N-(1-naphthylmethyl)-glycyl-methionine N-{2(S)-[(Benzylthio)acetamido]-3(S)-methylpentyl}-N-(1-naphthylmethyl)-glycyl-methionine methyl ester N-{2(S)-[(Phenylthio)acetamido]-3(S)-methylpentyl}-N-(1-naphthylmethyl)-glycyl-methionine N-{2(S)-[(Phenylthio)acetamido]-3(S)-methylpentyl}-N-(1-naphthylmethyl)-glycyl-methionine methyl ester N-{2(S)-[(3-Nitrobenzylthio)acetamido]-3(S)-methylpentyl}-N-(1-naphthylmethyl)-glycyl-methionine N-{2(S)-[(3-Nitrobenzylthio)acetamido]-3(S)-methylpentyl}-N-(1-naphthylmethyl)-glycyl-methionine methyl ester N-{2(S)-[(2-Nitrobenzylthio)acetamido]-3(S)-methylpentyl}-N-(1-naphthylmethyl)-glycyl-methionine N-{2(S)-[(2-Nitrobenzylthio)acetamido]-3(S)-methylpentyl}-N-(1-naphthylmethyl)-glycyl-methionine methyl ester N-{2(S)-[(4-Cyanobenzylthio)acetamido]-3(S)-methylpentyl}-N-(1-naphthylmethyl)-glycyl-methionine N-{2(S)-[(4-Cyanobenzylthio)acetamido]-3(S)-methylpentyl}-N-(1-naphthylmethyl)-glycyl-methionine methyl ester N-{2(S)-[(4-Trifluoromethylbenzylthio)acetamido]-3(S)-methylpentyl}-N-(1-naphthylmethyl)-glycyl-methionine N-{2(S)-[(4-Trifluoromethylbenzylthio)acetamido]-3(S)-methylpentyl}-N-(1-naphthylmethyl)-glycyl-methionine methyl ester N-{2(S)-[(4-Methoxybenzylthio)acetamido]-3(S)-methylpentyl}-N-(1-naphthylmethyl)-glycyl-methionine N-{2(S)-[(4-Methoxybenzylthio)acetamido]-3(S)-methylpentyl}-N-(1-naphthylmethyl)-glycyl-methionine methyl ester N-{2(S)-[(4-Methylsulfonylbenzylthio)acetamido]-3(S)-methylpentyl}-N-(1-naphthylmethyl)-glycyl-methionine N-{2(S)-[(4-Methylsulfonylbenzylthio)acetamido]-3(S)-methylpentyl}-N-(1-naphthylmethyl)-glycyl-methionine methyl ester N-{2(S)-[(4-Phenylbenzylthio)acetamido]-3(S)-methylpentyl}-N-(1-naphthylmethyl)-glycyl-methionine N-{2(S)-[(4-Phenylbenzylthio)acetamido]-3(S)-methylpentyl}-N-(1-naphthylmethyl)-glycyl-methionine methyl ester N-{2(S)-[(4-(1-H-Tetrazol-5-yl)benzylthio)acetamido]-3(S)-methylpentyl}-N-(1-naphthylmethyl)-glycyl-methionine N-{2(S)-[(4-(1-H-Tetrazol-5-yl)benzylthio)acetamido]-3(S)-methylpentyl}-N-(1-naphthylmethyl)-glycyl-methionine methyl ester N-{2(S)-[(4-Methylbenzylthio)acetamido]-3(S)-methylpentyl}-N-(1-naphthylmethyl)-glycyl-methionine N-{2(S)-[(4-Methylbenzylthio)acetamido]-3(S)-methylpentyl}-N-(1-naphthylmethyl)-glycyl-methionine methyl ester N-{2(S)-[(8-Chloronaphth-1-ylthio)acetamido]-3(S)-methylpentyl}-N-(1-naphthylmethyl)-glycyl-methionine N-{2(S)-[(8-Chloronaphth-1-ylthio)acetamido]-3(S)-methylpentyl}-N-(1-naphthylmethyl)-glycyl-methionine methyl ester N-{2(S)-[((2-Methylindol-3-yl)thio)acetamido]-4-methylpentyl}-N-(1-naphthylmethyl)-glycyl-methionine N-{2(S)-[((2-Methylindol-3-yl)thio)acetamido]-4-methylpentyl}-N-(1-naphthylmethyl)-glycyl-methionine methyl ester N-{2(S)-[(4-Pyridylthio)acetamido]-3(S)-methylpentyl}-N-(1-naphthylmethyl)-glycyl-methionine N-{2(S)-[(4-Pyridylthio)acetamido]-3(S)-methylpentyl}-N-(1-naphthylmethyl)-glycyl-methionine methyl ester N-{2(S)-[(4-Picolinylthio)acetamido]-3(S)-methylpentyl}-N-(1-naphthylmethyl )-glycyl-methionine N-{2(S)-[(4-Picolinylthio)acetamido]-3(S)-methylpentyl}-N-(1-naphthylmethyl)-glycyl-methionine methyl ester N-{2(S)-[3-(Benzylthio)propionamido]-3(S)-methylpentyl}-N-(1-naphthylmethyl)-glycyl-methionine N-{2(S)-[(Benzyloxy)acetamido]-3(S)-methylpentyl}-N-(1-naphthylmethyl)-glycyl-methionine N-{2(S)-[(Benzyloxy)acetamido]-3(S)-methylpentyl}-N-(1-naphthylmethyl)-glycyl-methionine methyl ester N-{2(S)-[(N'-Benzylglycyl)amino]-3(S)-methylpentyl}-N-(1-naphthylmethyl)-glycyl-methionine N-{2(S)-[(N'-Benzylglycyl)amino]-3(S)-methylpentyl}-N-(1-naphthylmethyl)-glycyl-methionine methyl ester N-{2(S)-[(N'-Acetyl-N'-benzylglycyl)amino]-3(S)-methylpentyl}-N-(1-naphthylmethyl)-glycyl-methionine N-{2(S)-[(N'-Acetyl-N'-benzylglycyl)amino]-3(S)-methylpentyl}-N-(1-naphthylmethyl)-glycyl-methionine methyl ester N-{2(S)-[(N'-Benzyl-N'-t-butoxycarbonylglycyl)amino]-3(S)-methylpentyl}-N-(1-naphthylmethyl)-glycyl-methionine N-{2(S)-[(N'-Benzyl-N'-t-butoxycarbonylglycyl)amino]-3(S)-methylpentyl}-N-(1-naphthylmethyl)-glycyl-methionine methyl ester N-{2(S)-[(Benzylthio-S-oxide)acetamido]-3(S)-methylpentyl}-N-(1-naphthylmethyl)-glycyl-methionine N-{2(S)-[(Benzylthio-S-oxide)acetamido]-3(S)-methylpentyl}-N-(1-naphthylmethyl)-glycyl-methionine methyl ester N-{2(S)-[(Benzylthio-S,S-dioxide)acetamido]-3(S)-methylpentyl}-N-(1-naphthylmethyl)-glycyl-methionine N-{2(S)-[(Benzylthio-S,S-dioxide)acetamido]-3(S)-methylpentyl}-N-(1-naphthylmethyl)-glycyl-methionine methyl ester
N-{2(S)-[(Benzylthio)acetamido]-3(S)-methylpentyl}-N-(1-naphthylmethyl)-glycyl-methionine sulfone
N-{2(S)-[(Benzylthio)acetamido]-3(S)-methylpentyl}-N-(1-naphthylmethyl)-glycyl-methionine sulfone methyl ester
N-{2(S)-[(N'-4-Nitrobenzoylglycyl)amino]-3(S)-methylpentyl}-N-(1-naphthylmethyl)-glycyl-methionine
N-{2(S)-[(N'-4-Nitrobenzoylglycyl)amino]-3(S)-methylpentyl}-N-(1-naphthylmethyl)-glycyl-methionine methyl ester
N-{2(S)-[(N'-Methyl-N'-4-nitrobenzoylglycyl)amino]-4-methylpentyl}-N-(1-naphthylmethyl)-glycyl-methionine
N-{2(S)-[(N'-Methyl-N'-4-nitrobenzoylglycyl)amino]-4-methylpentyl}-N-(1-naphthylmethyl)-glycyl-methionine methyl ester
N-{2(S)-[(S-Benzyl-L-cysteinyl]-3(S)-methylpentyl}-N-(1-naphthylmethyl)-glycyl-methionine
N-{2(S)-[S-Benzyl-L-cysteinyl]-3(S)-methylpentyl}-N-(1-naphthylmethyl)-glycyl-methionine methyl ester
N-{2(S)-[S-Benzyl-D-cysteinyl]-3(S)-methylpentyl}-N-(1-naphthylmethyl)-glycyl-methionine
N-{2(S)-[S-Benzyl-D-cysteinyl]-3(S)-methylpentyl}-N-(1-naphthylmethyl)-glycyl-methionine methyl ester
3-Benzylthiopropionyl-valyl-isoleucyl-methionine
N-[2(S)-(2(S),3-Diaminopropionyl)amino-3(S)-methylpentyl]-N-(1-naphthylmethyl)glycyl-methionine
N-[2(S)-(2(S),3-Diaminopropionyl)amino-3(S)-methylpentyl]-N-(1-naphthylmethyl)glycyl-methionine methyl ester
N-[2(S)-(3-Aminopropionyl)amino-3(S)-methylpentyl]-N-(1-naphthylmethyl)glycyl-methionine
N-[2(S)-(3-Aminopropionyl)amino-3(S)-methylpentyl]-N-(1-naphthylmethyl)glycyl-methionine methyl ester
N-[2(S)-(1,1-Dimethylethoxycarbonylamino)-3(S)-methylpentyl]-N-benzylglycyl-methionine
N-[2(S)-(1,1-Dimethylethoxycarbonylamino)-3(S)-methylpentyl]-N-benzylglycyl-methionine methyl ester
N-{[1-(4-Nitrobenzylthio)acetylamino]cyclopent-1-ylmethyl}-N-(1-naphthylmethyl)-glycyl-methionine
N-{[1-(4-Nitrobenzylthio)acetylamino]cyclopent-1-ylmethyl}-N-(1-naphthylmethyl)-glycyl-methionine methyl ester
N-{2(S)-[2-(4-Nitrophenyl)ethylcarbamoylamino]-4-methylpentyl}-N-(1-naphthylmethyl)-glycyl-methionine
N-{2(S)-[2-(4-Nitrophenyl)ethylcarbamoylamino]-4-methylpentyl}-N-(1-naphthylmethyl)-glycyl-methionine methyl ester
N-{2(S)-[(3(S)-tetrahydrofuryloxy)carbonylamino]-3(S)-methylpentyl}-N-(1-naphthylmethyl)-glycyl-methionine
N-{2(S)-[(3(S)-tetrahydrofuryloxy)carbonylamino]-3(S)-methylpentyl}-N-(1-naphthylmethyl)-glycyl-methionine methyl ester
N-{2(S)-[(cis-4-benzyloxytetrahydrofur-3-yloxy)carbonylamino]-3(S)-methylpentyl}-N-(1-naphthylmethyl)-glycyl-methionine
N-{2(S)-[(cis-4-benzyloxytetrahydrofur-3-yloxy)carbonylamino]-3(S)-methylpentyl}-N-(1-naphthylmethyl)-glycyl-methionine methyl ester
N-{2(S)-[(N'-Methyl-N'-4-nitrophenylacetylglycyl)amino]-4-methylpentyl}-N-(1-naphthylmethyl)-glycyl-methionine
N-{2(S)-[(N'-Methyl-N'-4-nitrophenylacetylglycyl)amino]-4-methylpentyl}-N-(1-naphthylmethyl)-glycyl-methionine methyl ester
or the pharmaceutically acceptable salts thereof.

The most preferred compounds of the invention are:
N-{2(S)-[(4-Methoxybenzylthio)acetamido]-3(S)-methylpentyl}-N-(1-naphthylmethyl)-glycyl-methionine

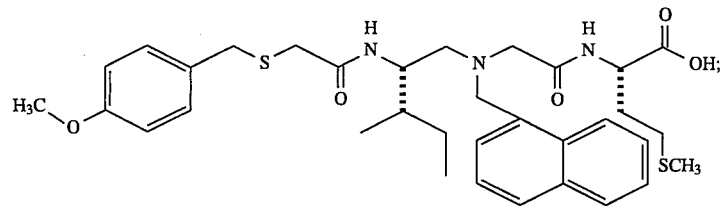

N-(2(S)-L-Glutaminylamino-3(S)-methylpentyl)-N-(1-naphthylmethyl)glycyl-methionine N-{2(S)-[(4-Methoxybenzylthio)acetamido]-3(S)-methylpentyl}-N-(1-naphthylmethyl)-glycyl-methionine methyl ester

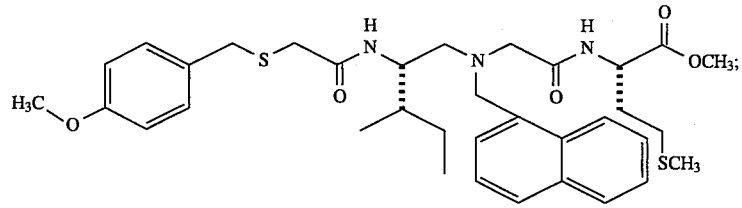

N-(2(S)-L-Glutaminylamino-3(S)-methylpentyl)-N-(1-naphthylmethyl)glycyl-methionine methyl ester
N-[2(S)-(1,1-Dimethylethoxycarbonylamino)-3S)-methylpentyl]-N-(1-naphthylmethyl)glycyl-methionine
N-[2(S)-(1,1-Dimethylethoxycarbonylamino)-3S)-methylpentyl]-N-(1-naphthylmethyl)glycyl-methionine methyl ester N-{2(S)-[(4-Cyanobenzylthio)acetamido]-3(S)-methylpentyl}-N-(1-naphthylmethyl)-glycyl-methionine

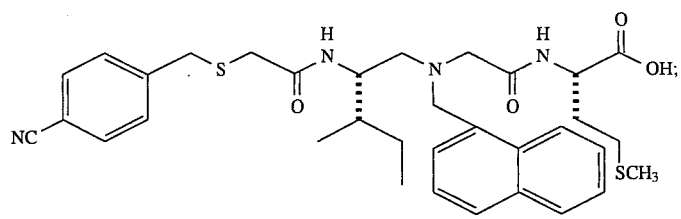

N-{2(S)-[(4-Cyanobenzylthio)acetamido]-3(S)-methylpentyl}-N-(1-naphthylmethyl)-glycyl-methionine methyl ester

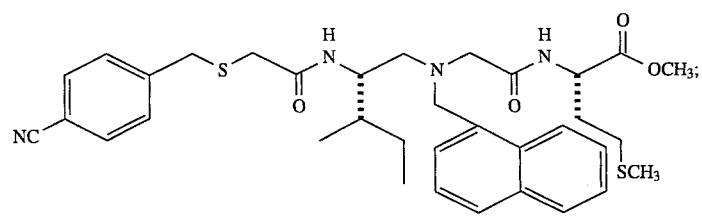

N-(2(S)-L-Glutaminylamino-3(S)-methylpentyl)-N-(1-naphthylmethyl)glycyl-methionine

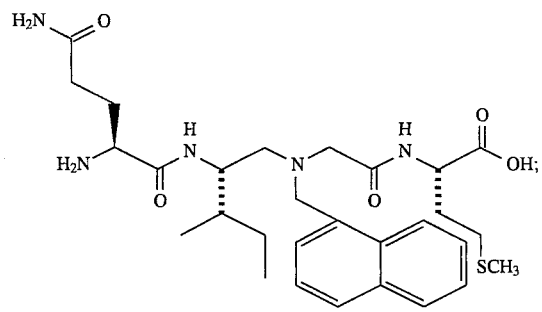

N-(2(S)-L-Glutaminylamino-3(S)-methylpentyl)-N-(1-naphthylmethyl)glycyl-methionine methyl ester

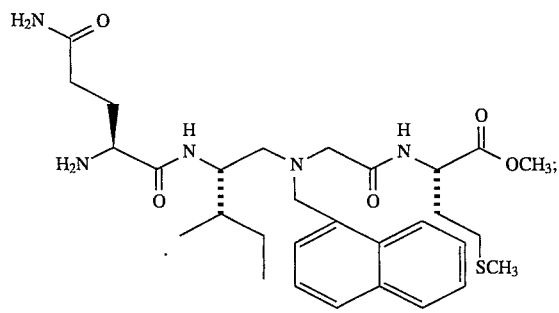

N-{2(S)-[(Benzylthio)acetamido]-3(S)-methylpentyl}-N-(1-naphthylmethyl)-glycyl-methionine sulfone

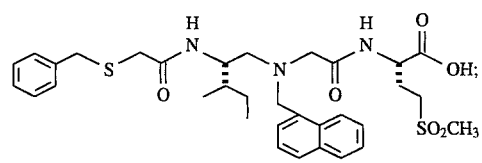

N-{2(S)-[(Benzylthio)acetamido]-3(S)-methylpentyl}-N-(1-naphthylmethyl)-glycyl-methionine sulfone methyl ester

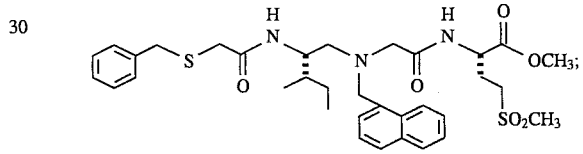

or the pharmaceutically acceptable salts thereof.

In the present invention, the amino acids which are disclosed are identified both by conventional 3 letter and single letter abbreviations as indicated below:

| Alanine | Ala | A |
| Arginine | Arg | R |
| Asparagine | Asn | N |
| Aspartic acid | Asp | D |
| Asparagine or Aspartic acid | Asx | B |
| Cysteine | Cys | C |
| Glutamine | Gln | Q |
| Glutamic acid | Glu | E |
| Glutamine or Glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The compounds of the present invention may have asymmetric centers and occur as racemates, racemic mixtures, and as individual diastereomers, with all possible isomers, including optical isomers, being included in the present invention.

As used herein, "alkyl" is intended to include both branched and straight-chain saturated aliphatic hydrocarbon groups having the specified number of carbon atoms.

As used herein, "cycloalkyl" is intended to include non-aromatic cyclic hydrocarbon groups having the specified number of carbon atoms. Examples of cycloalkyl groups include cyclopropyl, cyclobutyl, cyclopentyl, cyclohexyl and the like.

"Alkenyl" groups include those groups having the specified number of carbon atoms and having one or several double bonds. Examples of alkenyl groups include vinyl, allyl, isopropenyl, pentenyl, hexenyl, heptenyl, cyclopropenyl, cyclobutenyl, cyclopentenyl, cyclohexenyl,1-propenyl, 2-butenyl,2-methyl-2-butenyl, farnesyl, geranyl, geranylgeranyl and the like.

As used herein, "aryl" is intended to include any stable monocyclic, bicyclic or tricyclic carbon ring(s) of up to 7 members in each ring, wherein at least one ting is aromatic. Examples of aryl groups include phenyl, naphthyl, anthracenyl, biphenyl, tetrahydronaphthyl, indanyl, phenanthrenyl and the like.

When $R^{2a}$ and $R^{2b}$ and $R^3$ and $R^4$ are combined to form $-(CH_2)_s-$, cyclic moieties are formed. Examples of such cyclic moieties include, but are not limited to:

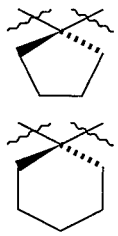

When $R^{5a}$ and $R^{5b}$ are combined to form $-(CH_2)_s-$, cyclic moieties as described hereinabove for $R^{2a}$ and $R^{2b}$ and $R^3$ and $R^4$ are formed. In addition, such cyclic moieties may optionally include a heteroatom(s). Examples of such heteroatom-containing cyclic moieties include, but are not limited to:

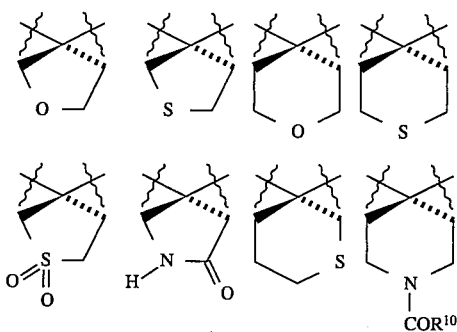

The term heterocycle or heterocyclic, as used herein, represents a stable 5- to 7-membered monocyclic or stable 8- to 11-membered bicyclic or stable 11-15 membered tricyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydro-benzothienyl, dihydrobenzothiopyranyl, dihydrobenzothio-pyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperidinyl, 2-oxopyrrolidinyl, piperidyl, piperazinyl, pyridyl, pyridyl N-oxide, pyridonyl, pyrazinyl, pyrazolidinyl, pyrazolyl, pyrimidinyl, pyrrolidinyl, pyrrolyl, quinazolinyl, quinolinyl, quinolinyl N-oxide, quinoxalinyl, tetrahydrofuryl, tetrahydroisoquinolinyl, tetrahydro-quinolinyl, thiamorpholinyl, thiamorpholinyl sulfoxide, thiazolyl, thiazolinyl, thienofuryl, thienothienyl, and thienyl.

As used herein, the terms "substituted aryl", "substituted heterocycle" and "substituted cycloalkyl" are intended to include the cyclic group which is substituted with 1 or 2 substituents selected from the group which includes but is not limited to F, Cl, Br, $NH_2$, $N(C_1-C_6 \text{ alkyl})_2$, $NO_2$, $CF_3$, $(C_1-C_6 \text{ alkyl})O-$, $-OH$, $(C_1-C_6 \text{ alkyl})S(O)_m-$, $(C_1-C_6 \text{ alkyl})C(O)NH-$, $CN$, $H_2N-C(NH)-$, $(C_1-C_6 \text{ alkyl})C(O)-$, $(C_1-C_6 \text{ alkyl})OC(O)-$, $N_3$, $(C_1-C_6 \text{ alkyl})OC(O)NH-$ and $C_1-C_{20}$ alkyl.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfonic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenyl-acetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

It is intended that the definition of any substituent or variable (e.g., $R^1$, Z, n, etc.) at a particular location in a molecule be independent of its definitions elsewhere in that molecule. Thus, $-N(R^1)_2$ represents $-NHH$, $-NHCH_3$, $-NHC_2H_5$, etc. It is understood that substituents and substitution patterns on the compounds of the instant invention can be selected by one of ordinary skill in the art to provide compounds that are chemically stable and that can be readily synthesized by techniques known in the art as well as those methods set forth below.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

The compounds of the invention can be synthesized from their constituent amino acids by conventional peptide synthesis techniques, and the additional methods described below. Standard methods of peptide synthesis are disclosed, for example, in the following works: Schroeder et at., "*The Peptides*", Vol. I, Academic Press 1965, or Bodanszky et at., "*Peptide Synthesis*", Interscience Publishers, 1966, or McOmie (ed.) "Protective Groups in Organic Chemistry", Plenum Press, 1973, or Barany et at., "The Peptides: Analysis, Synthesis, Biology"2, Chapter 1, Academic Press, 1980, or Stewart et al., "*Solid Phase Peptide Synthesis*", Second Edition, Pierce Chemical Company, 1984. The teachings of these works are hereby incorporated by reference.

Abbreviations used in the description of the chemistry and in the Examples that follow are:

| | |
|---|---|
| Ac₂O | Acetic anhydride; |
| Boc | t-Butoxycarbonyl; |
| DBU | 1,8-diazabicyclo[5.4.0]undec-7-ene; |
| DMAP | 4-Dimethylaminopyridine; |
| DME | 1,2-Dimethoxyethane; |
| DMF | Dimethylformamide; |
| EDC | 1-(3-dimethylaminopropyl)-3-ethyl-carbodiimide-hydrochloride; |
| HOBT | 1-Hydroxybenzotriazole hydrate; |
| Et₃N | Triethylamine; |
| EtOAc | Ethyl acetate; |
| FAB | Fast atom bombardment; |
| HOOBT | 3-Hydroxy-1,2,2-benzotriazin-4(3H)-one; |
| HPLC | High-performance liquid chromatography; |
| MCPBA | m-Chloroperoxybenzoic acid; |
| MsCl | Methanesulfonyl chloride; |
| NaHMDS | Sodium bis(trimethylsilyl)amide; |
| Py | Pyridine; |
| TFA | Trifluoroacetic acid; |
| THF | Tetrahydrofuran. |

Compounds of this invention are prepared by employing the reactions shown in the following Reaction Schemes A–J, in addition to other standard manipulations such as ester hydrolysis, cleavage of protecting groups, etc., as may be known in the literature or exemplified in the experimental procedures. Some key bond-forming and peptide modifying reactions are:

Reaction A. Amide bond formation and protecting group cleavage using standard solution or solid phase methodologies.

Reaction B. Preparation of a reduced peptide subunit by reductive alkylation of an amine by an aldehyde using sodium cyanoborohydride or other reducing agents.

Reaction C. Alkylation of a reduced peptide subunit with an alkyl or aralkyl halide or, alternatively, reductive alkylation of a reduced peptide subunit with an aldehyde using sodium cyanoborohydride or other reducing agents.

Reaction D. Peptide bond formation and protecting group cleavage using standard solution or solid phase methodologies.

Reaction E. Preparation of a reduced subunit by borane reduction of the amide moiety.

These reactions may be employed in a linear sequence to provide the compounds of the invention or they may be used to synthesize fragments which are subsequently joined by the alkylation reactions described in the Reaction Schemes.

REACTION SCHEME A
Reaction A. Coupling of residues to form an amide bond

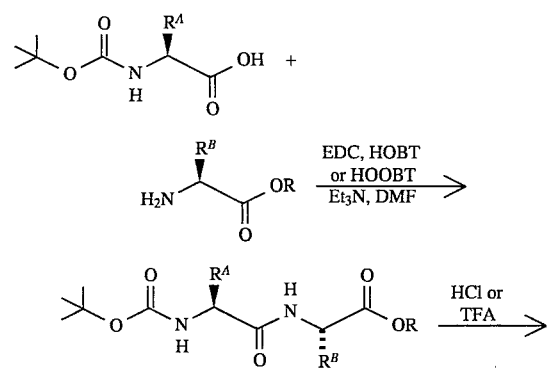

REACTION SCHEME A
Reaction A. Coupling of residues to form an amide bond

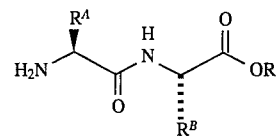

REACTION SCHEME B
Reaction B. Preparation of reduced peptide subunits by reductive alkylation

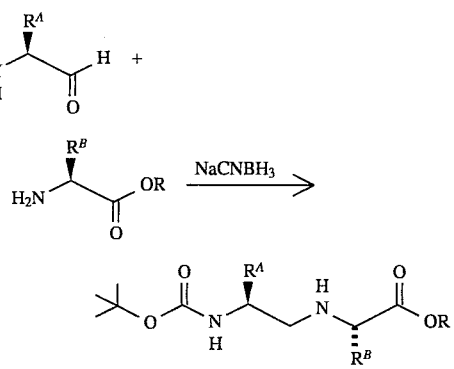

REACTION SCHEME C
Reaction C. Alkylation/reductive alkylation of reduced peptide subunits

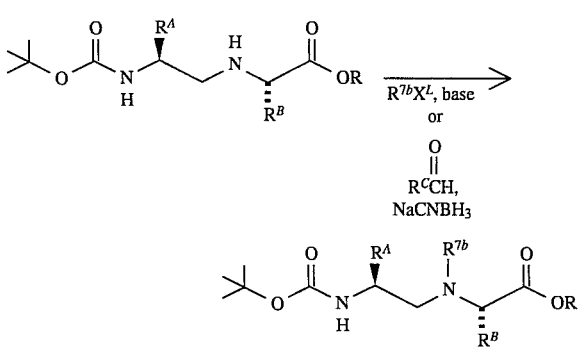

REACTION SCHEME D
Reaction D. Coupling of residues to form an amide bond

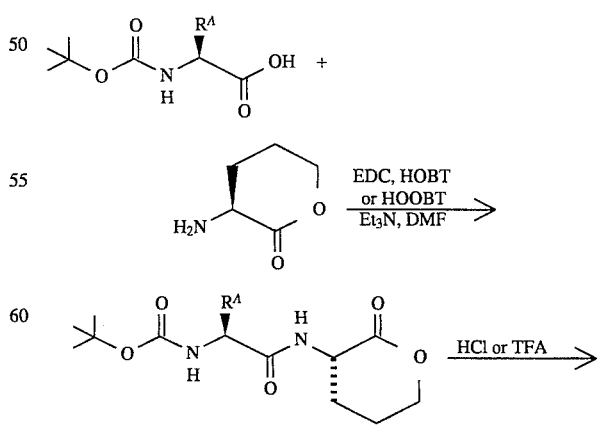

REACTION SCHEME D

Reaction D. Coupling of residues to form an amide bond

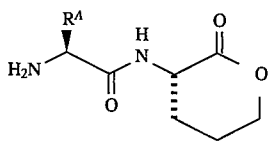

REACTION SCHEME E

Reaction E. Preparation of reduced dipeptides from peptides

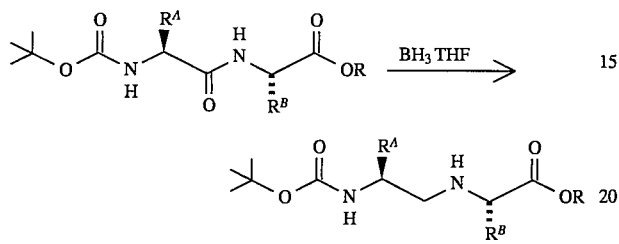

where $R^A$ and $R^B$ are $R^{2a}$, $R^{2b}$, $R^3$, $R^4$, $R^{5a}$ or $R^{5b}$ as previously defined; $X^L$ is a leaving group, e.g., $Br^-$, $I^-$ or $MsO^-$; and $R^C$ is defined such that $R^{7b}$ is generated by the reductive alkylation process.

Certain compounds of this invention wherein X-Y is an ethenylene or ethylene unit are prepared by employing the reaction sequences shown in Reaction Schemes F and G. Reaction Scheme F outlines the preparation of the alkene isosteres utilizing standard manipulations such as Weinreb amide formation, Grignard reaction, acetylation, ozonolysis, Wittig reaction, ester hydrolysis, peptide coupling reaction, mesylation, cleavage of peptide protecting groups, reductive alkylation, etc., as may be known in the literature or exemplified in the Experimental Procedure. The key reactions are: stereoselective reduction of the Boc-amino-enone to the corresponding syn amino-alcohol (Scheme F, Step B, Part 1), and stereospecific boron triflouride or zinc chloride activated organomagnesio, organo-lithio, or organo-zinc copper(l) cyanide $S_N2'$ displacement reaction (Scheme F, Step G). Through the use of optically pure N-Boc amino acids as starting material and these two key reactions, the stereo-chemistry of the final products is well defined. In Step H of Scheme F, $R^x$, which represents the amino terminus side chain substituent of the instant invention, is incorporated using coupling reaction A and $R^xCOOH$; the alkylation reaction C using $R^xCHO$ and a reducing agent; or alkylation reaction C using $R^xCH_2X^L$.

The alkane analogs are prepared in a similar manner by including an additional catalytic hydrogenation step as outlined in Reaction Scheme G.

REACTION SCHEME F

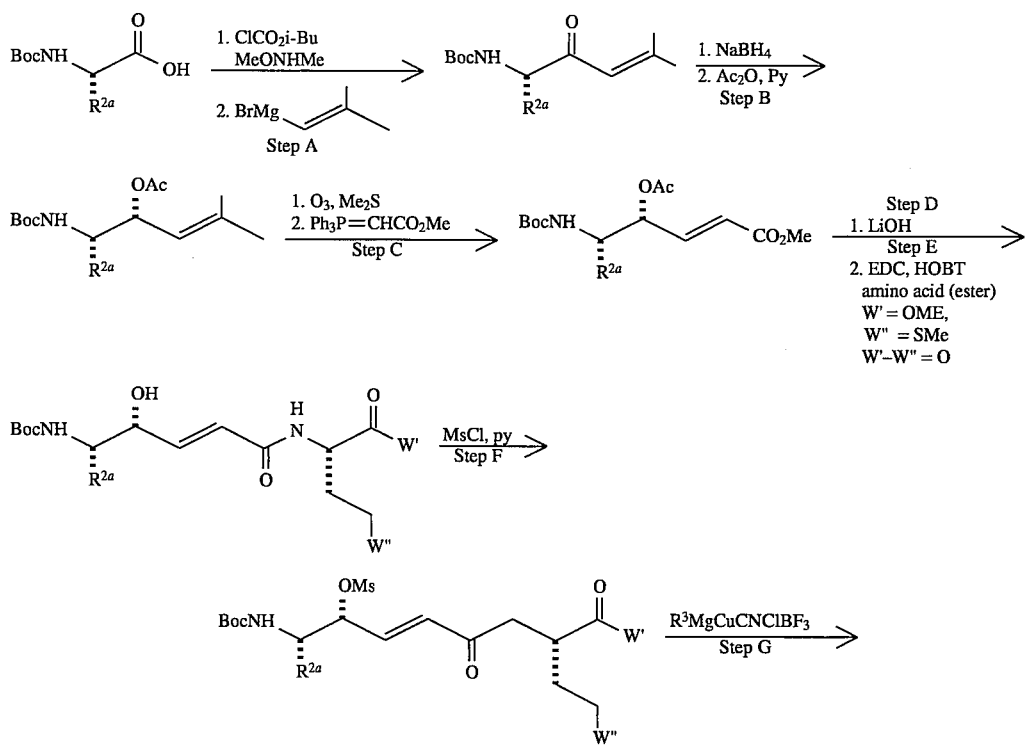

-continued
REACTION SCHEME F
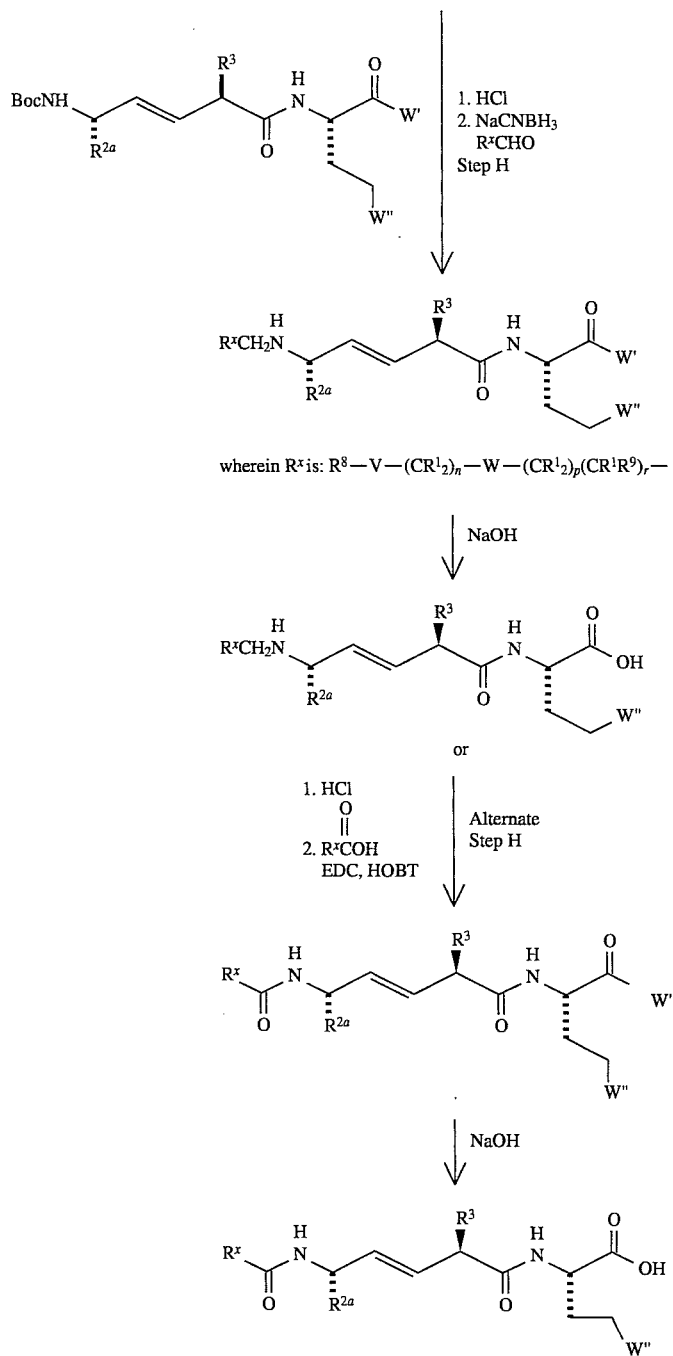
wherein $R^x$ is: $R^8-V-(CR^1{}_2)_n-W-(CR^1{}_2)_p(CR^1R^9)_r-$
REACTION SCHEME G
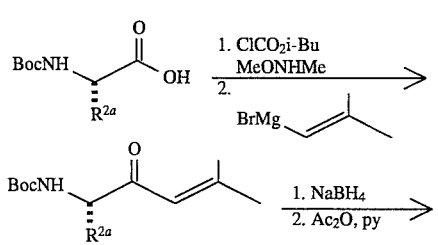
-continued
REACTION SCHEME G
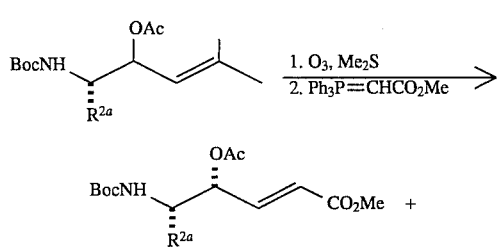

-continued
REACTION SCHEME G

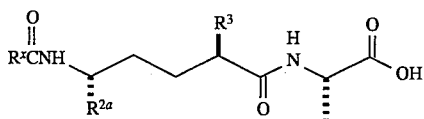

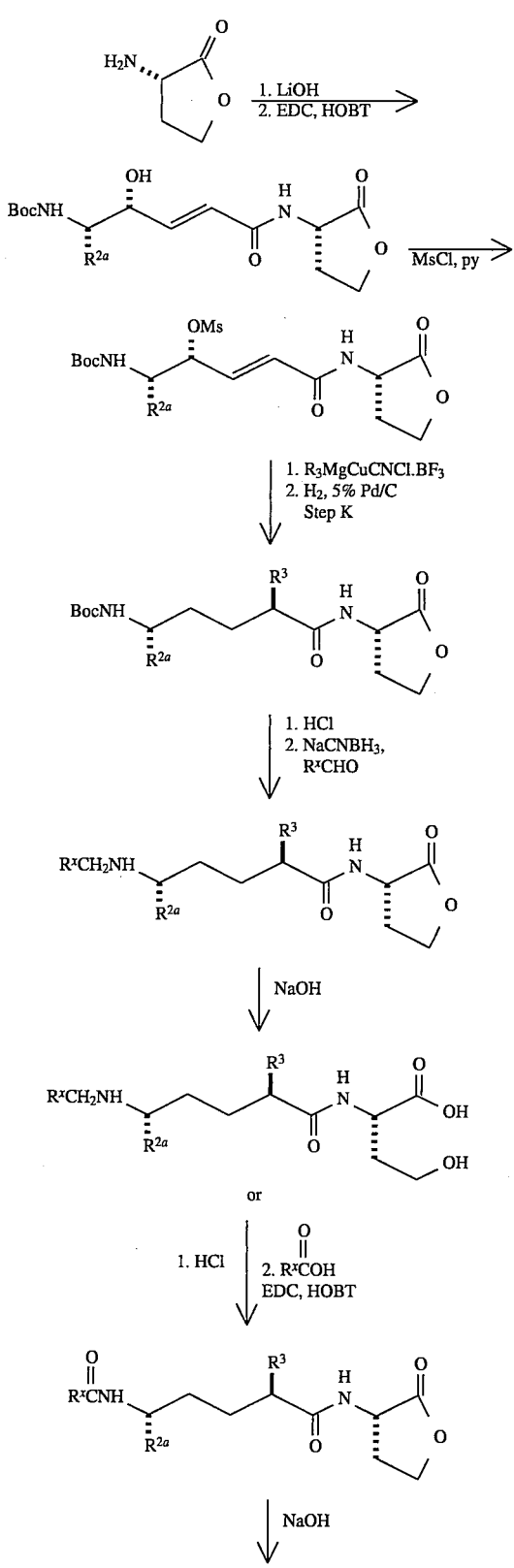

The oxa isostere compounds of this invention are prepared according to the route outlined in Scheme H. An aminoalcohol 1 is acylated with alpha-chloroacetyl chloride in the presence of trialkylamines to yield amide 2. Subsequent reaction of 2 with a deprotonation reagent (e.g., sodium hydride or potassium t-butoxide) in an ethereal solvent such as THF provides morpholinone 3. The N-Boc derivative 4 is then obtained by the treatment of 3 with BOC anhydride and DMAP (4-dimethylaminopyridine) in methylene chloride. Alkylation of 4 with $R^3X^L$, where $X^L$ is a leaving group such as $Br^-$, $I^-$ or $Cl^-$ in THF/DME (1,2-dimethoxyethane) in the presence of a suitable base, preferably NaHMDS [sodium bis(trimethylsilyl)amide], affords 5, which is retreated with NaHMDS followed by either protonation or the addition of an alkyl halide $R^4X$ to give 6a or 6b, respectively. Alternatively, 6can be prepared from 4 via an aldol condensation approach. Namely, deprotonation of 4 with NaHMDS followed by the addition of a carbonyl compound $R^yR^zCO$ gives the adduct 7. Dehydration of 7 can be effected by mesylation and subsequent elimination catalyzed by DBU (1,8-diazabicyclo[5.4.0]undec-7-ene) or the direct treatment of 7 with phosphorus oxychloride in pyridine to give olefin 8. Then, catalytic hydrogenation of 8 yields 6a. Direct hydrolysis of 6 with lithium hydrogen peroxide in aqueous THF will produce acid 9b. Sometimes, it is more efficient to carry out this conversion via a 2-step sequence, namely, hydrolysis of 6 in hydrochloric acid to afford 9a, which is then derivatized with BOC-ON or BOC anhydride to give 9b. The peptide coupling of acid 9b with either an alpha-aminolactone (e.g., homoserine lactone, etc.) or the ester of an amino acid is carried out under the conditions exemplified in the previously described references to yield derivative 10. Treatment of 10 with gaseous hydrogen chloride gives 11, which undergoes reductive alkylation in the presence of an aldehyde $R^xCHO$ (12) and a reducing agent (e.g., sodium cyanoboro-hydride); or acylation in the presence of $R^xCOOH$ (13) and a peptide coupling reagent affording the products 14a and b. Hydrolysis of compounds 14 to the corresponding hydroxy acids and acids, respectively, is accomplished by standard methods such as treatment with NaOH in alcoholic or aqueous milieux followed by careful acidifcation with dilute HCl.

5,585,359
SCHEME H
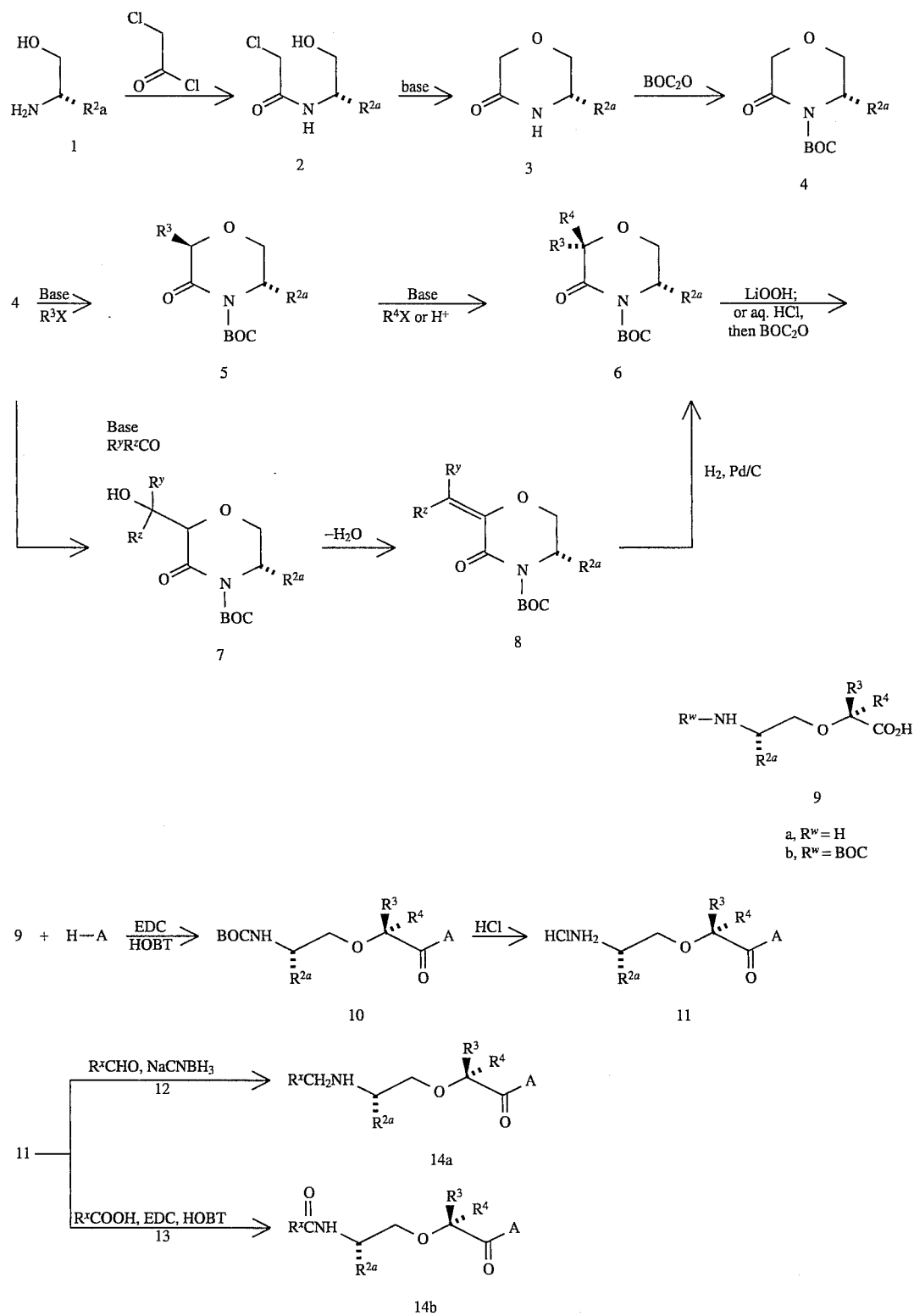

-continued
SCHEME H

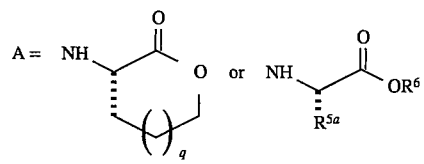

The thia, oxothia and dioxothia isostere compounds of this invention are prepared in accordance to the route depicted in Scheme I. Aminoalcohol 1 is derivatized with $BOC_2O$ to give 15. Mesylation of 15 followed by reaction with methyl alpha-mercaptoacetate in the presence of cesium carbonate gives sulfide 16. Removal of the BOC group in 16 with TFA followed by neutralization with di-isopropylethylamine leads to lactam 17. N-BOC derivative 18 is obtained via the reaction of 17 with BOC anhydride in THF catalyzed by DMAP. Sequential alkylation of 18 with the alkyl halides $R^3X$ and $R^4X$ in THF/DME using NaHDMS as the deprotonation reagent produces 19. Hydrolysis of 19 in hydrochloride to yield 20a, which is derivatized with Boc anhydride to yield 20b. The coupling of 20b with an alpha-aminolactone (e.g., homoserine lactone, etc.) or the ester of an amino acid is carried out under conventional conditions as exemplified in the previously described references to afford 21. Sulfide 21 is readily oxidized to sulfone 22 by the use of MCPBA (m-chloroperoxybenzoic acid). The N-BOC group of either 21 or 22 is readily removed by treatment with gaseous hydrogen chloride. The resultant amine hydrochloride 23 undergoes reductive alkylation in the presence of an aldehyde $R^xCHO$ (12) and a reducing agent (e.g., sodium cyanoborohydride); or acylation in the presence of $R^xCOOH$ (13) and a peptide coupling reagent to afford the products 24 and 25.

SCHEME I

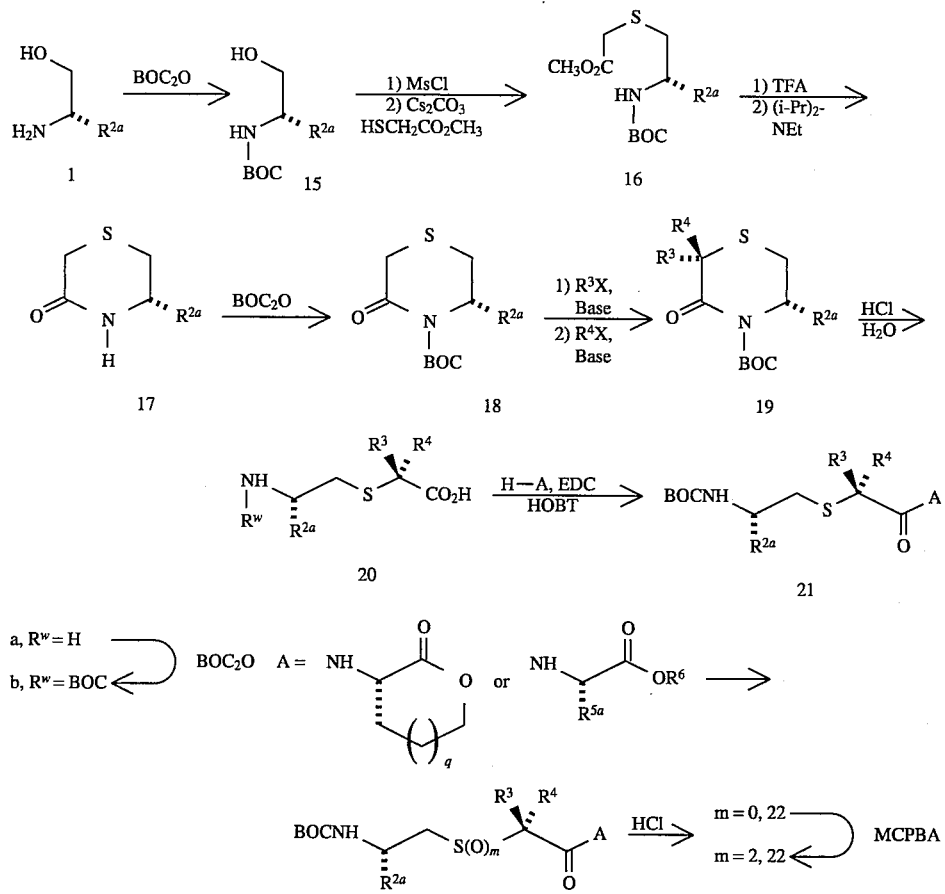

-continued
SCHEME I

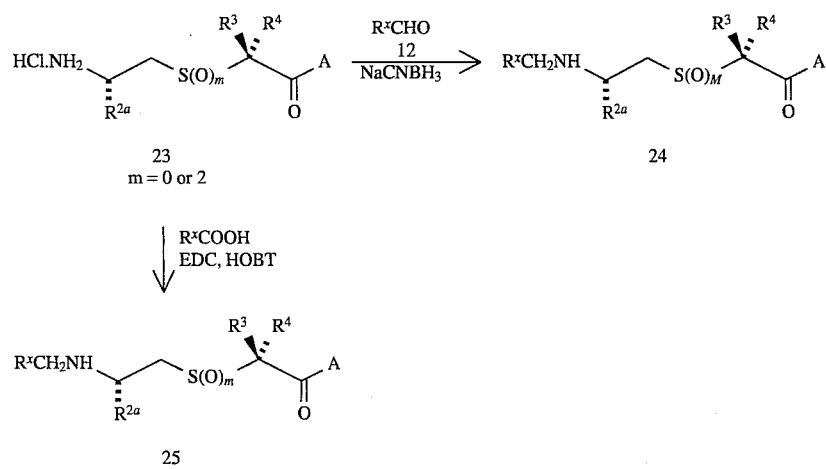

The compounds of this invention inhibit Ras farnesyl transferase which catalyzes the first step in the post-translational processing of Ras and the biosynthesis of functional Ras protein. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 20 mg/kg of body weight per day, preferably of between 0.5 mg/kg of body weight to about 10 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

The standard workup referred to in the examples refers to solvent extraction and washing the organic solution with 10% citric acid, 10% sodium bicarbonate and brine as appropriate. Solutions were dried over sodium sulfate and evaporated in vacuo on a rotary evaporator.

Example 1

Preparation of
N-{2(S)-[(4-Nitrobenzylthio)acetamido]-
3-methylpentyl}-N-(1-Naphthylmethyl)-
glycyl-methionine methyl ester Step A: Preparation of N-(2(S)-t-butoxycarbonylamino)-3-methylpentyl)glycine methyl ester Glycine methyl ester hydrochloride (23.1 g, 0.18 mol) was dissolved in methanol (700 mL) and treated with N-t-butoxycarbonyl-isoleucinal (40 g, 0.18 mol) with stirring at 0° C. Sodium cyanoborohydride (17.3 g, 0.28 mol) was added, and the pH of the mixture was adjusted to 7 with HOAc. After stirring for 3 h, aqueous saturated $NaHCO_3$ (50 mL) was added to the mixture which was then concentrated to 250 mL. The solution was partitioned between EtOAc and water. The aqueous layer was extracted with EtOAc (2×50 mL). The combined organic phase was washed with aqueous saturated $NaHCO_3$ solution, brine, and dried ($MgSO_4$). Filtration and concentration provided the title compound after purification by chromatography ($SiO_2$, EtOAc: hexane, 1:3). $^1H$ NMR (CDCl3); δ4.69 (m, 1H), 3.72 (s, 3H), 3.48–3.62 (m, 1H), 3.42 (ABq, 2H), 2.65 (d, 2H, J=6 Hz), 1.4–1.6 (m, 2H), 1.48 (s, 9H), 1.04–1.2 (m, 1H), 0.85–0.95 (m, 6H).

Step B: Preparation of N-[2(S)-t-Butoxycarbonylamino)-3-methylpentyl]-N-(1-naphthylmethyl)glycine methyl ester N-[2(S)-t-Butoxycarbonylamino)-3-methylpentyl]glycine methyl ester (2.00 g, 6.97 mmol) was dissolved in 1,2-dichloroethane (56 ml) and 3A molecular sieves were added followed by 1-naphthaldehyde (1.89 ml, 13.9 mmol) and sodium triacetoxyborohydride (6.65 g, 31.4 mmol). The mixture was stirred at ambient temperature for 16 h, and filtered through glass fiber paper and concentrated. The residue was partitioned between EtOAc and sat. $NaHCO_3$ (100 ml/25 ml). The aqueous layer was washed with EtOAc (3×50 ml). The organic layers were combined, dried with $Na_2SO_4$, filtered, and concentrated to give crude product which was purified by chromatography (silica gel 1:6 to 1:3 ethyl acetate in hexane) to provide the title compound. $^1H$ NMR ($CD_3OD$); δ8.44–8.38 (d, 1H, J=6 Hz), 7.88–7.77 (m, 2H), 7.55–7.35 (m, 4H), 6.34–6.27 (m, 1H), 4.25 (ABq, 2H), 3.66 (s, 3H), 3.40–3.23 (m, 1H), 2.95–2.85 (dd, 1H, J=6, 15 Hz), 2.68–2.57 (dd, 1H, J=6, 15 Hz), 1.57–1.46 (m, 1H), 1.43 (s, 9H), 1.34–1.18 (m, 2H), 1.06–0.85 (m, 1H), 0.85–0.71 (m, 6H).

Step C: Preparation of N-[2(S)-t-Butoxycarbonylamino)-3-methylpentyl]-N-(1-naphthylmethyl)glycine N-[2(S)-t-Butoxycarbonylamino)-3-methylpentyl]-N-(1-naphthylmethyl)glycine methyl ester (2.61 g, 6.10 mmol) was dissolved in MeOH (50 ml) and 1N NaOH (24.4 ml, 24.4 mmol) was added. The mixture was stirred at ambient temperature for 4 h and concentrated. The resulting residue was dissolved in $H_2O$ (25 ml) and neutralized with 1N HCl (24.4 ml). The aqueous layer was washed with EtOAc (3×50 ml). The organic layers were combined, dried with $Na_2SO_4$, filtered, and concentrated to provide the title compound. $^1H$ NMR ($CD_3OD$); δ8.48–8.39 (d, 1H, J=6 Hz), 8.03–7.91 (t, 2H, J=6 Hz), 7.75–7.48 (m, 4H), 5.00–4.93 (d, 1H, J=12 Hz), 4.78–4.66 (d, 1H, J=12 Hz), 3.80–3.58 (m, 3H), 3.49–3.40 (dd, 1H, J=3, 12 Hz), 3.09–2.98 (dd, 1H, J=3, 12 Hz), 1.42 (s, 9H), 1.37–1.28 (m, 2H), 1.80–1.00 (m, 1H), 0.94–0.78 (m, 6H).

Step. D: Preparation of N-[2(S)-t-Butoxycarbonylamino)-3-methylpentyl]-N-(1-naphthylmethyl)glycine-methionine methyl ester N-[2(S)-t-Butoxycarbonylamino)-3-methylpentyl]-N-(1-naphthylmethyl)glycine (2.29 g, 5.53 mmol), dissolved in DMF (20 mL), was treated with HOBT (0.822 g, 6.08 mmol), EDC (1.17 g, 6.08 mmol), and methionine methyl ester hydrochloride (1.21 g, 6.08 mmol). The pH was adjusted to 7.5 with $Et_3N$ (1.7 mL, 12 mmol) and the mixture was stirred at ambient temperature for 24 h. The mixture was concentrated, and the residue was partitioned between EtOAc (50 mL) and saturated $NaHCO_3$ solution (25 mL). The aqueous layer was extracted with EtOAc (1×30 mL). The organic layers were combined, washed with brine (1×25 mL), dried ($Na_2SO_4$), filtered, and concentrated to give crude product which was purified by chromatography (silica gel eluting with 1:3 to 1:2 ethyl acetate in hexane) to provide the title compound. 1H NMR ($CD_3OD$); δ8.36–8.29 (d, 1H, J=6 Hz), 7.93–7.86 (d, 1H, J=6 Hz), 7.85–7.80 (d, 1H, J=6 Hz), 7.61–7.39 (m, 4H), 6.60–6.52 (m, 1H), 4.32–4.06 (m, 2H), 3.90–3.69 (m, 1H), 3.65 (s, 3H), 3.27–3.14 (m, 2H), 2.93–2.70 (m, 2H), 2.19–1.78 (m, 6H), 1.63–1.30 (m, 13H), 1.19–1.05 (m, 1H), 0.95–0.81 (m, 6H).

Step E: Preparation of N-[2(S)-amino-3-methylpentyl)-N-(1-naphthylmethyl)-glycyl-methionine methyl ester hydrochloride N-[2(S)-(t-Butoxycarbonylamino)-3-methylpentyl]-N-(1-naphthylmethyl)-glycyl-methionine methyl ester (2.82 g, 5.04 mmol) was dissolved in EtOAc (50 mL) and cooled to −25° C. HCl was bubbled through the mixture until TLC (95:5 $CH_2Cl_2$:MeOH) indicated complete reaction. Nitrogen was bubbled through the mixture to remove excess HCl and the mixture was then concentrated to provide the title compound. $^1H$ NMR ($CD_3OD$); 5 8.34–8.28 (d, 1H, J=6 Hz), 8.00–7.92 (d, 2H, J=6 Hz), 7.83–7.71 (m, 1H), 7.68–7.49 (m, 3H), 4.76–4.55 (m, 4H), 3.84–3.75 (m, 2H), 3.71 (s, 3H), 3.59–3.70 (m, 1H), 3.21–3.00 (m, 2H), 2.57–2.38 (m, 3H), 2.17–2.04 (m, 4H), 1.97–1.81 (m, 1H), 1.63–1.50 (m, 1H), 1.39–1.20 (m, 1H), 1.19–1.00 (m, 1H), 0.95–0.79 (m, 6H).

Step F: Preparation of (4-nitrobenzylthio)acetic acid

4-Nitrobenzyl chloride (2.5 g, 15 mmol) was added to a solution of mercaptoacetic acid (80% in $H_2O$, 1 mL,~12 mmol) in aqueous sodium hydroxide (2.75N, 10 mL) and THF (10 mL) with stirring at 50° C. After 1 hour, the reaction was cooled to ambient temperature, diluted with water (30 mL) and extracted with $Et_2O$ to remove excess halide. The aqueous layer was distributed between EtOAc and 5% citric acid and the organic extract then washed with $H_2O$, dried ($MgSO_4$) and evaporated to give the title compound as a pale yellow solid, m.p. 101–104° C. [lit. m.p. 114° C.]. $^1$H NMR (CDCl$_3$); δ3.10 (s, 2H), 3.94 (s, 2H), 5.37 (d, 2H, J =8.7 Hz), 8.21 (d, 2H, J=8.7 Hz).

Step G: Preparation of N-{2(S)-[(4-Nitrobenzylthio)acetamido]-3(S)-methylpentyl}-N-(1-naphthylmethyl)-glycyl-methionine methyl ester (4-Nitrobenzylthio)acetic acid (68 mg, 300 μmol), dissolved in DMF (4 mL), was treated with HOBT (51 rag, 300 μmol), EDC (65 mg, 300 μmol), and N-[2(S)-amino-3-methylpentyl)-N-(1-naphthylmethyl)-glycyl-methionine methyl ester hydrochloride (133 mg, 250 μmol). The pH was adjusted to 7.5 with Et$_3$N (110 μL, 250 μmol) and the mixture was stirred at ambient temperature for 16 h. The mixture was concentrated and the residue was partitioned between EtOAc (100 mL) and H$_2$O (100 mL). The organic layer was washed with H$_2$O (2×50 mL), dried (MgSO$_4$), filtered, and concentrated to give a crude product which was purified by chromatography (silica gel, eluting with 1:1 to 1:2 hexane: EtOAc) to provide the title compound. $^1$H NMR (CDCl$_3$); δ0.89 (t, 3H, J=7.5 Hz), 0.91 (d, 3H, J=6.9 Hz), 1.02–1.19 (m, 1H), 1.37–1.6 (m, 2H), 1.67–1.79 (m, 1H), 1.85–1.98 (m, 1H), 1.95 (s, 3H), 2.0–2.1 (m, 3H), 2.74 (dd, 1H, J=3, 12 Hz), 2.86–3.01 (m, 3H), 3.21 (d, 1H, J=14 Hz), 3.29 (d, 1H, 14 Hz), 3.69 (s, 3H), 3.74 (d, 1H, J=12 Hz), 3.8 (d, 1H, J=12 Hz), 3.83–3.94 (m, 1H), 4.05 (d, 1H, J=9 Hz), 4.18 (d, 1H, J=9 Hz), 4.41–4.49 (m, 1H), 6.7 (d, 1H, J=8 Hz), 7.39–7.53 (m, 7H), 7.8–7.9 (m, 2H), 8.14–8.22 (m, 2H).

Anal. Calcd for C$_{34}$H$_{44}$N$_4$O$_6$S$_2$.0.15 EtOAc C, 60.92; H, 6.68; N, 8.21 C, 60.64; H, 6.65; N, 8.23

Example 2

N-{2(S)-[(4-Nitrobenzylthio)acetamido]-3(S)-methylpentyl}-N-(1-naphthylmethyl)-glycyl-methionine N-{2(S)-[(4-Nitrobenzylthio)acetamido]-3(S)-methylpentyl}-N-(1-naphthylmethyl)-glycyl-methionine methyl ester (from Example 1; 100 mg, 150 μmol) was dissolved in MeOH (1 mL) and 1.0N NaOH (300 μL, 300 μmol) was added. The mixture was stirred at 45° C. under argon for 45 minutes then the solution was partitioned between EtOAc (100 mL) and 5% citric acid (50 mL). The organic layer was washed with H$_2$O (2×50 mL), dried (MgSO$_4$), filtered and evaporated to give the title compound. $^1$H NMR; δ0.84 (t, 3H, J=7.5 Hz), 0.88 (d, 3H, J=7 Hz), 0.91–1.0 (m, 1H), 1.0–1.2 (m, 1H), 1.2–2.1 (m, 5H), 1.90 (s, 3H), 2.8–2.86 (m, 2H), 3.0–3.3 (m, 4H), 3.90 (s, 2H), 3.91–4.22 (m, 4H), 7.37–7.56 (m, 6H), 7.78–7.88 (m, 2H), 8.15 (d, 2H, J=8 Hz), 8.27 (d, 1H, J=8.3 Hz).

Anal. Calcd for C$_{33}$H$_{42}$N$_4$O$_6$S$_2$.0.25 CHCl$_3$.1.0 CH$_3$OH C, 57.39; H, 6.50; N, 7.82 C, 57.71; H, 6.42; N, 7.46

Example 3

The following acids were prepared according to the procedure described for Example 1, Step F or were obtained commercially:

(Benzylthio)acetic acid
(3-Nitrobenzylthio)acetic acid
(2-Nitrobenzylthio)acetic acid
(4-Cyanobenzylthio)acetic acid
(4-Trifluoromethylbenzylthio)acetic acid
(4-Methoxybenzylthio)acetic acid
(4-Methylsulfonylbenzylthio)acetic acid
(4-Phenylbenzylthio)acetic acid
(4-Methylbenzylthio)acetic acid
(8-Chloronaphth-1-ylthio)acetic acid
(2-Methylindol-3-ylthio)acetic acid
3-(Benzylthio)propionic acid
(4-Picolinylthio)acetic acid
(4-Pyridylthio)acetic acid Example 4

The following compounds were prepared using the procedure described for Example 1, Step G, but substituting the appropriate acid from Example 3 for (4-nitrobenzylthio)acetic acid, and, in some cases, substituting N-t-butoxycarbonylleucinal for N-t-butoxycarbonyl-isoleucinal in Step A in the preparation of the intermediate.

N-{2(S)-[(Benzylthio)acetamido]-3(S)-methylpentyl}-N-(1-naphthylmethyl)-glycyl-methionine methyl ester FAB mass spectrum m/z=624 (M+1).

Anal. Calcd for C$_{34}$H$_{45}$N$_3$O$_4$S$_2$.0.30 TFA.0.95 H$_2$O C, 55.70; H, 6.16; N, 5.32 C, 55.72; H, 6.17; N, 5.30

N-{2(S)-[(3-Nitrobenzylthio)acetamido]-3(S)-methylpentyl}-N-(1-naphthylmethyl)-glycyl-methionine methyl ester Anal. Calcd for C$_{34}$H$_{44}$N$_4$O$_6$S$_2$.0.2 EtOAc C, 60.88; H, 6.70; N, 8.16 C, 60.52; H, 6.63; N, 8.31

N-{2(S)-[(2-Nitrobenzylthio)acetamido]-3(S)-methylpentyl}-N-(1-naphthymethyl)-glycyl-methionine methyl ester Anal. Calcd for C$_{34}$H$_{44}$N$_4$O$_6$S$_2$.0.2 EtOAc C, 60.88; H, 6.70; N, 8.16 C, 60.44; H, 6.67; N, 8.19

N-{2(S)-[(4-Cyanobenzylthio)acetamido]-3(S)-methylpentyl}-N-(1-naphthylmethyl)-glycyl-methionine methyl ester Anal. Calcd for C$_{35}$H$_{44}$N$_4$O$_4$S$_2$.0.5 EtOAc C, 64.13; H, 6.98; N, 8.09 C, 63.85; H, 6.91; N, 8.17

N-{2(S)-[(4-Trifluoromethylbenzylthio)acetamido]-3(S)-methylpentyl}-N-(1-naphthymethyl)-glycyl-methionine methyl ester Anal. Calcd for C$_{35}$H$_{44}$F$_3$N$_3$O$_4$S$_2$.0.4 EtOAc.1.0 H$_2$O C, 58.99; H, 6.66; N, 5.64 C, 58.97; H, 6.37; N, 5.61

N-{2(S)-[(4-Methoxybenzylthio)acetamido]-3(S)-methylpentyl}-N-(1-naphthylmethyl-glycyl-methionine methyl ester Anal. Calcd for C$_{35}$H$_{47}$N$_3$O$_5$S$_2$.0.6 EtOAc.0.35 H$_2$O C, 62.99; H, 7.42; N, 5.89 C, 62.64; H, 7.17; N, 6.29

N-{2(S)-[(4-Methylsulfonylbenzylthio)acetamido]-3(S)-methylpentyl}-N-(1-naphthylmethyl)-glycyl-methionine methyl ester Anal. Calcd for C$_{35}$H$_{47}$N$_3$O$_6$S$_3$ C, 59.89; H, 6.75; N, 5.99 C, 60.14; H, 6.90; N, 5.96

N-{2(S)-[(4-Phenylbenzylthio)acetamido]-3(S)-methylpentyl}-N-(1-naphthylmethyl)-glycyl-methionine methyl ester FAB mass spectrum m/z=700 (M+1).

N-{2(S)-[(4-Methylbenzylthio)acetamido]-3(S)-methylpentyl}-N-(1-naphthylmethyl)glycyl-methionine methyl ester FAB mass spectrum m/z=638 (M+1).

N-{2(S)-[(8-Chloronaphth-1-ylthio)acetamido]-3(S)-methylpentyl}-N-(1-naphthylmethyl)-glycyl-methionine methyl ester Anal. Calcd for $C_{37}H_{44}ClN_3O_4S_2 \cdot 0.5$ EtOAc C, 63.43; H, 6.55; N, 5.69 C, 63.33; H, 6.35; N, 6.07

N-{2(S)-[((2-Methylindol-3-yl)thio)acetamido]-4-methylpentyl}-N-(1-naphthylmethyl)-glycyl-methionine methyl ester Anal. Calcd for $C_{36}H_{46}N_4O_4S_2 \cdot 0.35$ EtOAc C, 64.74; H, 7.09; N, 8.08 C, 64.73; H, 6.93; N, 8.32

N-{2(S)-[(4-Pyridylthio)acetamido]-3(S)-methylpentyl}-N-(1-naphthylmethyl)-glycyl-methionine methyl ester Anal. Calcd for $C_{32}H_{42}N_4O_4S_2 \cdot 2.0$ TFA. 0.75 $H_2O$ C, 50.72; H, 5.38; N, 6.57 C, 50.84; H, 5.28; N, 6.56

N-{2(S)-[(4-Picolinylthio)acetamido]-3(S)-methylpentyl}-N-(1-naphthylmethyl)-glycyl-methionine methyl ester Anal. Calcd for $C_{33}H_{44}N_4O_4S_2 \cdot 2.0$ TFA.0.75 $H_2O$ C, 51.29; H, 5.53; N, 6.47 C, 51.27; H, 5.35; N, 6.70

N-{2(S)-[3-(Benzylthio)propionamido]-3(S)-methylpentyl}-N-(1-naphthymethyl)-glycyl-methionine methyl ester $^1$H NMR (CDCl$_3$); δ0.84 (t, 3H), 0.88 (d, 3H), 1.08 (m, 1H), 1.40 (m, 2H), 1.66–2.0 (m, 7H), 2.33 (m, 2H), 2.7 (m, 3H), 2.99 (dd, 1H), 3.21 (s, 2H), 3.68 (s, 3H), 3.7 (m, 3H), 4.4 (m, 1H), 6.33 (d, 1H), 7.2–7.4 (m, 10H), 7.7–7.9 (m, 4H), 8.19 (m, 1H).

Example 5

N-{2(S)-[(Phenylthio)acetamido]-3(S)-methylpentyl}-N-(1-naphthylmethyl)-glycyl-methionine methyl ester To solution of N-(2(S)-amino-3(S)-methylpentyl)-N-(1-naphthymethyl)-glycyl-methionine methyl ester hydrochloride (125 mg, 0.23 mmol) and Et$_3$N (65.5 µL, 0.47 mmol) in THF (2.5 mL) at room temperature was added bromo acetylbromide (24 µL, 0.28 mmol). After 10 minutes, thiophenol (29 µL, 0.28 mmol) and Et$_3$N (49 µL, 0.35 mmol) were added and the mixture was stirred for 4 hours. The solution was poured into saturated aqueous NaHCO$_3$, extracted with EtOAc (×3), washed with brine, dried (MgSO$_4$) and evaporated. Purification of the residue by column chromatography (silica gel; hexane/EtOAc 3:2) gave the title compound as an oil.

FAB mass spectrum m/z=610 (M+1).

Anal. Calcd for $C_{33}H_{43}N_3O_4S_2 \cdot 0.5$ TFA. 1.15 $H_2O$ C, 53.94; H, 5.88; N, 5.24 C, 53.93; H, 5.91; N, 5.11

Example 6

N-{2(S)-[(4-(1-H-Tetrazol-5-yl)benzylthio)acetamido]-3(S)-methylpentyl}-N-(1-naphthylmethyl)-glycyl-methionine methyl ester Step A: Preparation of [4-(1H-tetrazol-5-yl)benzylthio] acetic acid (4-Cyanobenzylthio)acetic acid (from Example 3; 207 mg, 1 mmol) was added to a stirred solution of trimethylsilylazide (400 µL, 3 mmol) and dibutyltin oxide (25 mg, 100 µmol) in toluene (0.5 mL) at 110° C. After 6 hours, the reaction was quenched with MeOH (1 mL) and evaporated. The residue was purified by flash chromatography (silica gel; 1000:100:3 to 1000:100:13 CHCl$_3$/MeOH/HOAc) to give the title compound. R$_f$ (silica; 1000:100:6 CHCl$_3$/MeOH/HOAc)=0.2 compared to the nitrile starting material of R$_f$=0.67. $^1$H NMR (d$^6$ DMSO); δ3.15 (s, 2H), 3.88 (s, 2H), 7.51 (d, 2H, J=8.1 Hz), 7.99 (d, 2H, J=8.1 Hz). FAB mass spectrum m/z=251 (M+1).

Step B: N-{2(S)-[(4-(1-H-Tetrazol-5-yl)benzylthio)acetamido]-3(S)-methylpentyl}-N-(1-naphthylmethyl)-glycyl-methionine methyl ester Following the procedure described for Example 1, Step G, [4-(1H-tetrazol-5-yl)benzylthio]acetic acid was coupled with N-(2(S)-amino-3(S)-methylpentyl)-N-(1-naphthylmethyl)-glycyl-methionine methyl ester hydrochloride to give the title compound.

Anal. Calcd for $C_{35}H_{45}N_7O_4S_2 \cdot 0.8$ TFA C, 51.67; H, 5.26; N, 10.93 C, 51.66; H, 5.26; N, 10.84

Example 7

N-{2(S)-[(Benzyloxy)acetamido]-3(S)-methylpentyl}-N-(1-naphthylmethyl)-glycyl-methionine methyl ester The title compound was prepared from N-[2(S)-amino-3-methylpentyl)-N-(1-naphthylmethyl)-glycyl-methionine methyl ester hydrochloride (Example 1, Step E) and benzyloxyacetyl chloride (Aldrich) under standard conditions.

FAB mass spectrum m/z=608 (M+1).

Example 8

N-{2(S)-[(N'-Benzyl-N'-t-butoxycarbonylglycyl)amino]-3(S)-methylpentyl}-N-(1-naphthymethyl)-glycyl-methionine methyl ester Step A Preparation of N-benzyl-N-t-butoxycarbonylglycine N-Benzylglycine ethyl ester hydrochloride was converted to N-benzyl-N-t-butoxycarbonylglycine ethyl ester using di-t-butyl dicarbonate under standard conditions. The ethyl ester was saponified using sodium hydroxide in methanol to give the title compound.

Step B: Preparation of N-{2(S)-[(N'-benzyl-N'-t-butoxycarbonylglycyl)amino]-3(S)-methylpentyl}-N-(1-naphthylmethyl)-glycyl-methionine methyl ester The glycine derivative prepared in Step A was converted to the title compound using the method of Example 1, Step G.

Anal. Calcd for $C_{39}H_{54}N_4O_6S \cdot 0.5$ $H_2O$ C, 65.42; H, 7.74; N, 7.83 C, 65.31; H, 7.33; N, 8.01

Example 9

N-{2(S)-[(N'-Benzylglycyl)amino]-3(S)-methylpentyl}-N-(1-naphthymethyl)-glycyl-methionine methyl ester The t-butoxycarbonyl group of N-{2(S)-[(N'-benzyl-N'-t-butoxycarbonylglycyl)amino]-3(S)-methylpentyl}-N-(1-naphthymethyl)-glycyl-methionine methyl ester, Example 8, was cleaved using the method of Example 1, Step E to provide the title compound.

Anal. Calcd for $C_{34}H_{46}N_4O_4S.2.0$ HCl.0.75 $H_2O$ C, 58.90; H, 7.20; N, 8.08 C, 59.07; H, 6.88; N, 7.87

Example 10

N-{2(S)-[(N'-Acetyl-N'-benzylglycyl)amino]-3(S)-methylpentyl}-N-(1-naphthymethyl)-glycyl-methionine methyl ester A solution of N-{2(S)-[(N'-benzylglycyl)amino]-3(S)-methylpentyl}-N-(1-naphthymethyl)-glycyl-methionine methyl ester from Example 9 (200 mg, 0.3 mmol) was dissolved in $CH_2Cl_2$ (4 mL). Acetic anhydride (0.11 mL) and N,N-diisopropylethylamine (0.31 mL) were added and the mixture was stirred for 48 hours. The mixture was concentrated and partitioned between ethyl acetate and saturated sodium bicarbonate solution. The organic layer was dried and evaporated to give a residue which was purified by silica gel chromatography (1–3% MeOH in $CH_2Cl_2$) to give the title compound.

Anal. Calcd for $C_{36}H_{48}N_4O_5S.0.5$ $H_2O$ C, 65.72; H, 7.51; N, 8.52 C, 6:5.87; H, 7.23; N, 8.69

Example 11

N-{2(S)-[(Benzylthio-S-oxide)acetamido]-3(S)-methylpentyl}-N-(1-naphthymethyl)-glycyl-methionine methyl ester Step A: Preparation of (benzylthio)acetic acid S-oxide Benzylthioacetic acid was convened to the known title compound (Lindstrom and Mark, U.S. Pat. No. 4,637,833) by oxidation with sodium periodate in methanol.

Step B: N-{2(S)-[(Benzylthio-S-oxide)acetamido]-3(S)-methylpentyl}-N-(1-naphthymethyl)-glycyl-methionine methyl ester The sulfoxide derivative from Step A was converted to the title compound using the method of Example 1, Step G.

FAB mass spectrum m/z=640 (M+1).

Example 12

N-{2(S)-[(Benzylthio-S,S-dioxide)acetamido]-3(S)-methylpentyl}-N-(1-naphthymethyl)-glycyl-methionine methyl ester Step A: preparation of (benzylthio)acetic acid S,S-dioxide Benzylthioacetic acid was converted to the known title compound (Lindstrom and Mark, U.S. Pat. No. 4,637,833) by oxidation with Oxone in methanol.

Step B: N-{2(S)-[(Benzylthio-S,S-dioxide)acetamidol-3(S)-methylpentyl}-N-(1-naphthylmethyl)-glycyl-methionine methyl ester The sulfone derivative from Step A was converted to the title compound using the method of Example 1, Step G.

FAB mass spectrum m/z=656 (M+1).

Example 13

N-{2(S)-[(Benzylthio)acetamido]-3(S)-methylpentyl}-N-(1-naphthymethyl)-glycyl-methionine methyl ester Using the method of Example 1, but substituting methionine sulfone and benzylthioacetic acid as appropriate, the title compound was prepared.

FAB mass spectrum m/z=656 (M+1).

Example 14

N-{2(S)-[(N'-4-Nitrobenzoylglycyl)amino]-3(S)-methylpentyl}-N-(1-naphthylmethyl}-glycyl-methionine methyl ester Following the procedure described for Example 1, Step G, but substituting (4-nitrobenzylthio)acetic acid with N-(4-nitrobenzoyl)glycine (Aldrich) the title compound was obtained.

Anal. Calcd for $C_{34}H_{43}N_5O_7S.0.8$ $H_2O$ C, 60.03; H, 6.61; N, 10.30 C, 59.99; H, 6.32; N, 10.28

Example 15

N-{2(S)-[(N'-Methyl-N'-4-nitrobenzoylglycyl)amino]-4-methylpentyl}-N-(1-naphthymethyl)-glycyl-methionine methyl ester Following the procedure described for Example 1, but substituting (4-nitrobenzylthio)acetic acid with N-(4-nitrobenzoyl)sarcosine (A. Morgan et al, *J. Med. Chem.*, 34:2126 (1991)) and N-t-butoxycarbonylleucinal for N-t-butoxycarbonylisoleucinal the title compound was obtained.

Anal. Calcd for $C_{35}H_{45}N_5O_7S.0.35$ EtOAc C, 61.51; H, 6.78; N, 9.86 C, 61.13; H, 6.69; N, 10.11

Example 16

N-{2(S)-[S-Benzyl-L-cysteinyl]-3(S)-methylpentyl}-N-(1-naphthymethyl)-glycyl-methionine methyl ester S-Benzyl-N-t-butoxycarbonyl-L-cysteine (Bacheme) was coupled with N-[2(S)-amino-3-methylpentyl]-N-(1-naphthylmethyl)-glycyl-methionine methyl ester hydrochloride according to the procedure described for Example 1, Step G. The product thus obtained was deprotected using TFA in $CH_2Cl_2$ to give the title compound.

FAB mass spectrum m/z=653 (M+1).

Anal. Calcd for $C_{35}H_{48}N_4O_4S_2.2.8$ TFA.0.1 $H_2O$ C, 50.07; H, 5.28; N, 5.75 C, 50.07; H, 5.32; N, 5.98

Example 17

N-{2(S)-[S-benzyl-D-cysteinyl]-3(S)-methylpentyl}-N-(1-naphthymethyl)-glycyl-methionine methyl ester S-Benzyl-N-t-butoxycarbonyl-D-cysteine (Bachem) was coupled with N-[2(S)-amino-3-methylpentyl]-N-(1-naphthylmethyl)-glycyl-methionine methyl ester hydrochloride according to the procedure described for Example 1, Step G. The product thus obtained was deprotected using TFA in $CH_2Cl_2$ to give the title compound.

FAB mass spectrum m/z=653 (M+1).

Anal. Calcd for $C_{35}H_{48}N_4O_4S_2 \cdot 2.3$ TFA$\cdot 0.5$ H$_2$O C, 51.47; H, 5.60; N, 6.06 C, 51.49; H, 5.57; N, 6.33

Example 18

The following compounds were prepared from the corresponding esters (Examples 3–17) using the procedure described for Example 2.

N-{2(S)-[(Benzylthio)acetamido]-3(S)-methylpentyl}-N-(1-naphthymethyl)-glycyl-methionine FAB mass spectrum m/z=610 (M+1).

Anal. Calcd for $C_{33}H_{43}N_3O_4S_2 \cdot 0.05$ TFA$\cdot 1.05$ H$_2$O C, 56.32; H, 6.22; N, 5.61 C, 56.32; H, 5.99; N, 6.01

N-{2(S)-[(Phenylthio)acetamido]-3(S)-methylpentyl}-N-(1-naphthymethyl)-glycyl-methionine FAB mass spectrum m/z=596 (M+1).

Anal. Calcd for $C_{32}H_{41}N_3O_4S_2 \cdot 0.25$ TFA$\cdot 0.75$ H$_2$O C, 55.11; H, 5.87; N, 5.59 C, 55.14; H, 5.86; N, 5.46

N-{2(S)-[(3-Nitrobenzylthio)acetamido]-3(S)-methylpentyl}-N-(1-naphthymethyl)-glycyl-methionine Anal. Calcd for $C_{33}H_{42}N_4O_6S_2 \cdot 1.2$ H$_2$O$\cdot 0.5$ EtOAc C, 58.34; H, 6.77; N, 7.78 C, 52.34; H, 6.54; N, 7.51

N-{2(S)-[(2-Nitrobenzylthio)acetamido]-3(S)-methylpentyl}-N-(1-naphthymethyl)-glycyl-methionine Anal. Calcd for $C_{33}H_{42}N_4O_6S_2 \cdot 1.2$ H$_2$O$\cdot 0.5$ EtOAc C, 58.34; H, 6.77; N, 7.78 C, 58.34; H, 6.51; N, 7.63

N-{2(S)-[(4-Cyanobenzylthio)acetamido]-3(S)-methylpentyl}-N-(1-naphthymethyl)-glycyl-methionine Anal. Calcd for $C_{34}H_{42}N_4O_4S_2 \cdot 0.3$ CHCl$_3$ C, 61.42; H, 6.36; N, 8.35 C, 61.73; H, 6.31; N, 8.41

N-{2(S)-[(4-Trifluoromethylbenzylthio)acetamido]-3(S)-methylpentyl}-N-(1-naphthymethyl)-glycyl-methionine Anal. Calcd for $C_{34}H_{42}F_3N_3O_4S_2 \cdot 0.5$ EtOAc C, 59.89; H, 6.42; N, 5.82 C, 59.60; H, 6.25; N, 5.82

N-{2(S)-[(4-Methoxybenzylthio)acetamido]-3(S)-methylpentyl}-N-(1-naphthylmethyl)-glycyl-methionine Anal. Calcd for $C_{34}H_{45}N_3O_5S_2 \cdot 0.5$ EtOAc C, 63.22; H, 7.22; N, 6.14 C, 63.22; H, 7.03; N, 6.19

N-{2(S)-[(4-Methylsulfonylbenzylthio)acetamido]-3(S)-methylpentyl}-N-(1-naphthymethyl)-glycyl-methionine Anal. Calcd for $C_{34}H_{45}N_3O_6S_3 \cdot 0.3$ H$_2$O C, 58.89; H, 6.63; N, 6.06 C, 58.85; H, 6.64; N, 6.00

N-{2(S)-[(4-Phenylbenzylthio)acetamido]-3(S)-methylpentyl}-N-(1-naphthymethyl)-glycyl-methionine Anal. Calcd for $C_{39}H_{47}N_3O_4S_2 \cdot 0.5$ TFA$\cdot 0.5$ H$_2$O C, 58.25; H, 5.76; N, 4.85 C, 58.26; H, 5.67; N, 4.87

N-{2(S)-[(4-Methylbenzylthio)acetamido]-3(S)-methylpentyl}-N-(1-naphthymethyl)-glycyl-methionine Anal. Calcd for $C_{34}H_{45}N_3O_4S_2 \cdot 0.25$ H$_2$O C, 64.98; H, 7.30; N, 6.69 C, 64.95; H, 7.17; N, 6.66

N-{2(S)-[(8-Chloronaphth-1-ylthio)acetamido]-3(S)-methylpentyl}-N-(1-naphthymethyl)-glycyl-methionine Anal. Calcd for $C_{36}H_{42}ClN_3O_4S_2 \cdot 1.0$ EtOAc$\cdot 1.0$ H$_2$O C, 61.08; H, 6.66; N, 5.34 C, 61.09; H, 6.94; N, 5.38

N-{2(S)-[((2-Methylindol-3-yl)thio)acetamido]-4-methylpentyl}-N-(1-naphthymethyl)-glycyl-methionine Anal. Calcd for $C_{35}H_{44}N_4O_4S_2 \cdot 0.5$ EtOAc$\cdot 0.5$ H$_2$O C, 63.30; H, 7.04; N, 7.98 C, 63.17; H, 6.77; N, 7.98

N-{2(S)-[(4-Pyridylthio)acetamido]-3(S)-methylpentyl}-N-(1-naphthymethyl)-glycyl-methionine FAB mass spectrum m/z=579 (M+1).

N-{2(S)-[(4-Picolinylthio)acetamido]-3(S)-methylpentyl}-N-(1-naphthymethyl)-glycyl-methionine Anal. Calcd for $C_{32}H_{42}N_4O_4S_2 \cdot 2.0$ TFA$\cdot 1.7$ H$_2$O C, 49.72; H, 5.49; N, 6.44 C, 49.51; H, 5.10; N, 6.57

N-{2(S)-[3-(Benzylthio)propionamido]-3(S)-methylpentyl}-N-(1-naphthymethyl)-glycyl-methionine FAB mass spectrum m/z=624 (M+1).

Anal. Calcd for $C_{34}H_{45}N_3O_4S_2 \cdot 1.0$TFA C, 58.60; H, 6.28; N, 5.69 C, 58.63; H, 6.29; N, 5.92

N-{2(S)-[(Benzyloxy)acetamido]-3(S)-methylpentyl}-N-(1-naphthymethyl)-glycyl-methionine FAB mass spectrum m/z=594 (M+1).

N-{2(S)-[(N'-Benzylglycyl)amino]-3(S)-methylpentyl}-N-(1-naphthylmethyl)-glycyl-methionine Anal. Calcd for $C_{33}H_{44}N_4O_4S \cdot 2.0$ TFA$\cdot 1.0$ H$_2$O C, 52.97; H, 5.77; N, 6.68 C, 52.91; H, 5.61; N, 6.63

N-{2(S)-[(N'-Acetyl-N'-benzylglycyl)amino]-3(S)-methylpentyl}-N-(1-naphthymethyl)-glycyl-methionine Anal. Calcd for $C_{35}H_{46}N_4O_5S \cdot 1.0$ TFA$\cdot 0.75$ H$_2$O C, 58.29; H, 6.41; N, 7.35 C, 58.13; H, 6.19; N, 7.68

N-{2(S)-[(Benzylthio-S-oxide)acetamido]-3(S)-methylpentyl}-N-(1-naphthymethyl)-glycyl-methionine FAB mass spectrum m/z=626 (M+1).

N-{2(S)-[(Benzylthio-S,S-dioxide)acetamido]-3(S)-methylpentyl}-N-(1-naphthymethyl)-glycyl-methionine FAB mass spectrum m/z=642 (M+1).

N-{2(S)-[(Benzylthio)acetamido]-3(S)-methylpentyl}-N-(1-naphthylmethyl)-glycyl-methionine sulfone The $^1$H-NMR was consistent with the titled structure.

N-{2(S)-[(N'-4-Nitrobenzoylglycyl)amino]-
3(S)-methylpentyl}-N-(1-naphthymethyl)-
glycyl-methionine Anal. Calcd for $C_{33}H_{41}N_5O_7S.0.5\ H_2O$ C, 59.98; H, 6.41; N, 10.60 C, 59.84; H, 6.31; N, 10.22

N-{2(S)-[(N'-Methyl-N'-4-nitrobenzoylglycyl)
amino]-4-methylpentyl}-N-(1-naphthylpentyl)-
glycyl-methionine Anal. Calcd for $C_{34}H_{43}N_5O_7S.0.6$ EtOAc.0.5 $H_2O$ C, 60.08; H, 6.76; N, 9.62 C, 60.06; H, 6.45; N, 9.60

N-{2(S)-[(S-Benzyl-L-cysteinyl]-3(S)-methylpentyl}-
N-(1-naphthymethyl)-glycyl-methionine FAB mass spectrum m/z=639 (M+1).
Anal. Calcd for $C_{34}H_{46}N_4O_4S_2.2.4$ TFA.0.7 $H_2O$ C, 50.37; H, 5.43; N, 6.06 C, 50.34; H, 5.39; N, 6.14

N-{2(S)-[S-Benzyl-D-cysteinyl]-3(S)-methylpentyl}-
N-(1-naphthymethyl)-glycyl-methionine FAB mass spectrum m/z=639 (M+1).
Anal. Calcd for $C_{34}H_{46}N_4O_4S_2.2.9$ TFA.0.5 $H_2O$ C, 48.85; H, 5.14; N, 5.73 C, 48.82; H, 5.12; N, 5.84

Example 19

3-Benzylthiopropionyl-valyl-isoleucyl-methionine

This compound was synthesized using standard techniques of solution phase peptide synthesis starting from methionine methyl ester and other commercially available materials.
Anal. Calcd for $C_{26}H_{41}N_3O_5S_2$ C, 57.86; H, 7.66; N, 7.79 C, 57.54; H, 7.58; N, 7.81

Example 20

N-{2(S)-[(4-(1-H-Tetrazol-5-yl)benzylthio)
acetamido]-3(S)-methylpentyl}-N-(1-naphthymethyl)-
glycyl-methionine sodium salt The sodium salt of N-{2(S)-[(4-(1-H-tetrazol-5-yl)benzylthio)acetamido]-3(S)-methylpentyl}-N-(1-naphthylmethyl)-glycyl-methionine was prepared from the corresponding methyl ester (2.1 mg) in 200 μL of MeOH treated with 150 μL of 0.1N NaOH and the solution dilute to 1 mL for assay.

Example 21

N-{2(S)-[(N'-Benzyl-N'-t-butoxycarbonylglycyl)
amino]-3(S)-methylpentyl}-N-(1-naphthymethyl)-
glycyl-methionine sodium salt The sodium salt of N-{2(S)-[(N'-benzyl-N'-t-butoxycarbonylglycyl)amino]-3(S)-methylpentyl}-N-(1-naphthylmethyl)glycyl-methionine was prepared in situ by hydrolysis of the corresponding methyl ester (2.2 mg) in 0.3 mL of MeOH with 6.2 μL of 1N NaOH to give a 10 mM solution for assay.

Example 22

N-{[1-(4-Nitrobenzylthio)acetylamino]cyclopent-
1-ylmethyl}-N-(1-naphthymethyl)-glycyl-methionine
methyl ester Step A: Preparation of 1-tert-(butyloxy)carbonylaminocyclopentane-1-carboxaldehyde The title compound was prepared by a Swern oxidation (3 equivalents of pyridine-sulfurtrioxide complex and excess triethyl amine in $DMSO/CH_2Cl_2$) of BOC protected 1-amino-1-hydroxymethyl-cyclopentane (Aldrich).
Step B: Preparation of N-{[1-(4-Nitrobenzylthio)acetylamino]cyclopent-1-ylmethyl}-N-(1-naphthylmethyl)-glycyl-methionine methyl ester Following the procedure described in Example 1, but substituting the 1-tert-(butyloxy)carbonylaminocyclopentane-1-carboxaldehyde from Step A for N-t-butoxycarbonylisoleucinal provided the title compound. $C_{34}H_{42}N_4O_6S_2$ FAB mass spectrum, m/e 667 (M+1).

Example 23

N-{[1-(4-Nitrobenzylthio)acetylamino]cyclopent-
1-ylmethyl}-N-(1-naphthymethyl)-glycyl-methionine Following the procedure described in Example 2, but substituting the ester from Example 22 provided the title compound. $C_{33}H_{40}N_4O_6S_2$ FAB mass spectrum; m/e 653 (M+1).

Example 24

N-{2(S)-[2-(4-Nitrophenyl)ethylcarbamoylamino]-
4-methylpentyl}-N-(1-naphthymethyl)-
glycyl-methionine methyl ester 2-(4-Nitrophenyl)ethylamine (0.5 mmol) and p-nitrophenylchloroformate (0.5 mmol) were allowed to react in the presence of triethylamine (1 mmol) in 5 ml of DMF to provide 2-(4-nitrophenyl)ethyl isocyanate. Without isolation, the isocyanate was mixed with N-(2(S)-amino-4-methylpentyl)-N-(1-naphthylmethyl)-glycyl-methionine methyl ester dihydrochloride (0.4 mmol) and triethylamine (1 mmol) in 4 mL of DMF to provide the title compound. $C_{34}H_{45}N_5O_6S.0.15$ hexane
Anal. Calcd for $C_{26}H_{41}N_3O_5S_2$ C, 63.05; H, 7.14; N, 10.54 C, 63.10; H, 7.09; N, 10.16

Example 25

N-{2(S)-[2-(4-Nitrophenyl)ethylcarbamoylamino]-
4-methylpentyl}-N-(1-naphthymethyl)-
glycyl-methionine Following the procedure described in Example 2, but substituting the ester from Example 24 provided the title compound. $C_{33}H_{43}N_5O_6S.EtOAc$ C, 61.22; H, 7.08; N, 9.65 C, 61.32; H, 6.72; N, 9.73

Example 26

N-{2(S)-[(3(S)-tetrahydrofuryloxy)carbonylamino]-
3(S)-methylpentyl}-N-(1-naphthymethyl)-
glycyl-methionine methyl ester The succinimidyl carbonate of 3(S)-hydroxytetrahydrofuran, was prepared as described by Ghosh, et al., (*J. Med. Chem.* 1993, 36:292). The carbonate (46 mg, 0.20 mmol)

and N-(2(S)-amino-3(S)-methylpentyl)-N-(1-naphthymethyl)-glycyl-methionine methyl ester dihydrochloride (106 mg, 0.20 mmol) were dissolved in 3 mL of methylene chloride and 56 μL (0.40 mmol) of triethylamine was added. After stirring overnight the mixture was diluted with ethyl acetate and washed successively with 10% citric acid, 10% sodium bicarbonate and brine. After drying, the solvent was evaporated and the residue was chromatographed on silica (1.5% methanol in methylene chloride) to provide N-{2(S)-[(3(S)-tetrahydrofuryloxy)-carbonylamino]-3(S)-methylpentyl}-N-(1-naphthymethyl)-glycyl-methionine methyl ester.

Example 27

N-{2(S)-[(3(S)-tetrahydrofuryloxy)carbonylamino]-3(S)-methylpentyl}-N-(1-naphthymethyl)-glycyl-methionine Following the procedure described in Example 2, but substituting the ester from Example 26 provided the title compound. $C_{29}H_{41}N_3O_6S \cdot CF_3CO_2H \cdot 2.1\ H_2O$ C, 52.32; H, 6.54; N, 5.91 C, 51.85; H, 6.01; N, 6.34

Example 28

N-{2(S)-[(cis-4-benzyloxytetrahydrofur-3-yloxy)carbonylamino]-3(S)-methylpentyl}-N-(1-naphthymethyl)-glycyl-methionine methyl ester Following the procedure described in Example 26, but substituting the succinimidyl carbonate of racemic cis-4-benzyloxy-3-hydroxytetrahydrofuran (prepared as described by Vacca, et al., (Can. Pat. 2,084,800, Jun. 17, 1993)) provided a 1:1 mixture of diastereomers of N-{2(S)-[(cis-4-benzyloxytetrahydrofur-3-yloxy)carbonylamino]-3(S)-methylpentyl}-N-(1-naphthymethyl)-glycyl-methionine methyl ester which were inseparable by HPLC chromatography.

Example 29

N-{2(S)-[(cis-4-benzyloxytetrahydrofur-3-yloxy)carbonylamino]-3(S)-methylpentyl}-N-(1-naphthymethyl)-glycyl-methionine Following the procedure described in Example 2, but substituting the ester from Example 28 provided the title compound as a mixture of diastereomers that were separated by reverse phase HPLC chromatography. Isomers A and B, $C_{36}H_{47}N_3O_7S$ gave FAB MS m/e=666 (M+1).

Example 30

N-{2(S)-(t-butoxycarbonylamino)-3(S)-methylpentyl}-N-(1-naphthymethyl)-glycyl-methionine Using the procedure described in Example 2, N-[2(S)-(t-butoxycarbonylamino)-3(S)-methylpentyl]-N-(1-naphthymethyl)-glycyl-methionine methyl ester (prepared in Example 1, Step B, was converted to the title compound. $C_{29}H_{43}N_3O_5S \cdot 0.4\ H_2O$ C, 62.99; H, 7.98; N, 7.60 C, 62.98; H, 7.83; N, 7.62

Example 31

In vitro inhibition of ras farnesyl transferase

Assays of farnesyl-protein transferase. Partially purified bovine FPTase and Ras peptides (Ras-CVLS, Ras-CVIM and RAS-CAIL) were prepared as described by Schaber et at., *J. Biol. Chem.* 265:14701–14704 (1990), Pompliano, et al., *Biochemistry* 31:3800 (1992) and Gibbs et al., *PNAS U.S.A.* 86:6630–6634 (1989). Bovine FPTase was assayed in a volume of 100 μl containing 100 mM N-(2-hydroxy ethyl) piperazine-N'-(2-ethane sulfonic acid) (HEPES), pH 7.4, 5 mM $MgCl_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 μg/ml FPTase at 31° C. for 60 min. Reactions were initiated with FPTase and stopped with 1 ml of 1.0 M HCL in ethanol. Precipitates were collected onto filter-mats using a TomTec Mach II cell harvestor, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 μM $ZnCl_2$ and 100 nM Ras-CVIM were added to the reaction mixture. Reactions were performed for 30 min., stopped with 100 μl of 30% (v/v) trichloroacetic acid (TCA) in ethanol and processed as described above for the bovine enzyme.

The compounds of the instant invention were tested for inhibitory activity against human FPTase by the assay described above and were found to have $IC_{50}$ of <10 μM.

Example 32

In vivo ras farnesylation assay

The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM $MgCl_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13–259 (Furth, M. E. et at., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 33

In vivo growth inhibition assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of $1\times10^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the :final concentration used in the assay). The cells are fed twice weekly with 0.5 ml of medium A containing 0.1% methanol or the concentration of the instant compound. Photomicrographs are taken 16 days after the cultures are seeded and comparisons are made.

What is claimed is:

1. A compound which inhibits Ras farnesyl-transferase having the formula I:

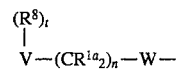
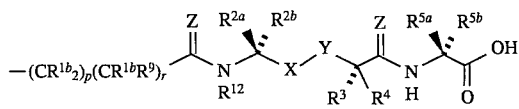

wherein:

$R^{1a}$ is selected from:
a) hydrogen,
b) aryl, heterocyclic, cycloalkyl, alkenyl, alkynyl, $(R^{10})_2N-C(NR^{10})-$, $R^{10}C(O)-$, or $R^{10}OC(O)-$, and
c) $C_1-C_6$ alkyl unsubstituted or substituted by aryl, heterocyclic, cycloalkyl, alkenyl, alkynyl, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $N_3$, $-N(R^{10})_2$, or $R^{11}OC(O)NR^{10}-$;

$R^{1b}$ is independently selected from:
a) hydrogen,
b) unsubstituted or substituted aryl, cycloalkyl, alkenyl, alkynyl, $(R^{10})_2N-C(NR^{10})-$, $R^{10}C(O)-$, or $R^{10}OC(O)-$, and
c) $C_1-C_6$ alkyl unsubstituted or substituted by unsubstituted or substituted aryl, cycloalkyl, alkenyl, alkynyl, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $N_3$, $-N(R^{10})_2$, or $R^{11}OC(O)NR^{10}-$;

provided that $R^{1b}$ is not $R^{10}C(O)NR^{10}-$ when $R^{1a}$ is alkenyl, V is hydrogen and X-Y is $-C(O)NR^{7a}-$;

$R^{2a}$ and $R^{2b}$ are independently selected from:
a) a side chain of a naturally occurring amino acid,
b) an oxidized form of a side chain of a naturally occuring amino acid which is:
i) methionine sulfoxide, or
ii) methionine sulfone,
c) substituted or unsubstituted $C_1-C_{20}$ alkyl, $C_2-C_{20}$ alkenyl, $C_3-C_{10}$ cycloalkyl, aryl or heterocyclic group,
wherein the substituent is selected from F, Cl, Br, $NO_2$, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $N_3$, $-N(R^{10})_2$, $R^{11}OC(O)NR^{10}-$ and $C_1-C_{20}$ alkyl, and
d) $C_1-C_6$ alkyl substituted with an unsubstituted or substituted group selected from aryl, heterocycle and $C_3-C_{10}$ cycloalkyl; or $R^{2a}$ and $R^{2b}$ are combined to form $-(CH_2)_s-$;

$R^3$ and $R^4$ are independently selected from:
a) a side chain of a naturally occurring amino acid,
b) an oxidized formed of a side chain of a naturally occurring amino acid which is:
i) methionine sulfoxide, or
ii) methionine sulfone,
c) substituted or unsubstituted $C_1-C_{20}$ alkyl, $C_2-C_{20}$ alkenyl, $C_3-C_{10}$ cycloalkyl, aryl or heterocyclic group,
wherein the substituent is selected from F, Cl, Br, $NO_2$, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $N_3$, $-N(R^{10})_2$, $R^{11}OC(O)NR^{10}-$ and $C_1-C_{20}$ alkyl, and
d) $C_1-C_6$ alkyl substituted with an unsubstituted or substituted group selected from aryl, heterocycle and $C_3-C_{10}$ cycloalkyl;or $R^3$ and $R^4$ are combined to form $-(CH_2)_s-$;

$R^5$ and $R^{5b}$ independently selected from:
a) a side chain of a naturally occurring amino acid,
b) an oxidized form of a side chain of a naturally occuring amino acid which is:
i) methionine sulfoxide, or
ii) methionine sulfone,
c) substituted or unsubstituted $C_1-C_{20}$ alkyl, $C_2-C_{20}$ alkenyl, $C_3-C_{10}$ cycloalkyl, aryl or heterocyclic group,
wherein the substituent is selected from F, Cl, Br, $NO_2$, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $N_3$, $-N(R^{10})_2$, $R^{11}OC(O)NR^{10}-$ and $C_1-C_{20}$ alkyl, and
d) $C_1-C_6$ alkyl substituted with an unsubstituted or substituted group selected from aryl, heterocycle and $C_3-C_{10}$ cycloalkyl;or $R^{5a}$ and $R^{5b}$ are combined to form $-(CH_2)_s-$ wherein one of the carbon atoms is optionally replaced by a moiety selected from: O, $S(O)_m$, $-NC(O)-$, and $-N(COR^{10})-$;

X-Y is

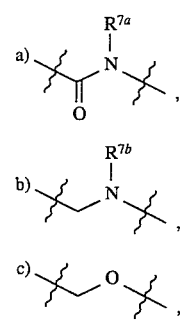

d) 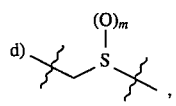

e) 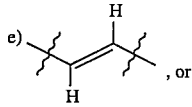, or f) —CH$_2$—CH$_2$—;

R$^{7a}$ is selected from
  a) hydrogen,
  b) unsubstituted or substituted aryl,
  c) unsubstituted or substituted heterocyclic,
  d) unsubstituted or substituted cycloalkyl, and
  e) C$_1$–C$_6$ alkyl substituted with hydrogen or an unsubstituted or substituted group selected from aryl, heterocyclic and cycloalkyl;

R$^{7b}$ is selected from
  a) hydrogen,
  b) unsubstituted or substituted aryl,
  c) unsubstituted or substituted heterocyclic,
  d) unsubstituted or substituted cycloalkyl,
  e) C$_1$–C$_6$ alkyl substituted with hydrogen or an unsubstituted or substituted group selected from aryl, heterocyclic and cycloalkyl,
  f) a carbonyl group which is bonded to an unsubstituted or substituted group selected from aryl, heterocyclic, cycloalkyl and C$_1$–C$_6$ alkyl substituted with hydrogen or an unsubstituted or substituted group selected from aryl, heterocyclic and cycloalkyl, and
  g) a sulfonyl group which is bonded to an unsubstituted or substituted group selected from aryl, heterocyclic, cycloalkyl and C$_1$–C$_6$ alkyl substituted with hydrogen or an unsubstituted or substituted group selected from aryl, heterocyclic and cycloalkyl;

R$^8$ is independently selected from:
  a) hydrogen,
  b) aryl, heterocyclic, cycloalkyl, alkenyl, alkynyl, perfluoroalkyl, F, Cl, Br, R$^{10}$O—, R$^{11}$S(O)$_m$—, R$^{10}$C(O)NR$^{10}$—, CN, NO$_2$, R$^{10}{}_2$N—C(NR$^{10}$)—, R$^{10}$C(O)—, R$^{10}$OC(O)—, N$_3$, —N(R$^{10}$)$_2$, or R$^{11}$OC(O)NR$^{10}$—, and
  c) C$_1$–C$_6$ alkyl unsubstituted or substituted by aryl, heterocyclic, cycloalkyl, alkenyl, alkynyl, perfluoroalkyl, F, Cl, Br, R$^{10}$O—, R$^{11}$S(O)$_m$—, R$^{10}$C(O)NH—, CN, H$_2$N—C(NH)—, R$^{10}$C(O)—, R$^{10}$OC(O)—, N$_3$, —N(R$^{10}$)$_2$, or R$^{11}$OC(O)NH—;

R$^9$ is selected from:
  hydrogen, C$_1$–C$_6$ alkyl, R$^{10}$O—, R$^{11}$S(O)$_m$—, R$^{10}$C(O)NR$^{10}$—, CN, NO$_2$, N$_3$, —N(R$^{10}$)$_2$, and R$^{11}$OC(O)NR$^{10}$—;

provided that R$^9$ is not R$^{10}$C(O)NR$^{10}$— when R$^{1a}$ is alkenyl, V is hydrogen and X-Y is —C(O)NR$^{7a}$—;

R$^{10}$ is independently selected from hydrogen, C$_1$–C$_6$ alkyl, benzyl and aryl;

R$^{11}$ is independently selected from C$_1$–C$_6$ alkyl and aryl;

R$^{12}$ is hydrogen or C$_1$–C$_6$ alkyl;

V is selected from:
  a) aryl;
  b) heterocycle; or
  c) hydrogen;

W is
  —S(O)$_m$—, —O—, —NHC(O)—, —C(O)NH—, —NHSO$_2$—, —SO$_2$NH—, —N(R$^{7a}$)— or —N[C(O)R$^{7a}$]—;

Z is independently H$_2$ or O;

m is 0, 1 or 2;

n is 0, 1, 2, 3 or 4, provided that n≠0 when V is hydrogen and W is —S(O)$_m$—;

p is 0, 1, 2, 3 or 4, provided that p≠0 when R$^9$ is not hydrogen or C$_1$–C$_6$ lower alkyl;

r is 0 or 1;

s is 4 or 5; and t is 0, 1 or 2, provided that t=0 when V is hydrogen;
or a pharmaceutically acceptable salt thereof.

2. A prodrug of a compound of claim 1 having the formula II:

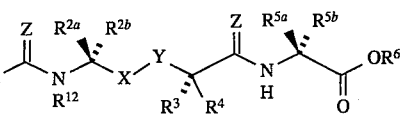

wherein:
  R$^{1a}$ is selected from:
    a) hydrogen,
    b) aryl, heterocyclic, cycloalkyl, alkenyl, alkynyl, (R$^{10}$)$_2$N—C(NR$^{10}$)—, R$^{10}$C(O)—, or R$^{10}$OC(O)—, and
    c) C$_1$–C$_6$ alkyl unsubstituted or substituted by aryl, heterocyclic, cycloalkyl, alkenyl, alkynyl, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—;

R$^{1b}$ is independently selected from:
    a) hydrogen,
    b) unsubstituted or substituted aryl, cycloalkyl, alkenyl, alkynyl, (R$^{10}$)$_2$N—C(NR$^{10}$)—, R$^{10}$C(O)—, or R$^{10}$OC(O)—, and,
    c) C$_1$–C$_6$ alkyl unsubstituted or substituted by unsubstituted or substituted aryl, cycloalkyl, alkenyl, alkynyl, R$^{10}$O—, R$^{11}$S(O)$_m$—, R$^{10}$C(O)NR$^{10}$—, CN, (R$^{10}$)$_2$N—C(NR$^{10}$), R$^{10}$C(O)—, R$^{10}$OC(O)—, N$_3$, —N(R$^{10}$)$_2$, or R$^{11}$OC(O)NR$^{10}$—;

provided that R$^{1b}$ is not R$^{10}$OC(O)NR$^{10}$— when R$^{1a}$ is alkenyl, V is hydrogen and X-Y is —C(O)NR$^{7a}$—;

R$^{2a}$ and R$^{2b}$ are independently selected from:
    a) a side chain of a naturally occurring amino acid,
    b) an oxidized form of a side chain of a naturally occurring amino acid which is:
      i) methionine sulfoxide, or
      ii) methionine sulfone,
    c) substituted or unsubstituted C$_1$–C$_{20}$ alkyl, C$_2$–C$_{20}$ alkenyl, C$_3$–C$_{10}$ cycloalkyl, aryl or heterocyclic group,
      wherein the substituent is selected from F, Cl, Br, NO$_2$, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, R$^{11}$OC(O)NR$^{10}$— and C$_1$–C$_{20}$ alkyl, and d) $C_1-C_6$ alkyl substituted with an unsubstituted or substituted group selected from aryl, heterocycle and $C_3-C_{10}$ cycloalkyl; or $R^{2a}$ and $R^{2b}$ are combined to form $-(CH_2)_s-$;

$R^3$ and $R^4$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1-C_{20}$ alkyl, $C_2-C_{20}$ alkenyl, $C_3-C_{10}$ cycloalkyl, aryl or heterocyclic group,
    wherein the substituent is selected from F, Cl, Br, $N(R^{10})_2$, $NO_2$, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $N_3$, $-N(R^{10})_2$, $R^{11}OC(O)NR^{10}-$ and $C_1-C_{20}$ alkyl, and
  d) $C_1-C_6$ alkyl substituted with an unsubstituted or substituted group selected from aryl, heterocycle and $C_3-C_{10}$ cycloalkyl; or $R^3$ and $R^4$ are combined to form $-(CH_2)_s-$;

$R^{5a}$ and $R^{5b}$ independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1-C_{20}$ alkyl, $C_2-C_{20}$ alkenyl, $C_3-C_{10}$ cycloalkyl, aryl or heterocyclic group,
    wherein the substituent is selected from F, Cl, Br, $NO_2$, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $N_3$, $-N(R^{10})_2$, $R^{11}OC(O)NR^{10}-$ and $C_1-C_{20}$ alkyl, and
  d) $C_1-C_6$ alkyl substituted with an unsubstituted or substituted group selected from aryl, heterocycle and $C_3-C_{10}$ cycloalkyl; or $R^{5a}$ and $R^{5b}$ are combined to form $-(CH_2)_s-$ wherein one of the carbon atoms is optionally replaced by a moiety selected from: O, $S(O)_m$, $-NC(O)-$, and $-N(COR^{10})-$;

$R^6$ is
  a) substituted or unsubstituted $C_1-C_8$ alkyl, wherein the substituent on the alkyl is selected from:
    1) aryl,
    2) heterocycle,
    3) $-N(R^{11})_2$,
    4) $-OR^{10}$, or
  b)

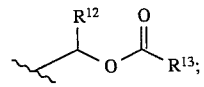

X-Y is a) 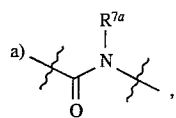

b) 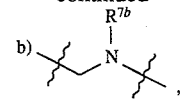, c) 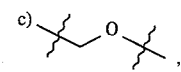, d) 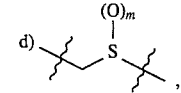, e) 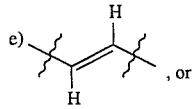, or f) $-CH_2-CH_2-$;

$R^{7a}$ is selected from
  a) hydrogen,
  b) unsubstituted or substituted aryl,
  c) unsubstituted or substituted heterocyclic,
  d) unsubstituted or substituted cycloalkyl, and
  e) $C_1-C_6$ alkyl substituted with hydrogen or an unsubstituted or substituted group selected from aryl, heterocyclic and cycloalkyl;

$R^{7b}$ is selected from
  a) hydrogen,
  b) unsubstituted or substituted aryl,
  c) unsubstituted or substituted heterocyclic,
  d) unsubstituted or substituted cycloalkyl,
  e) $C_1-C_6$ alkyl substituted with hydrogen or an unsubstituted or substituted group selected from aryl, heterocyclic and cycloalkyl,
  f) a carbonyl group which is bonded to an unsubstituted or substituted group selected from aryl, heterocyclic, cycloalkyl and $C_1-C_6$ alkyl substituted with hydrogen or an unsubstituted or substituted group selected from aryl, heterocyclic and cycloalkyl, and
  g) a sulfonyl group which is bonded to an unsubstituted or substituted group selected from aryl, heterocyclic, cycloalkyl and $C_1-C_6$ alkyl substituted with hydrogen or an unsubstituted or substituted group selected from aryl, heterocyclic and cycloalkyl;

$R^8$ is independently selected from:
  a) hydrogen,
  b) aryl, heterocyclic, cycloalkyl, alkenyl, alkynyl, perfluoroalkyl, F, Cl, Br, $R^{10}O-$, $R^{11}S(O)_m-$, $R^{10}C(O)NR^{10}-$, CN, $NO_2$, $R^{10}_2N-C(NR^{10})-$, $R^{10}C(O)-$, $R^{10}OC(O)-$, $N_3$, $-N(R^{10})_2$, or $R^{11}OC(O)NR^{10}-$, and
  c) $C_1-C_6$ alkyl unsubstituted or substituted by aryl, heterocyclic, cycloalkyl, alkenyl, alkynyl, perfluoroalkyl, F, Cl, Br, $R^{10}O-$, $R^{11}S(O)_m-$, $R^{10}C(O)NH-$, CN, $H_2N-C(NH)-$, $R^{10}C(O)-$, $R^{10}OC(O)-$, $N_3$, $-N(R^{10})_2$, or $R^{11}OC(O)NH-$;

$R^9$ is selected from:
  hydrogen, $C_1-C_6$ alkyl, $R^{10}O-$, $R^{11}S(O)_m-$, $R^{10}C(O)NR^{10}-$, CN, $NO_2$, $N_3$, $-N(R^{10})_2$, and $R^{11}OC(O)NR^{10}-$;

provided that $R^9$ is not $R^{10}C(O)NR^{10}-$ when $R^{1a}$ is alkenyl, V is hydrogen and X-Y is $-C(O)NR^{7a}-$;

$R^{10}$ is independently selected from hydrogen, $C_1-C_6$ alkyl, benzyl and aryl;

$R^{11}$ is independently selected from $C_1-C_6$ alkyl and aryl;

$R^{12}$ is independently selected from hydrogen and $C_1$–$C_6$ alkyl;

$R^{13}$ is $C_1$–$C_6$ alkyl;

V is selected from:
  a) aryl;
  b) heterocycle; or
  c) hydrogen;

W is
—S(O)$_m$—, —O—, —NHC(O)—, —C(O)NH—, —NHSO$_2$—, —SO$_2$NH—, —N(R$^{7a}$)— or —N[C(O)R$^{7a}$]—;

Z is independently H$_2$ or O;

m is 0, 1 or 2;

n is 0, 1, 2, 3 or 4, provided that n≠0 when V is hydrogen and W is —S(O)$_m$—;

p is 0, 1, 2, 3 or 4, provided that p≠0 when $R^9$ is not hydrogen or $C_1$–$C_6$ lower alkyl;

r is 0 or 1;

s is 4 or 5; and t is 0, 1 or 2, provided that t=0 when V is hydrogen;
or a pharmaceutically acceptable salt thereof.

3. A compound which inhibits Ras farnesyltransferase having the formula III:

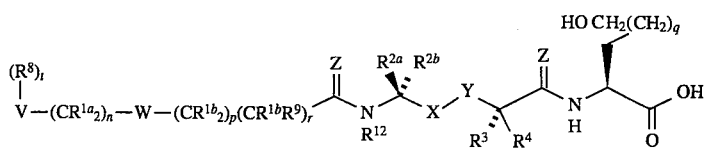

wherein:

$R^{1a}$ is selected from:
  a) hydrogen,
  b) aryl, heterocyclic, cycloalkyl, alkenyl, alkynyl, (R$^{10}$)$_2$N—C(NR$^{10}$)—, R$^{10}$C(O)—, or R$^{10}$OC(O)—, and
  c) $C_1$–$C_6$ alkyl unsubstituted or substituted by aryl, heterocyclic, cycloalkyl, alkenyl, alkynyl, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—;

$R^{1b}$ is independently selected from:
  a) hydrogen,
  b) unsubstituted or substituted aryl, cycloalkyl, alkenyl, alkynyl, (R$^{10}$)$_2$N—C(NR$^{10}$)—, R$^{10}$C(O)—, or R$^{10}$OC(O)—, and
  c) $C_1$–$C_6$ alkyl unsubstituted or substituted by unsubstituted or substituted aryl, cycloalkyl, alkenyl, alkynyl, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—;
  provided that $R^{1b}$ is not R$^{10}$C(O)NR$^{10}$— when $R^{1a}$ is alkenyl, V is hydrogen and X-Y is —C(O)NR$^{7a}$—;

$R^{2a}$ and $R^{2b}$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1$–$C_{20}$ alkyl, $C_2$–$C_{20}$ alkenyl, $C_3$–$C_{10}$ cycloalkyl, aryl or heterocyclic group,
    wherein the substituent is selected from F, Cl, Br, NO$_2$, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, R$^{11}$OC(O)NR$^{10}$— and $C_1$–$C_{20}$ alkyl, and
  d) $C_1$–$C_6$ alkyl substituted with an unsubstituted or substituted group selected from aryl, heterocycle and $C_3$–$C_{10}$ cycloalkyl; or $R^{2a}$ and $R^{2b}$ are combined to form —(CH$_2$)$_s$—;

$R^3$ and $R^4$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1$–$C_{20}$ alkyl, $C_2$–$C_{20}$ alkenyl, $C_3$–$C_{10}$ cycloalkyl, aryl or heterocyclic group,
    wherein the substituent is selected from F, Cl, Br, NO$_2$, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, R$^{11}$OC(O)NR$^{10}$— and $C_1$–$C_{20}$ alkyl, and
  d) $C_1$–$C_6$ alkyl substituted with an unsubstituted or substituted group selected, from aryl, heterocycle and $C_3$–$C_{10}$ cycloalkyl; or $R^3$ and $R^4$ are combined to form —(CH$_2$)$_s$—;

X-Y is

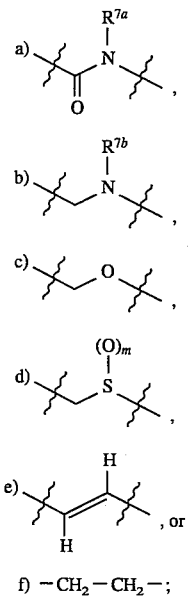

f) —CH$_2$—CH$_2$—;

$^{7a}$ is selected from
  a) hydrogen,
  b) unsubstituted or substituted aryl,
  c) unsubstituted or substituted heterocyclic,
  d) unsubstituted or substituted cycloalkyl, and
  e) $C_1$–$C_6$ alkyl substituted with hydrogen or an unsubstituted or substituted group selected from aryl, heterocyclic and cycloalkyl;

$R^{7b}$ is selected from
  a) hydrogen, b) unsubstituted or substituted aryl,
c) unsubstituted or substituted heterocyclic,
d) unsubstituted or substituted cycloalkyl,
e) $C_1$–$C_6$ alkyl substituted with hydrogen or an unsubstituted or substituted group selected from aryl, heterocyclic and cycloalkyl,
f) a carbonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl, and
g) a sulfonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl;

$R^8$ is independently selected from:
  a) hydrogen,
  b) aryl, heterocyclic, cycloalkyl, alkenyl, alkynyl, perfluoroalkyl, F, Cl, Br, $R^{10}O$—, $R^{11}S(O)_m$—, $R^{10}C(O)NR^{10}$, CN, $NO_2$, $R^{10}{}_2N$—$C(NR^{10})$—, $R^{10}C(O)$—, $R^{10}OC(O)$—, $N_3$, —$N(R^{10})_2$, or $R^{11}OC(O)NR^{10}$—, and
  c) $C_1$–$C_6$ alkyl unsubstituted or substituted by aryl, heterocyclic, cycloalkyl, alkenyl, alkynyl, perfluoroalkyl, F, Cl, Br, $R^{10}O$—, $R^{11}S(O)_m$—, $R^{10}C(O)NH$—, $H_2N$—$C(NH)$—, $R^{10}C(O)$—, $R^{10}OC(O)$—, $N_3$, —$N(R^{10})_2$, or $R^{11}OC(O)NH$—;

$R^9$ is selected from:
  hydrogen, $C_1$–$C_6$ alkyl, $R^{10}O$—, $R^{11}S(O)_m$—, $R^{10}C(O)NR^{10}$—, CN, $NO_2$, $N_3$, —$N(R^{10})_2$, and $R^{11}OC(O)NR^{10}$—;
  provided that $R^9$ is not $R^{10}C(O)NR^{10}$— when $R^{1a}$ is alkenyl, V is hydrogen and X-Y is —$C(O)NR^{7a}$—;

$R^{10}$ is independently selected from hydrogen, $C_1$–$C_6$ alkyl, benzyl and aryl;

$R^{11}$ is independently selected from $C_1$–$C_6$ alkyl and aryl;

$R^{12}$ is hydrogen or $C_1$–$C_6$ alkyl;

V is selected from:
  a) aryl;
  b) heterocycle; or
  c) hydrogen;

W is
  —$S(O)_m$—, —O—, —NHC(O)—, —C(O)NH—, —$NHSO_2$—, —$SO_2NH$—, —$N(R^{7a})$— or —$N[C(O)R^{7a}]$—;

Z is independently $H_2$ or O;

m is 0, 1 or 2;

n is 0, 1, 2, 3 or 4, provided that n≠0 when V is hydrogen and W is —$S(O)_m$—;

p is 0, 1, 2, 3 or 4, provided that p≠0 when $R^9$ is not hydrogen or $C_1$–$C_6$ lower alkyl;

q is 0, 1 or 2;

r is 0 or 1;

s is 4 or 5; and t is 0, 1 or 2, provided that t=0 when V is hydrogen;

or a pharmaceutically acceptable salt thereof.

4. A prodrug of a compound of claim 3 of the formula IV:

$$(R^8)_t \quad V-(CR^{1a}{}_2)_n-W-(CR^{1b}{}_2)_p(CR^{1b}R^9)_r \cdots \quad \text{IV}$$

wherein:
$R^{1a}$ is selected from:
  a) hydrogen,
  b) aryl, heterocyclic, cycloalkyl, alkenyl, alkynyl, $(R^{10})_2N$—$C(NR^{10})$—, $R^{10}C(O)$—, or $R^{10}OC(O)$—, and
  c) $C_1$–$C_6$ alkyl unsubstituted or substituted by aryl, heterocyclic, cycloalkyl, alkenyl, alkynyl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;

$R^{1b}$ is independently selected from:
  a) hydrogen,
  b) unsubstituted or substituted aryl, cycloalkyl, alkenyl, alkynyl, $(R^{10})_2N$—$C(NR^{10})$—, $R^{10}C(O)$—, or $R^{10}OC(O)$—, and
  c) $C_1$–$C_6$ alkyl unsubstituted or substituted by unsubstituted or substituted aryl, cycloalkyl, alkenyl, alkynyl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;
  provided that $R^{1b}$ is not $R^{10}C(O)NR^{10}$— when $R^{1a}$ is alkenyl, V is hydrogen and X-Y is —$C(O)NR^{7a}$—;

$R^{2a}$ and $R^{2b}$ are independently selected from:
  a) a side chain of a naturally occurring amino acid,
  b) an oxidized form of a side chain of a naturally occurring amino acid which is:
    i) methionine sulfoxide, or
    ii) methionine sulfone, and
  c) substituted or unsubstituted $C_1$–$C_{20}$ alkyl, $C_2$–$C_{20}$ alkenyl, $C_3$–$C_{10}$ cycloalkyl, aryl or heterocyclic group,
    wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
  d) $C_1$–$C_6$ alkyl substituted with an unsubstituted or substituted group selected from aryl, heterocycle and $C_3$–$C_{10}$ cycloalkyl; or $R^{2a}$ and $R^{2b}$ are combined to form —$(CH_2)_s$—;

$R^3$ and $R^4$ are independently selected from:
  a) a side chain of a naturally occurring amino acid,
  b) an oxidized form of a side chain of a naturally occurring amino acid which is:
    i) methionine sulfoxide, or
    ii) methionine sulfone, and
  c) substituted or unsubstituted $C_1$–$C_{20}$ alkyl, $C_2$–$C_{20}$ alkenyl, $C_3$–$C_{10}$ cycloalkyl, aryl or heterocyclic group,
    wherein the substituent is selected from F, Cl, Br, $NO_2$, $R^{10}O$—, $R^{11}S(O)_m$—, $R^{10}C(O)NR^{10}$—, CN, $(R^{10})_2N$—C(NR$^{10}$)—, R$^{10}$C(O)—, R$^{10}$OC(O)—, N$_3$, —N(R$^{10}$)$_2$, R$^{11}$OC(O)NR$^{10}$— and C$_1$–C$_{20}$ alkyl, and d) C$_1$–C$_6$ alkyl substituted with an unsubstituted or substituted group selected from aryl, heterocycle and C$_3$–C$_{10}$ cycloalkyl; or R$^3$ and R$^4$ are combined to form —(CH$_2$)$_s$—;

X-Y is a) [structure: C(=O)N(R$^{7a}$)], b) [structure: CH$_2$N(R$^{7b}$)], c) [structure: CH$_2$O], d) [structure: CH$_2$S(O)$_m$], e) [structure: HC=CH], or f) —CH$_2$—CH$_2$—;

R$^{7a}$ is selected from
 a) hydrogen,
 b) unsubstituted or substituted aryl,
 c) unsubstituted or substituted heterocyclic,
 d) unsubstituted or substituted cycloalkyl, and
 e) C$_1$–C$_6$ alkyl substituted with hydrogen or an unsubstituted or substituted group selected from aryl, heterocyclic and cycloalkyl;

R$^{7b}$ is selected from
 a) hydrogen,
 b) unsubstituted or substituted aryl,
 c) unsubstituted or substituted heterocyclic,
 d) unsubstituted or substituted cycloalkyl,
 e) C$_1$–C$_6$ alkyl substituted with hydrogen or an unsubstituted or substituted group selected from aryl, heterocyclic and cycloalkyl,
 f) a carbonyl group which is bonded to an unsubstituted or substituted group selected from aryl, heterocyclic, cycloalkyl and C$_1$–C$_6$ alkyl substituted with hydrogen or an unsubstituted or substituted group selected from aryl, heterocyclic and cycloalkyl, and
 g) a sulfonyl group which is bonded to an unsubstituted or substituted group selected from aryl, heterocyclic, cycloalkyl and C$_1$–C$_6$ alkyl substituted with hydrogen or an unsubstituted or substituted group selected from aryl, heterocyclic and cycloalkyl;

R$^8$ is independently selected from:
 a) hydrogen,
 b) aryl, heterocyclic, cycloalkyl, alkenyl, alkynyl, perfluoroalkyl, F, Cl, Br, R$^{10}$O—, R$^{11}$S(O)$_m$—, R$^{10}$C(O)NR$^{10}$—, CN, NO$_2$, R$^{10}_2$N—C(NR$^{10}$)—, R$^{10}$C(O)—, R$^{10}$OC(O)—, N$_3$, —N(R$^{10}$)$_2$, or R$^{11}$OC(O)NR$^{10}$—, and
 c) C$_1$–C$_6$ alkyl unsubstituted or substituted by aryl, heterocyclic, cycloalkyl, alkenyl, alkynyl, perfluoroalkyl, F, Cl, Br, R$^{10}$O—, R$^{11}$S(O)$_m$—, R$^{10}$C(O)NH—, CN, H$_2$N—C(NH)—, R$^{10}$C(O)—, R$^{10}$OC(O)—, N$_3$, —N(R$^{10}$)$_2$, or R$^{11}$OC(O)NH—;

R$^9$ is selected from:
 hydrogen, C$_1$–C$_6$ alkyl, R$^{10}$O—, R$^{11}$S(O)$_m$—, R$^{10}$C(O)NR$^{10}$—, CN, NO$_2$, N$_3$, —N(R$^{10}$)$_2$, and R$^{11}$OC(O)NR$^{10}$—;

provided that R$^9$ is not R$^{10}$C(O)NR$^{10}$— when R$^{1a}$ is alkenyl, V is hydrogen and X-Y is —C(O)NR$^{7a}$—;

R$^{10}$ is independently selected from hydrogen, C$_1$–C$_6$ alkyl, benzyl and aryl;

R$^{11}$ is independently selected from C$_1$–C$_6$ alkyl and aryl;

R$^{12}$ is hydrogen or C$_1$–C$_6$ alkyl;

V is selected from:
 a) aryl;
 b) heterocycle; or
 c) hydrogen;

W is
 —S(O)$_m$—, —O—, —NHC(O)—, —C(O)NH—, —NHSO$_2$—, —SO$_2$NH—, —N(R$^{7a}$)— or —N[C(O)R$^{7a}$]—;

Z is independently H$_2$ or O m is 0, 1 or 2;

n is 0, 1, 2, 3 or 4, provided that n≠0 when V is hydrogen and W is —S(O)$_m$—;

p is 0, 1, 2, 3 or 4, provided that p≠0 when R$^9$ is not hydrogen or C$_1$–C$_6$ lower alkyl;

q is 0, 1 or 2;

r is 0 or 1;

s is 4 or 5; and t is 0, 1 or 2, provided that t=0 when V is hydrogen;

or a pharmaceutically acceptable salt thereof.

5. The compound according to claim 1 having the formula I:

$$\text{V}-(\text{CR}^{1a}_2)_n-\text{W}-\overset{(\text{R}^8)_t}{|}\cdots-(\text{CR}^{1b}_2)_p(\text{CR}^{1b}\text{R}^9)_r\overset{Z}{\underset{\text{R}^{12}}{\text{C}}}-\text{N}\overset{\text{R}^{2a}\ \text{R}^{2b}}{\underset{\text{R}^3\ \text{R}^4}{\text{C}}}-\text{X}-\text{Y}-\overset{Z}{\underset{\text{H}}{\text{C}}}-\text{N}\overset{\text{R}^{5a}\ \text{R}^{5b}}{\text{C}}-\text{C(O)OH}$$

wherein:

R$^{1a}$ is selected from:
 a) hydrogen, and
 b) C$_1$–C$_6$ alkyl;

R$^{1b}$ is independently selected from:
 a) hydrogen,
 b) unsubstituted or substituted aryl or cycloalkyl, and
 c) C$_1$–C$_6$ alkyl unsubstituted or substituted by unsubstituted or substituted aryl, cycloalkyl, alkenyl, R$^{10}$O— or —N(R$^{10}$)$_2$;

R$^{2a}$ is selected from:
 a) a side chain of a naturally occurring amino acid, wherein the amino acid is selected from alanine, leucine, isoleucine and valine;
 b) substituted or unsubstituted C$_1$–C$_{10}$ alkyl, C$_2$–C$_{10}$ alkenyl, C$_3$–C$_{10}$ cycloalkyl, aryl or heterocyclic group,
  wherein the substituent is selected from F, Cl, Br, NO$_2$, R$^{10}$O—, R$^{11}$S(O)$_m$—, R$^{10}$C(O)NR$^{10}$—, CN, $(R^{10})_2$N—C(NR$^{10}$)—, R$^{10}$C(O)—, $R^{10}OC(O)-$, $N_3$, $-N(R^{10})_2$, $R^{11}OC(O)NR^{10}-$ and $C_1-C_{20}$ alkyl, and c) $C_1-C_6$ alkyl substituted with an unsubstituted or substituted group selected from aryl, heterocycle and $C_3-C_{10}$ cycloalkyl; and $R^{2b}$ is selected from hydrogen and $C_1-C_6$ alkyl; or $R^{2a}$ and $R^{2b}$ are combined to form $-(CH_2)_s-$;

$R^3$ and $R^4$ are independently selected from:
a) a side chain of a naturally occurring amino acid,
b) an oxidized form of a side chain of a naturally occurring amino acid which is:
 i) methionine sulfoxide, or
 ii) methionine sulfone,
c) substituted or unsubstituted $C_1-C_{10}$ alkyl, $C_2-C_{10}$ alkenyl, $C_3-C_{10}$ cycloalkyl, aryl or heterocycle group,
 wherein the substituent is selected from F, Cl, Br, $NO_2$, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $N_3$, $-N(R^{10})_2$, $R^{11}OC(O)NR^{10}-$ and $C_1-C_{20}$ alkyl, and
d) $C_1-C_6$ alkyl substituted with an unsubstituted or substituted group selected from aryl, heterocycle and $C_3-C_{10}$ cycloalkyl;

$R^{5a}$ is selected from:
a) a side chain of a naturally occurring amino acid, wherein the amino acid is selected from methionine and glutamine,
b) an oxidized form of a side chain of a naturally occurring amino acid which is:
 i) methionine sulfoxide, or
 ii) methionine sulfone, and
c) substituted or unsubstituted $C_1-C_{10}$ alkyl, $C_2-C_{10}$ alkenyl, $C_3-C_{10}$ cycloalkyl, aryl or heterocyclic group,
 wherein the substituent is selected from F, Cl, Br, $NO_2$, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $N_3$, $-N(R^{10})_2$, $R^{11}OC(O)NR^{10}-$ and $C_1-C_{20}$ alkyl, and
d) $C_1-C_6$ alkyl substituted with an unsubstituted or substituted group selected from aryl, heterocycle and $C_3-C_{10}$ cycloalkyl;

$R^{5b}$ is selected from:
a) hydrogen, and
b) $C_1-C_3$ alkyl; or

X-Y is

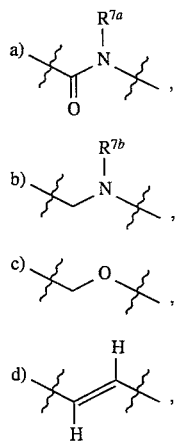

or e) $-CH_2-CH_2-$;

$R^{7a}$ is selected from
a) hydrogen,
b) unsubstituted or substituted aryl,
c) unsubstituted or substituted heterocyclic,
d) unsubstituted or substituted cycloalkyl, and
e) $C_1-C_6$ alkyl substituted with hydrogen or an unsubstituted or substituted group selected from aryl, heterocyclic and cycloalkyl;
 wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
a) hydrogen,
b) unsubstituted or substituted aryl,
c) unsubstituted or substituted heterocyclic,
d) unsubstituted or substituted cycloalkyl,
e) $C_1-C_6$ alkyl substituted with hydrogen or an unsubstituted or substituted group selected from aryl, heterocyclic and cycloalkyl,
f) a carbonyl group which is bonded to an unsubstituted or substituted group selected from aryl, heterocyclic, cycloalkyl and $C_1-C_6$ alkyl substituted with hydrogen or an unsubstituted or substituted group selected from aryl, heterocyclic and cycloalkyl, and
g) a sulfonyl group which is bonded to an unsubstituted or substituted group selected from aryl, heterocyclic, cycloalkyl and $C_1-C_6$ alkyl substituted with hydrogen or an unsubstituted or substituted group selected from aryl, heterocyclic and cycloalkyl;
 wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is independently selected from:
a) hydrogen,
b) $C_1-C_6$ alkyl, $C_2-C_6$ alkenyl, $C_2-C_6$ alkynyl, $C_1-C_6$ perfluoroalkyl, F, Cl, $R^{10}O-$, $R^{10}C(O)NR^{10}-$, CN, $NO_2$, $(R^{10})_2N-C(NR^{10})-$, $R^{10}C(O)-$, $R^{10}OC(O)-$, $N(R^{10})_2$, or $R^{11}OC(O)NR^{10}-$, and
c) $C_1-C_6$ alkyl substituted by $C_1-C_6$ perfluoroalkyl, $R^{10}O-$, $R^{10}C(O)NR^{10}-$, $(R^{10})_2N-C(NR^{10})-$, $R^{10}C(O)-$, $R^{10}OC(O)-$, $-N(R^{10})_2$, or $R^{11}OC(O)NR^{10}-$;

$R^9$ is selected from:
hydrogen, $C_1-C_6$ lower alkyl, $R^{10}O-$, and $-N(R^{10})_2$;

$R^{10}$ is independently selected from hydrogen, $C_1-C_6$ alkyl, benzyl and aryl;

$R^{11}$ is independently selected from $C_1-C_6$ alkyl and aryl;

$R^{12}$ is hydrogen or $C_1-C_6$ alkyl;

V is selected from:
a) aryl;
b) heterocycle selected from pyrrolidinyl, imidazolyl, pyridinyl, thiazolyl, pyridonyl, 2-oxopiperidinyl, indolyl, quinolinyl, isoquinolinyl, and thienyl; and
c) hydrogen;

W is
$-S(O)_m-$, $-O-$, $-NHC(O)-$, $-C(O)NH-$, $-NHSO_2-$, $-SO_2NH-$, $-N(R^{7a})-$ or $-N[C(O)R^{7a}]-$;

Z is independently $H_2$ or O m is 0, 1 or 2;

n is 0, 1, 2, 3 or 4, provided that n≠0 when V is hydrogen and W is —S(O)$_m$—;

p is 0, 1, 2, 3 or 4, provided that p≠0 when R$^9$ is not hydrogen or C$_1$–C$_6$ lower alkyl;

r is 0 or 1;

s is 4 or 5; and t is 0 or 1, provided that t=0 when V is hydrogen;

or a pharmaceutically acceptable salt thereof.

6. The compound according to claim 2 having the formula II:

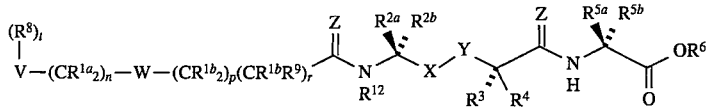

II wherein:

R$^{1a}$ is selected from:
a) hydrogen, and
b) C$_1$–C$_6$ alkyl;

R$^{1b}$ is independently selected from:
a) hydrogen,
b) unsubstituted or substituted aryl or cycloalkyl, and
c) C$_1$–C$_6$ alkyl unsubstituted or substituted by unsubstituted or substituted aryl, cycloalkyl, alkenyl, R$^{10}$O— or —N(R$^{10}$)$_2$;

R$^{2a}$ is selected from:
a) a side chain of a naturally occurring amino acid, wherein the amino acid is selected from alanine, leucine, isoleucine and valine;
b) substituted or unsubstituted C$_1$–C$_{10}$ alkyl, C$_2$–C$_{10}$ alkenyl, C$_3$–C$_{10}$ cycloalkyl, aryl or heterocyclic group,
wherein the substituent is selected from F, Cl, Br, NO$_2$, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, R$^{11}$OC(O)NR$^{10}$— and C$_1$–C$_{20}$ alkyl, and
c) C$_1$–C$_6$ alkyl substituted with an unsubstituted or substituted group selected from aryl, heterocycle and C$_3$–C$_{10}$ cycloalkyl; and R$^{2b}$ is selected from hydrogen and C$_1$–C$_6$ alkyl; or R$^{2a}$ and R$^{2b}$ are combined to form —(CH$_2$)$_s$—;

R$^3$ and R$^4$ are independently selected from:
a) a side chain of a naturally occurring amino acid,
b) an oxidized form of a side chain of a naturally occurring amino acid which is:
i) methionine sulfoxide, or
ii) methionine sulfone,
c) substituted or unsubstituted C$_1$–C$_{10}$ alkyl, C$_2$–C$_{10}$ alkenyl, C$_3$–C$_{10}$ cycloalkyl, aryl or heterocycle group,
wherein the substituent is selected from F, Cl, Br, NO$_2$, R$^{10}$O—, R$^{11}$S(O)$_m$—, R$^{10}$C(O)NR$^{10}$—, CN, NO$_2$, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, R$^{11}$OC(O)NR$^{10}$— and C$_1$–C$_{20}$ alkyl, and
d) C$_1$–C$_6$ alkyl substituted with an unsubstituted or substituted group selected from aryl, heterocycle and C$_3$–C$_{10}$ cycloalkyl;

R$^{5a}$ is selected from:
a) a side chain of a naturally occurring amino acid, wherein the amino acid is selected from methionine and glutamine,
b) an oxidized form of a side chain of a naturally occurring amino acid which is:
i) methionine sulfoxide, or
ii) methionine sulfone, and
c) substituted or unsubstituted C$_1$–C$_{10}$ alkyl, C$_2$–C$_{10}$ alkenyl, C$_3$–C$_{10}$ cycloalkyl, aryl or heterocyclic group,
wherein the substituent is selected from F, Cl, Br, NO$_2$, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, R$^{11}$OC(O)NR$^{10}$— and C$_1$–C$_{20}$ alkyl, and
d) C$_1$–C$_6$ alkyl substituted with an unsubstituted or substituted group selected from aryl, heterocycle and C$_3$–C$_{10}$ cycloalkyl;

R$^{5b}$ is selected from:
a) hydrogen, and
b) C$_1$–C$_3$ alkyl; or

R$^6$ is
a) substituted or unsubstituted C$_1$–C$_8$ alkyl, wherein the substituent on the alkyl is selected from:
1) aryl,
2) heterocycle,
3) —N(R$^{11}$)$_2$,
4) —OR$^{10}$, or
b)

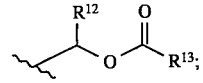

X-Y is a) 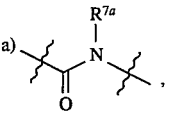, b) 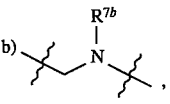, c) 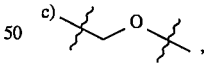, d) 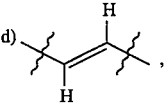

or e) —CH$_2$—CH$_2$—;

R$^{7a}$ is selected from
a) hydrogen,
b) unsubstituted or substituted aryl,
c) unsubstituted or substituted heterocyclic,
d) unsubstituted or substituted cycloalkyl, and
e) C$_1$–C$_6$ alkyl substituted with hydrogen or an unsubstituted or substituted group selected from aryl, heterocyclic and cycloalkyl;

wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
a) hydrogen,
b) unsubstituted or substituted aryl,
c) unsubstituted or substituted heterocyclic,
d) unsubstituted or substituted cycloalkyl,
e) $C_1$–$C_6$ alkyl substituted with hydrogen or an unsubstituted or substituted group selected from aryl, heterocyclic and cycloalkyl,
f) a carbonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl, and
g) a sulfonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl;
wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^9$ is selected from:
hydrogen, $C_1$–$C_6$ lower alkyl, $R^{10}O$—, and —$N(R^{10})_2$;

$R^{10}$ is independently selected from hydrogen, $C_1$–$C_6$ alkyl, benzyl and aryl;

$R^{11}$ is independently selected from $C_1$–$C_6$ alkyl and aryl;

$R^{12}$ is independently selected from hydrogen and $C_1$–$C_6$ alkyl;

$R^{13}$ is $C_1$–$C_6$ alkyl;

V is selected from:
a) aryl;
b) heterocycle selected from pyrrolidinyl, imidazolyl, pyridinyl, thiazolyl, pyridonyl, 2-oxopiperidinyl, indolyl, quinolinyl, isoquinolinyl, and thienyl; and
c) hydrogen;

W is
—$S(O)_m$—, —O—, —NHC(O)—, —C(O)NH—, —$NHSO_2$—, —$SO_2NH$—, —$N(R^{7a})$— or —N[$C(O)R^{7a}$]—;

Z is independently $H_2$ or O
m is 0, 1 or 2;

n is 0, 1, 2, 3 or 4, provided that n≠0 when V is hydrogen and W is —$S(O)_m$—;

p is 0, 1, 2, 3 or 4, provided that p≠0 when $R^9$ is not hydrogen or $C_1$–$C_6$ lower alkyl;

r is 0 or 1;

s is 4 or 5; and t is 0 or 1, provided that t=0 when V is hydrogen;

or a pharmaceutically acceptable salt thereof.

7. The compound according to claim 3 having the formula III:

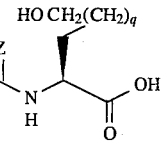

$$V—(CR^{1a}_2)_n—W—(CR^{1b}_2)_p(CR^{1b}R^9)_r \overset{(R^8)_t}{\underset{}{}} \quad \overset{Z}{\underset{R^{12}}{N}} \overset{R^{2a}\,R^{2b}}{\underset{}{}} X—Y \overset{Z}{\underset{R^3\,R^4}{}} \overset{HOCH_2(CH_2)_q}{\underset{}{N}} \underset{H}{\overset{}{}} \overset{}{\underset{O}{}} OH \qquad III$$

wherein:
$R^{1a}$ is selected from:
a) hydrogen, and
b) $C_1$–$C_6$ alkyl;

$R^{1b}$ are independently selected from:
a) hydrogen,
b) unsubstituted or substituted aryl or cycloalkyl, and
c) $C_1$–$C_6$ alkyl unsubstituted or substituted by unsubstituted or substituted aryl, cycloalkyl, alkenyl, $R^{10}O$— or —$N(R^{10})_2$;

$R^{2a}$ is selected from:
a) a side chain of a naturally occurring amino acid, wherein the amino acid is selected from alanine, leucine, isoleucine and valine;
b) substituted or unsubstituted $C_1$–$C_{10}$ alkyl, $C_2$–$C_{10}$ alkenyl, $C_3$–$C_{10}$ cycloalkyl, aryl or heterocyclic group,
  wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
c) $C_1$–$C_6$ alkyl substituted with an unsubstituted or substituted group selected from aryl, heterocycle and $C_3$–$C_{10}$ cycloalkyl; and $R^{2b}$ is selected from hydrogen and $C_1$–$C_6$ alkyl; or $R^{2a}$ and $R^{2b}$ are combined to form —$(CH_2)_s$—;

$R^3$ and $R^4$ are independently selected from:
a) a ride chain of a naturally occurring amino acid,
b) an oxidized form of a side chain of a naturally occurring amino acid which is:
  i) methionine sulfoxide, or
  ii) methionine sulfone,
c) substituted or unsubstituted $C_1$–$C_{10}$ alkyl, $C_2$–$C_{10}$ alkenyl, $C_3$–$C_{10}$ cycloalkyl, aryl or heterocycle group,
  wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl;

X-Y is

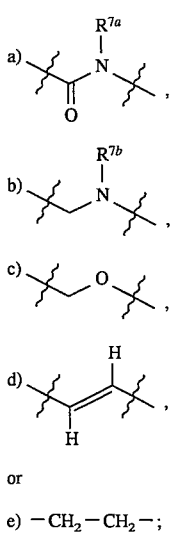

or e) $-CH_2-CH_2-$;

$R^{7a}$ is selected from
  a) hydrogen,
  b) unsubstituted or substituted aryl,
  c) unsubstituted or substituted heterocyclic,
  d) unsubstituted or substituted cycloalkyl, and
  e) $C_1-C_6$ alkyl substituted with hydrogen or an unsubstituted or substituted group selected from aryl, heterocyclic and cycloalkyl;
    wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
  a) hydrogen,
  b) unsubstituted or substituted aryl,
  c) unsubstituted or substituted heterocyclic,
  d) unsubstituted or substituted cycloalkyl,
  e) $C_1-C_6$ alkyl substituted with hydrogen or an unsubstituted or substituted group selected from aryl, heterocyclic and cycloalkyl,
  f) a carbonyl group which is bonded to an unsubstituted or substituted group selected from aryl, heterocyclic, cycloalkyl and $C_1-C_6$ alkyl substituted with hydrogen or an unsubstituted or substituted group selected from aryl, heterocyclic and cycloalkyl, and
  g) a sulfonyl group which is bonded to an unsubstituted or substituted group selected from aryl, heterocyclic, cycloalkyl and $C_1-C_6$ alkyl substituted with hydrogen or an unsubstituted or substituted group selected from aryl, heterocyclic and cycloalkyl;
    wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is independently selected from:
  a) hydrogen,
  b) $C_1-C_6$ alkyl, $C_2-C_6$ alkenyl, $C_2-C_6$ alkynyl, $C_1-C_6$ perfluoroalkyl, F, Cl, $R^{10}O-$, $R^{10}C(O)NR^{10}-$, CN, $NO_2$, $(R^{10})_2N-C(NR^{10})-$, $R^{10}C(O)-$, $R^{10}OC(O)-$, $-N(R^{10})_2$, or $R^{10}OC(O)NR^{10}-$, and
  c) $C_1-C_6$ alkyl substituted by $C_1-C_6$ perfluoroalkyl, $R^{10}O-$, $R^{10}C(O)NR^{10}-$, $(R^{10})_2N-C(NR^{10})-$, $R^{10}C(O)-$, $R^{10}OC(O)-$, $-N(R^{10})_2$, or $R^{11}OC(O)NR^{10}-$;

$R^9$ is selected from:
  hydrogen, $C_1-C_6$ lower alkyl, $R^{10}O-$, and $-N(R^{10})_2$;

$R^{10}$ is independently selected from hydrogen, $C_1-C_6$ alkyl, benzyl and aryl;

$R^{11}$ is independently selected from $C_1-C_6$ alkyl and aryl;

$R^{12}$ is hydrogen or $C_1-C_6$ alkyl;

V is selected from:
  a) aryl;
  b) heterocycle selected from pyrrolidinyl, imidazolyl, pyridinyl, thiazolyl, pyridonyl, 2-oxopiperidinyl, indolyl, quinolinyl, isoquinolinyl, and thienyl; and
  c) hydrogen;

W is
  $-S(O)_m-$, $-O-$, $-NHC(O)-$, $-C(O)NH-$, $-NHSO_2-$, $-SO_2NH-$, $-N(R^{7a})-$ or $-N-[C(O)R^{7a}]-$;

Z is independently $H_2$ or O;

m is 0, 1 or 2;

n is 0, 1, 2, 3 or 4, provided that n≠0 when V is hydrogen and W is $-S(O)_m-$;

p is 0, 1, 2, 3 or 4, provided that p≠0 when $R^9$ is not hydrogen or $C_1-C_6$ lower alkyl;

q is 0, 1 or 2;

r is 0 or 1;

s is 4 or 5; and t is 0 or 1, provided that t=0 when V is hydrogen;

or a pharmaceutically acceptable salt thereof.

8. The compound according to claim 4 having the formula IV:

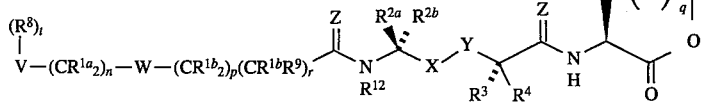

wherein:
  $R^{1a}$ is selected from:
    a) hydrogen, and
    b) $C_1-C_6$ alkyl;
  $R^{1b}$ are independently selected from:
    a) hydrogen,
    b) unsubstituted or substituted aryl or cycloalkyl, and
    c) $C_1-C_6$ alkyl unsubstituted or substituted by unsubstituted or substituted aryl, cycloalkyl, alkenyl, $R^{10}O-$ or $-N(R^{10})_2$;
  $R^{2a}$ is selected from:
    a) a side chain of a naturally occurring amino acid, wherein the amino acid is selected from alanine, leucine, isoleucine and valine;
    b) substituted or unsubstituted $C_1-C_{10}$ alkyl, $C_2-C_{10}$ alkenyl, $C_3-C_{10}$ cycloalkyl, aryl or heterocyclic group,
      wherein the substituent is selected from F, Cl, Br, $NO_2$, $R^{10}O-$, $R^{11}S(O)_m-$, $R^{10}C(O)NR^{10}-$, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and c) $C_1$–$C_6$ alkyl substituted with an unsubstituted or substituted group selected from aryl, heterocycle and $C_3$–$C_{10}$ cycloalkyl; and $R^{2b}$ is selected from hydrogen and $C_1$–$C_6$ alkyl; or $R^{2a}$ and $R^{2b}$ are combined to form —$(CH_2)_s$—;

$R^3$ and $R^4$ are independently selected from:
 a) a side chain of a naturally occurring amino acid,
 b) an oxidized form of a side chain of a naturally occurring amino acid which is:
  i) methionine sulfoxide, or
  ii) methionine sulfone,
 c) substituted or unsubstituted $C_1$–$C_{10}$ alkyl, $C_2$–$C_{10}$ alkenyl, $C_3$–$C_{10}$ cycloalkyl, aryl or heterocycle group,
  wherein the substituent is selected from F, Cl, Br, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
 d) $C_1$–$C_6$ alkyl substituted with an unsubstituted or substituted group selected from aryl, heterocycle and $C_3$–$C_{10}$ cycloalkyl;

X-Y is

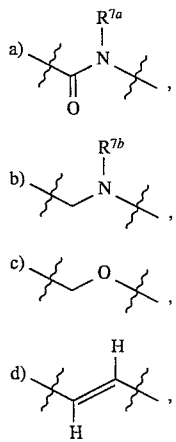

or e) —$CH_2$—$CH_2$—;

$R^{7a}$ is selected from
 a) hydrogen,
 b) unsubstituted or substituted aryl,
 c) unsubstituted or substituted heterocyclic,
 d) unsubstituted or substituted cycloalkyl, and
 e) $C_1$–$C_6$ alkyl substituted with hydrogen or an unsubstituted or substituted group selected from aryl, heterocyclic and cycloalkyl;
  wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
 a) hydrogen,
 b) unsubstituted or substituted aryl,
 c) unsubstituted or substituted heterocyclic,
 d) unsubstituted or substituted cycloalkyl,
 e) $C_1$–$C_6$ alkyl substituted with hydrogen or an unsubstituted or substituted group selected from aryl, heterocyclic and cycloalkyl,
 f) a carbonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl, and
 g) a sulfonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl;
  wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is independently selected from:
 a) hydrogen,
 b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and
 c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^9$ is selected from:
 hydrogen, $C_1$–$C_6$ lower alkyl, $R^{10}O$—, and —$N(R^{10})_2$;

$R^{10}$ is independently selected from hydrogen, $C_1$–$C_6$ alkyl, benzyl and aryl;

$R^{11}$ is independently selected from $C_1$–$C_6$ alkyl and aryl;

$R^{12}$ is hydrogen or $C_1$–$C_6$ alkyl;

V is selected from:
 a) aryl;
 b) heterocycle selected from pyrrolidinyl, imidazolyl, pyridinyl, thiazolyl, pyridonyl, 2-oxopiperidinyl, indolyl, quinolinyl, isoquinolinyl, and thienyl; and
 c) hydrogen;

W is
 —$S(O)_m$—, —O—, —NHC(O)—, —C(O)NH—, —$NHSO_2$—, —$SO_2NH$—, —$N(R^{7a})$— or —$N[C(O)R^{7a}]$—;

Z is independently $H_2$ or O;

m is 0, 1 or 2;

n is 0, 1, 2, 3 or 4, provided that n≠0 when V is hydrogen and W is —$S(O)_m$—;

p is 0, 1, 2, 3 or 4, provided that p≠0 when $R^9$ is not hydrogen or $C_1$–$C_6$ lower alkyl;

q is 0, 1 or 2;

r is 0 or 1;

s is 4 or 5; and t is 0 or 1, provided that t=0 when V is hydrogen;

or a pharmaceutically acceptable salt thereof.

9. A compound which inhibits farnesyl-protein transferase which is:

N-{2(S)-[(4-Nitrobenzylthio)acetamido]-3(S)-methylpentyl}-N(1-naphthylmethyl)-glycyl-methionine methyl ester, N-{2(S)-[(4-Nitrobenzylthio)acetamido]-3(S)-methylpentyl}-N(1-naphthylmethyl)-glycyl-methionine, N-{2(S)-[(Benzylthio)acetamido]-3(S)-methylpentyl}-N(1-naphthylmethyl)-glycyl-methionine, N-{2(S)-[(Benzylthio)acetamido]-3(S)-methylpentyl}-N(1-naphthylmethyl)-glycyl-methionine methyl ester, N-{2(S)-[(Phenylthio)acetamido]-3(S)-methylpentyl}- N(1-naphthylmethyl)-glycyl-methionine, N-{2(S)-[(Phenylthio)acetamido]-3(S)-methylpentyl}-N(1-naphthylmethyl)-glycyl-methionine methyl ester,
N-{2(S)-[(3-Nitrobenzylthio)acetamido]-3(S)-methylpentyl}-N(1-naphthylmethyl)-glycyl-methionine,
N-{2(S)-[(3-Nitrobenzylthio)acetamido]-3(S)-methylpentyl}-N(1-naphthylmethyl)-glycyl-methionine methyl ester,
N-{2(S)-[(2-Nitrobenzylthio)acetamido]-3(S)-methylpentyl}-N(1-naphthylmethyl)-glycyl-methionine,
N-{2(S)-[(2-Nitrobenzylthio)acetamido]-3(S)-methylpentyl}-N(1-naphthylmethyl)-glycyl-methionine methyl ester,
N-{2(S)-[(4-Cyanobenzylthio)acetamido]-3(S)-methylpentyl}-N(1-naphthylmethyl)-glycyl-methionine,
N-{2(S)-[(4-Cyanobenzylthio)acetamido]-3(S)-methylpentyl}-N-(1-naphthylmethyl)-glycyl-methionine methyl ester,
N-{2(S)-[(4-Trifluoromethylbenzylthio)acetamido]-3(S)-methylpentyl}-N-(1-naphthylmethyl)-glycyl-methionine,
N-{2(S)-[(4-Trifluoromethylbenzylthio)acetamido]-3(S)-methylpentyl}-N-(1-naphthylmethyl)-glycyl-methionine methyl ester,
N-{2(S)-[(4-Methoxybenzylthio)acetamido]-3(S)-methylpentyl}-N-(1-naphthylmethyl)-glycyl-methionine,
N-{2(S)-[(4-Methoxybenzylthio)acetamido]-3(S)-methylpentyl}-N-(1-naphthylmethyl)-glycyl-methionine methyl ester,
N-{2(S)-[(4-Methylsulfonylbenzylthio)acetamido]-3(S)-methylpentyl}-N-(1-naphthylmethyl)-glycyl-methionine,
N-{2(S)-[(4-Methylsulfonylbenzylthio)acetamido]-3(S)-methylpentyl}-N(1-naphthylmethyl)-glycyl-methionine methyl ester,
N-{2(S)-[(4-Phenylbenzylthio)acetamido]-3(S)-methylpentyl}-N-(1-naphthylmethyl)-glycyl-methionine,
N-{2(S)-[(4-Phenylbenzylthio)acetamido]-3(S)-methylpentyl}-N-(1-naphthylmethyl)-glycyl-methionine methyl ester,
N-{2(S)-[(4-(1-H-Tetrazol-5-yl)benzylthio)acetamido]-3(S)-methylpentyl}-N-(1-naphthylmethyl)-glycyl-methionine,
N-{2(S)-[(4-(1-H-Tetrazol-5-yl)benzylthio)acetamido]-3(S)-methylpentyl}-N-(1-naphthylmethyl)-glycyl-methionine methyl ester,
N-{2(S)-[(4-Methylbenzylthio)acetamido]-3(S)-methylpentyl}-N-(1-naphthylmethyl)-glycyl-methionine,
N-{2(S)-[(4-Methylbenzylthio)acetamido]-3(S)-methylpentyl}-N-(1-naphthylmethyl)-glycyl-methionine methyl ester,
N-{2(S)-[(8-Chloronaphth-1-ylthio)acetamido]-3(S)-methylpentyl}-N-(1-naphthylmethyl)-glycyl-methionine,
N-{2(S)-[(8-Chloronaphth-1-ylthio)acetamido]-3(S)-methylpentyl}-N-(1-naphthylmethyl)-glycyl-methionine methyl ester,
N-{2(S)-[((2-Methylindol-3-yl)thio)acetamido]-4-methylpentyl}-N-(1-naphthylmethyl)-glycyl-methionine,
N-{2(S)-[((2-Methylindol-3-yl)thio)acetamido]-4-methylpentyl}-N-(1-naphthylmethyl)-glycyl-methionine methyl ester,
N-{2(S)-[(4-Pyridylthio)acetamido]-3(S)-methylpentyl}-N-(1-naphthylmethyl)-glycyl-methionine,
N-{2(S)-[(4-Pyridylthio)acetamido]-3(S)-methylpentyl}-N-(1-naphthylmethyl)-glycyl-methionine methyl ester,
N-{2(S)-[(4-Picolinylthio)acetamido]-3(S)-methylpentyl}-N-(1-naphthylmethyl)-glycyl-methionine,
N-{2(S)-[(4-Picolinylthio)acetamido]-3(S)-methylpentyl}-N-(1-naphthylmethyl)-glycyl-methionine methyl ester,
N-{2(S)-[3-(Benzylthio)propionamido]-3(S)-methylpentyl}-N-(1-naphthylmethyl)-glycyl-methionine,
N-{2(S)-[(Benzyloxy)acetamido]-3(S)-methylpentyl}-N-(1-naphthylmethyl)-glycyl-methionine,
N-{2(S)-[(Benzyloxy)acetamido]-3(S)-methylpentyl}-N-(1-naphthylmethyl)-glycyl-methionine methyl ester,
N-{2(S)-[(N'-Benzylglycyl)amino]-3(S)-methylpentyl}-N-(1-naphthylmethyl)-glycyl-methionine,
N-{2(S)-[(N'-Benzylglycyl)amino]-3(S)-methylpentyl}-N-(1-naphthylmethyl)-glycyl-methionine methyl ester,
N-{2(S)-[(N'-Acetyl-N'-benzylglycyl)amino]-3(S)-methylpentyl}-N-(1-naphthylmethyl)-glycyl-methionine,
N-{2(S)-[(N'-Acetyl-N'-benzylglycyl)amino]-3(S)-methylpentyl}-N-(1-naphthylmethyl)-glycyl-methionine methyl ester,
N-{2(S)-[(N'-Benzyl-N'-t-butoxycarbonylglycyl)amino]-3(S)-methylpentyl}-N-(1-naphthylmethyl)-glycyl-methionine,
N-{2(S)-[(N'-Benzyl-N'-t-butoxycarbonylglycyl)amino]-3(S)-methylpentyl}-N-(1-naphthylmethyl)-glycyl-methionine methyl ester,
N-{2(S)-[(Benzylthio-S-oxide)acetamido]-3(S)-methylpentyl}-N-(1-naphthylmethyl)-glycyl-methionine,
N-{2(S)-[(Benzylthio-S-oxide)acetamido]-3(S)-methylpentyl}-N-(1-naphthylmethyl)-glycyl-methionine methyl ester,
N-{2(S)-[(Benzylthio-S,S-dioxide)acetamido]-3(S)-methylpentyl}-N-(1-naphthylmethyl)-glycyl-methionine,
N-{2(S)-[(Benzylthio-S,S-dioxide)acetamido]-3(S)-methylpentyl}-N-(1-naphthylmethyl)-glycyl-methionine methyl ester,
N-{2(S)-[(Benzylthio)acetamido]-3(S)-methylpentyl}-N-(1-naphthylmethyl)-glycyl-methionine sulfone,
N-{2(S)-[(Benzylthio)acetamido]-3(S)-methylpentyl}-N-(1-naphthylmethyl)-glycyl-methionine sulfone methyl ester,
N-{2(S)-[(N'-4-Nitrobenzoylglycyl)amino]-3(S)-methylpentyl}-N-(1-naphthylmethyl)-glycyl-methionine,
N-{2(S)-[(N'-4-Nitrobenzoylglycyl)amino]-3(S)-methylpentyl}-N-(1-naphthylmethyl)-glycyl-methionine methyl ester,
N-{2(S)-[(N'-Methyl-N'-4-nitrobenzoylglycyl)amino]-4-methylpentyl}-N-(1-naphthylmethyl)-glycyl-methionine,
N-{2(S)-[(N'-Methyl-N'-4-nitrobenzoylglycyl)amino]-4-methylpentyl}-N-(1-naphthylmethyl)-glycyl-methionine methyl ester,
N-{2(S)-[(S-Benzyl-L-cysteinyl)-3(S)-methylpentyl}-N-(1-naphthylmethyl)-glycyl-methionine,
N-{2(S)-[S-Benzyl-L-cysteinyl]-3(S)-methylpentyl}-N-(1-naphthylmethyl)-glycyl-methionine methyl ester,
N-{2(S)-[S-Benzyl-D-cysteinyl]-3(S)-methylpentyl}-N-(1-naphthylmethyl)-glycyl-methionine,
N-{2(S)-[S-Benzyl-D-cysteinyl]-3(S)-methylpentyl}-N-(1-naphthylmethyl)-glycyl-methionine methyl ester,
3-Benzylthiopropionyl-valyl-isoleucyl-methionine,
N-[2(S)-(2(S),3-Diaminopropionyl)amino-3(S)-methylpentyl]-N-(1-naphthylmethyl)glycyl-methionine,
N-[2(S)-(2(S),3-Diaminopropionyl)amino-3(S)-methylpentyl]-N-(1-naphthylmethyl)glycyl-methionine methyl ester,
N-[2(S)-(3-Aminopropionyl)amino-3(S)-methylpentyl]-N-(1-naphthylmethyl)glycyl-methionine,
N-[2(S)-(3-Aminopropionyl)amino-3(S)-methylpentyl]-N-(1-naphthylmethyl)glycyl-methionine methyl ester,
N-(2(S)-L-Glutaminylamino-3(S)-methylpentyl)-N-(1-naphthyl-methyl)glycyl-methionine,
N-(2(S)-L-Glutaminylamino-3(S)-methylpentyl)-N-(1-naphthyl-methyl)glycyl-methionine methyl ester,
N-[2(S)-(1,1-Dimethylethoxycarbonylamino)-3S)-methylpentyl]-N-(1-naphthylmethyl)glycyl-methionine, N-[2(S)-(1,1-Dimethylethoxycarbonylamino)-3S)-methyl-pentyl]-N-(1-naphthylmethyl)glycyl-methionine methyl ester,
N-[2(S)-(1,1-Dimethylethoxycarbonylamino)-3(S)-methyl-pentyl]-N-benzylglycyl-methionine,
N-[2(S)-(1,1-Dimethylethoxycarbonylamino)-3(S)-methyl-pentyl]-N-benzylglycyl-methionine methyl ester,
N-{[1-(4-Nitrobenzylthio)acetylamino]cyclopent-1-ylm-ethyl}-N-(1-naphthylmethyl)-glycyl-methionine,
N-{[1-(4-Nitrobenzylthio)acetylamino]cyclopent-1-ylm-ethyl}-N-(1-naphthylmethyl)-glycyl-methionine methyl ester,
N-{2(S)-[2-(4-Nitrophenyl)ethylcarbamoylamino]-4-methylpentyl}-N-(1-naphthylmethyl)-glycyl-methionine,
N-{2(S)-[2-(4-Nitrophenyl)ethylcarbamoylamino]-4-methylpentyl}-N-(1-naphthylmethyl)-glycyl-methionine methyl ester,
N-{2(S)-[(3(S)-tetrahydrofuryloxy)carbonylamino]-3(S)-methylpentyl}-N-(1-naphthylmethyl)-glycyl-methionine,
N-{2(S)-[(3(S)-tetrahydrofuryloxy)carbonylamino]-3(S)-methylpentyl}-N-(1-naphthylmethyl)-glycyl-methionine methyl ester,
N-{2(S)-[(cis-4-benzyloxytetrahydrofur-3-yloxy)carbony-lamino]-3(S)-methylpentyl}-N-(1-naphthylmethyl)-glycyl-methionine,
N-{2(S)-[(cis-4-benzyloxytetrahydrofur-3-yloxy)carbony-lamino]-3(S)-methylpentyl}-N-(1-naphthylmethyl)-glycyl-methionine methyl ester,
N-{2(S)-[(N'-Methyl-N'-4-nitrophenylacetylglycyl)amino]-4-methylpentyl}-N-(1-naphthylmethyl)-glycyl-methionine or
N-{2(S)-[(N'-Methyl-N'-4-nitrophenylacetylglycyl)amino]-4-methylpentyl}-N-(1-naphthylmethyl)-glycyl-methionine methyl ester or a pharmaceutically acceptable salt thereof.

10. A compound which inhibits farnesyl-protein transferase which is:
N-{2(S)-[(4-Methoxybenzylthio)acetamido]-3(S)-methyl-pentyl}-N-(1-naphthylmethyl)-glycyl-methionine

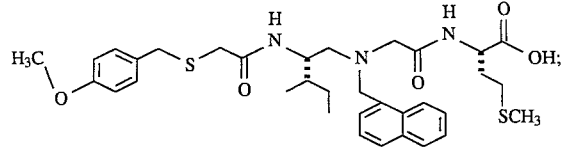

or the pharmaceutically acceptable salts thereof.

11. A compound which inhibits farnesyl-protein transferase which is:
N-{2(S)-[(4-Methoxybenzylthio)acetamido]-3(S)-methyl-pentyl}-N-(1-naphthylmethyl)-glycyl-methionine methyl ester

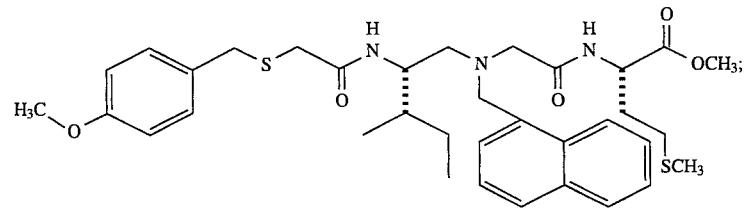

or a pharmaceutically acceptable salt thereof.

12. A compound which inhibits farnesyl-protein transferase which is:

N-{2(S)-[(4-Cyanobenzylthio)acetamido]-3(S)-methylpen-tyl}-N-(1-naphthylmethyl)-glycyl-methionine

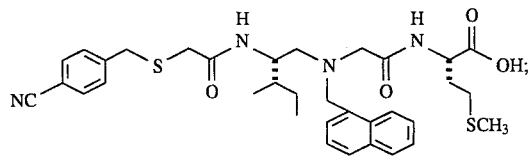

or a pharmaceutically acceptable salt thereof.

13. A compound which inhibits farnesyl-protein transferase which is:
N-{2(S)-[(4-Cyanobenzylthio)acetamido]-3(S)-methylpen-tyl}-N-(1-naphthylmethyl)-glycyl-methionine methyl ester

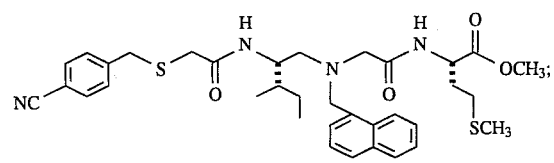

or a pharmaceutically acceptable salt thereof.

14. A compound which inhibits farnesyl-protein transferase which is:
N-(2(S)-L-Glutaminylamino-3(S)-methylpentyl)-N-(1-naphthylmethyl)glycyl-methionine

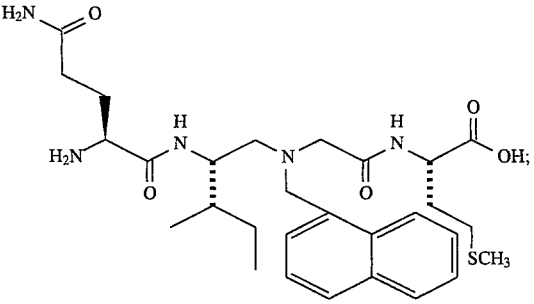

or a pharmaceutically acceptable salt thereof.

15. A compound which inhibits farnesyl-protein transferase which is:

N-(2(S)-L-Glutaminylamino-3(S)-methylpentyl)-N-(1-naphthylmethyl)glycyl-methionine methyl ester

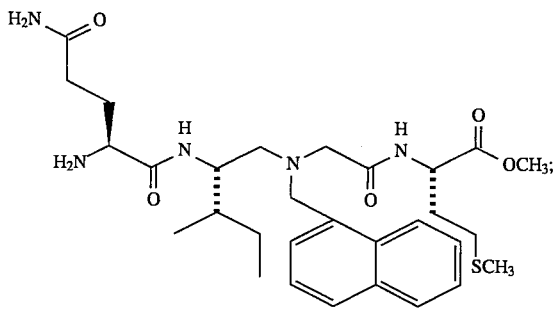

or a pharmaceutically acceptable salt thereof.

16. A compound which inhibits farnesyl-protein transferase which is:
N-{2(S)-[(Benzylthio)acetamido]-3(S)-methylpentyl}-N-(1-naphthylmethyl)-glycyl-methionine sulfone

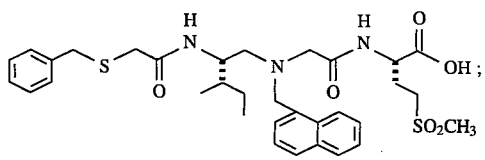

or a pharmaceutically acceptable salt thereof.

17. A compound which inhibits farnesyl-protein transferase which is:
N-{2(S)-[(Benzylthio)acetamido]-3(S)-methylpentyl}-N-(1-naphthylmethyl)-glycyl-methionine sulfone methyl ester

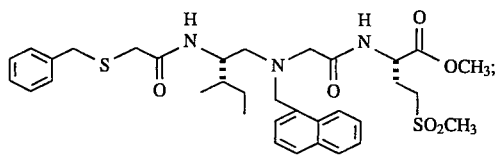

or a pharmaceutic ally acceptable salt thereof.

18. A pharmaceutical composition comprising a pharmaceutical carrier, and dispersed therein, a therapeutically effective amount of a compound of claim 1.

19. A pharmaceutical composition comprising a pharmaceutical carrier, and dispersed therein, a therapeutically effective amount of a compound of claim 2.

20. A pharmaceutical composition comprising a pharmaceutical carrier, and dispersed therein, a therapeutically effective amount of a compound of claim 3.

21. A pharmaceutical composition comprising a pharmaceutical carrier, and dispersed therein, a therapeutically effective amount of a compound of claim 4.

22. A pharmaceutical composition comprising a pharmaceutical carrier, and dispersed therein, a therapeutically effective amount of a compound of claim 9.

23. A method for inhibiting farnesylation of Ras protein which comprises administering to a mammal in need thereof a therapeutically effective amount of the composition of claim 18.

24. A method for inhibiting farnesylation of Ras protein which comprises administering to a mammal in need thereof a therapeutically effective amount of the composition of claim 19.

25. A method for inhibiting farnesylation of Ras protein which comprises administering to a mammal in need thereof a therapeutically effective amount of the composition of claim 20.

26. A method for inhibiting farnesylation of Ras protein which comprises administering to a mammal in need thereof a therapeutically effective amount of the composition of claim 21.

27. A method for inhibiting farnesylation of Ras protein which comprises administering to a mammal in need thereof a therapeutically effective amount of the composition of claim 22.

* * * * *

UNITED STATES PATENT AND TRADEMARK OFFICE
CERTIFICATE OF CORRECTION

PATENT NO. : 5,585,359

DATED : December 17, 1996

INVENTOR(S) : Michael J. Breslin, S. Jane deSolms, Samuel L. Graham, John H. Hutchinson and Gerald E. Stokker It is certified that error appears in the above-indentified patent and that said Letters Patent is hereby corrected as shown below:

In Column 64, line 51 should read as follows:

-- provided that $R^{1b}$ is not $R^{10}C(O)NR^{10}$- when $R^{1a}$ is --.

In Column 68, line 58 should read as follows:

-- $R^{7a}$ is selected from --.

In Column 69, line 29 should read as follows:

-- $R^{10}C(O)NR^{10}$-, CN, $NO_2$, $R^{10}{}_2N-C(NR^{10})$-, --.

In Column 69, line 35 should read as follows:

-- $R^{10}C(O)NH$-, CN, $H_2N-C(NH)$-, $R^{10}C(O)$-, --.

In Column 74, line 44 should read as follows:

-- $R^{10}OC(O)$-, $-N(R^{10})_2$, or $R^{11}OC(O)NR^{10}$-, and --.

In Column 74, in the last line, place a -- ; -- after "O".

In Column 75, delete lines 56 & 57 and insert

-- CN, $(R^{10})_2N-C(NR^{10})$-, --.

In Column 80, at line 2, after "Cl," delete "$R^{10}0$-" and replace it with
-- $R^{10}O$- --.

UNITED STATES PATENT AND TRADEMARK OFFICE
CERTIFICATE OF CORRECTION

PATENT NO. : 5,585,359

DATED : December 17, 1996

INVENTOR(S) : Michael J. Breslin, S. Jane deSolms, Samuel L. Graham, John H. Hutchinson and Gerald E. Stokker It is certified that error appears in the above-indentified patent and that said Letters Patent is hereby corrected as shown below:

In Column 80, line 4, after "or" and before "and" it should read
-- $R^{11}OC(O)NR^{10}$-, --.

In Column 87, line 42 should read as follows:

-- or a pharmaceutically acceptable salt thereof. --.

Signed and Sealed this

Tenth Day of June, 1997

*Attest:*

BRUCE LEHMAN

*Attesting Officer*     Commissioner of Patents and Trademarks